US010479853B2

(12) United States Patent
Takagiwa et al.

(10) Patent No.: US 10,479,853 B2
(45) Date of Patent: Nov. 19, 2019

(54) SURFACE-TREATED CARBON NANOTUBE AND RESIN COMPOSITION

(71) Applicant: ASAHI KASEI CHEMICALS CORPORATION, Tokyo (JP)

(72) Inventors: Aya Takagiwa, Tokyo (JP); Teruaki Sakuma, Tokyo (JP); Yasukazu Shikano, Tokyo (JP); Kazuya Noda, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 1383 days.

(21) Appl. No.: 14/382,796

(22) PCT Filed: Mar. 5, 2013

(86) PCT No.: PCT/JP2013/056041
§ 371 (c)(1),
(2) Date: Sep. 4, 2014

(87) PCT Pub. No.: WO2013/133292
PCT Pub. Date: Sep. 12, 2013

(65) Prior Publication Data
US 2015/0018490 A1 Jan. 15, 2015

(30) Foreign Application Priority Data

Mar. 5, 2012 (JP) .................. 2012-048374
Mar. 5, 2012 (JP) .................. 2012-048377
(Continued)

(51) Int. Cl.
C08F 220/08 (2006.01)
C08F 120/06 (2006.01)
(Continued)

(52) U.S. Cl.
CPC .......... *C08F 220/08* (2013.01); *C07C 59/265* (2013.01); *C07D 307/32* (2013.01);
(Continued)

(58) Field of Classification Search
CPC ................................. C01B 31/0253
See application file for complete search history.

(56) References Cited

U.S. PATENT DOCUMENTS

2004/0202603 A1    10/2004  Fischer et al.
2005/0147553 A1*    7/2005  Wong ............... B82Y 30/00
                                        423/447.2
(Continued)

FOREIGN PATENT DOCUMENTS

CN    101104668 A    1/2008
EP      2138535 A1   12/2009
(Continued)

OTHER PUBLICATIONS

International Search Report issued with respect to application No. PCT/JP2013/056041, dated May 7, 2013.
(Continued)

*Primary Examiner* — Ling Siu Choi
*Assistant Examiner* — Thuy-Ai N Nguyen
(74) *Attorney, Agent, or Firm* — Greenblum & Bernstein, P.L.C.

(57) ABSTRACT

Provided is a surface-treated carbon nanotube having few surface fractures, not reducing the molecular weight of the resin to be mixed and having excellent extrudability. In the surface-treated carbon nanotube, the thermal reduction amount at 600° C. in a nitrogen atmosphere is 0.2 to 40%, the surface oxygen concentration measured by X-ray photoelectron spectroscopy (XPS) is 1.5 to 40 atm % and the surface sulfur concentration is less than 0.1 atm %.

21 Claims, 5 Drawing Sheets

| (30) | Foreign Application Priority Data | | |
|---|---|---|---|
| Mar. 5, 2012 | (JP) | | 2012-048454 |
| Mar. 5, 2012 | (JP) | | 2012-048459 |

(51) Int. Cl.
    *C08F 220/06* (2006.01)
    *C08L 77/06* (2006.01)
    *C07D 307/32* (2006.01)
    *C08K 3/04* (2006.01)
    *C08K 5/053* (2006.01)
    *C07C 59/265* (2006.01)
    *C08F 210/02* (2006.01)

(52) U.S. Cl.
    CPC .......... *C08F 120/06* (2013.01); *C08F 210/02* (2013.01); *C08F 220/06* (2013.01); *C08L 77/06* (2013.01)

(56) References Cited

U.S. PATENT DOCUMENTS

| 2006/0098389 A1 | 5/2006 | Liu et al. |
| 2012/0058889 A1 | 3/2012 | Nishino et al. |

FOREIGN PATENT DOCUMENTS

| EP | 2218682 A1 | 8/2010 |
| JP | 2002-503204 A | 1/2002 |
| JP | 2006-117495 A | 5/2006 |
| JP | 2006-213569 A | 8/2006 |
| JP | 2008-001749 A | 1/2008 |
| JP | 2010-001475 A | 1/2010 |
| JP | 2010-173886 A | 8/2010 |
| JP | 2010-254546 A | 11/2010 |

OTHER PUBLICATIONS

International Preliminary Report on Patentability issued with respect to application No. PCT/JP2013/056041, dated Sep. 9, 2014.

European Search Report issued with respect to application No. 13758569.1, dated Oct. 20, 2015.

Chun-Hao Tseng et al., "Functionalizing Carbon Nanotubes by Plasma Modification for the Preparation of Covalent-Integrated Epoxy Composites", Chemistry of Materials, vol. 19, No.2, Jan. 1, 2007(Jan. 1, 2007), pp. 308-315.

Kuan Chen-Feng et al., "Mechanical and electrical properties of multi-wall carbon nanotube/poly (lactic acid) composites", Journal of Physics and Chemistry of Solids, Pergamon Press, London, GB, vol. 69, No. 5-6, May 1, 2008 (May 1, 2008), pp. 1395-1398.

Liu Manhong et al.,"Chemical modification of single-walled carbon nanotubes with peroxytrifluoroacetic acid", Carbon, Elsevier, Oxford, GB, vol. 43, No. 7, Jun. 1, 2005(Jun. 1, 2005), pp. 1470-1478.

S. Chen et al., "Preparation of Poly(acrylic acid) Grafted Multiwalled Carbon Nanotubes by a Two-Step Irradiation Technique", Macromolecules 2006, vol. 39, pp. 330-334.

\* cited by examiner

SURFACE-TREATED CARBON NANOTUBE AND RESIN COMPOSITION

TECHNICAL FIELD

The present invention relates to a surface-treated carbon nanotube and a resin composition.

BACKGROUND ART

Carbon nanotubes are excellent in electrical properties and the like. In view of this, various application fields are expected. For example, composite materials obtained by mixing a carbon nanotube with a resin are expected as materials providing excellent properties; however, sufficient effects have not yet been obtained at present. To describe more specifically, even if a carbon nanotube to which no surface treatment is applied is mixed with a resin, the carbon nanotube is only physically in contact with the resin and the addition effect of the carbon nanotube cannot be sufficiently obtained. Accordingly, e.g., introducing a functional group into a carbon nanotube by applying some sort of surface treatment to the carbon nanotube has been investigated. Examples include a carbon nanotube to which a surface treatment using a mixed acid of sulfuric acid/nitric acid is applied. Other examples include a carbon nanotube to which a surface treatment using a mixed acid of sulfuric acid/hydrogen peroxide is applied (Patent Document 1).

Composite materials obtained by dispersing a carbon nanotube in a resin have been expected as materials that can attain high strength and weight reduction. Even in such composite materials, carbon nanotubes to which a surface treatment is applied are used in order to improve the addition effect of the carbon nanotubes. Examples include composite materials obtained by dispersing a carbon nanotube to which a surface treatment using a mixed acid of sulfuric acid/nitric acid is applied in a resin. However, use of a mixed acid of sulfuric acid/nitric acid has a problem in that the mixed acid causes an extremely strong reaction and destroys the graphene layer of a carbon nanotube, with the result that the strength of the carbon nanotube itself decreases. To deal with this problem, it has been reported to employ a method of treating a carbon nanotube with an acid of low concentration (Patent Document 2).

PATENT DOCUMENT

Patent Document 1: Japanese Patent Laid-Open No. 2006-213569
Patent Document 2: Japanese Patent Laid-Open No. 2008-001749

SUMMARY OF THE INVENTION

Problems to be Solved by the Invention

Conventional carbon nanotubes whose surface is treated have not yet produced sufficient effects. For example, a carbon nanotube whose surface is treated with a mixed acid of sulfuric acid/nitric acid in order to introduce a functional group into the carbon nanotube has a problem in that the surface of the carbon nanotube is destroyed. Such a surface fracture will be an obstacle which prevents improvement of physical properties of a composite material obtained by mixing the carbon nanotube with a resin.

In a carbon nanotube whose surface is treated with a mixed acid, the acidity of which is reduced by using sulfuric acid in combination with hydrogen peroxide, as disclosed in Patent Document 1, formation of surface fracture on the carbon nanotube can be prevented to some extent; however, when the carbon nanotube is mixed with a resin, the molecular weight of the resin significantly reduces. This is a problem. The present inventors conducted intensive studies about the problem. As a result, they found out as a cause that a sulfur compound remaining on the carbon nanotube cuts the molecular chain of a resin.

When the surface of a carbon nanotube is treated with a strong acid such as sulfuric acid and nitric acid even in a small amount, the strong acid inevitably remains in a trace amount on the surface of the carbon nanotube even though the surface is washed. The remaining strong acid cuts the molecular chain of a resin and reduces a molecular weight of the resin. In addition to this problem, metal parts (e.g., screws) of an extruder, etc. used in kneading with the resin are eroded and abraded by the remaining strong acid. A problem of lowering extrudability occurs.

When composite materials are obtained by dispersing a carbon nanotube in a resin, the physical properties thereof still have room for improvement. In composite materials using a carbon nanotube to which no surface treatment is applied, since the carbon nanotube is just physically in contact with a resin, neither sufficient strength nor toughness is obtained. Like in Patent Document 2, if a carbon nanotube whose surface is treated with a low concentration acid is used, fracture of a graphene layer might be suppressed; however, remaining sulfur atoms and the like provide a negative effect upon a resin. Thus, neither sufficient strength nor toughness is obtained.

As described above, as a matter of fact, sufficient strength and toughness of composite materials using conventional carbon nanotubes have not yet been obtained. In particular, composite materials mentioned above are desired to have excellent strength and toughness not only at normal temperature but also at high temperature. More specifically, automotive parts for use in portions around engines and dashboards of automobiles are required to have excellent strength and toughness even at high temperature.

A first object of the present invention is to provide a surface-treated carbon nanotube having few surface fractures, not reducing the molecular weight of the resin to be mixed and also having excellent extrudability.

A second object of the present invention is to provide a surface-treated carbon nanotube providing excellent strength and toughness at high temperature when the carbon nanotube is mixed with a resin.

A third object of the present invention is to provide a resin composition having excellent strength and toughness at high temperature, as a carbon-nanotube composite material.

A fourth object of the present invention is to provide a resin composition having excellent strength and toughness at high temperature, as a carbon-nanotube composite material.

Means for Solving the Problems

The present inventors conducted intensive studies with a view to attaining the aforementioned objects. As a result, they found use of a predetermined surface-treated carbon nanotube and accomplished the present invention.

More specifically, the present invention is as follows.

[1]
A surface-treated carbon nanotube wherein
a thermal reduction amount at 600° C. in a nitrogen atmosphere is 0.2 to 40%;

a surface oxygen concentration measured by X-ray photoelectron spectroscopy (XPS) is 1.5 to 40 atm %; and a surface sulfur concentration is less than 0.1 atm %.

[2]

The surface-treated carbon nanotube according to [1], wherein the thermal reduction amount at 600° C. in a nitrogen atmosphere is 0.5 to 40%.

[3]

The surface-treated carbon nanotube according to [1] or [2], wherein a surface treatment with at least one selected from the group consisting of an inorganic acid, an organic acid and a polymer having an organic acid as a polymerization unit is applied.

[4]

The surface-treated carbon nanotube according to [3], wherein the inorganic acid is hydrogen peroxide.

[5]

The surface-treated carbon nanotube according to [4], wherein a ratio (Id/Ig) of a peak area (Id) of a band having a range of 1335 to 1365 $cm^{-1}$ to a peak area (Ig) of a band having a range of 1565 to 1600 $cm^{-1}$ in a Raman scattering spectrum is 1.0 to 2.0.

[6]

The surface-treated carbon nanotube according to [3], wherein the organic acid is at least one selected from the group consisting of citric acid, oxalic acid, acrylic acid, diacrylic acid, methacrylic acid, maleic acid, fumaric acid, dimethylfumaric acid, itaconic acid, citraconic acid, fumaric anhydride, maleic anhydride, benzoic anhydride and acetic anhydride.

[7]

The surface-treated carbon nanotube according to [3], wherein the polymer having an organic acid as a polymerization unit is at least one selected from the group consisting of a poly(acrylic acid), a poly(acrylic acid-co-maleic acid), an ethylene-maleic anhydride and a styrene-maleic anhydride.

[8]

The surface-treated carbon nanotube according to any one of [1] to [7], containing a compound represented by any one of formula (1) to formula (4):

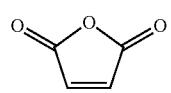
(1)

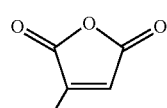
(2)

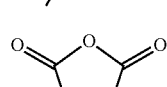
(3)

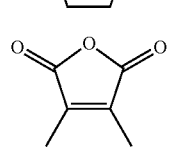
(4)

[9]

The surface-treated carbon nanotube according to [8], wherein a total content of a compound represented by any one of formula (1) to formula (4) in the surface-treated carbon nanotube is 0.5 to 40 mass %.

[10]

The surface-treated carbon nanotube according to [8] or [9], further containing a compound represented by formula (5) or formula (6):

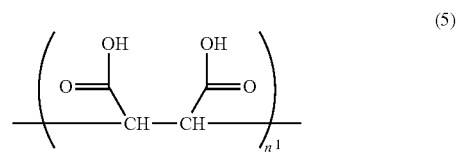
(5)

where $n^1$ is an integer of 2 to 400,

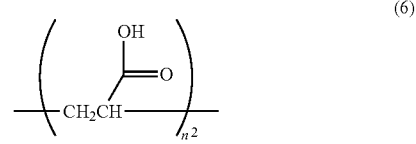
(6)

where $n^2$ is an integer of 2 to 650.

[11]

The surface-treated carbon nanotube according to [10], wherein a total content of a compound represented by formula (5) or formula (6) in the surface-treated carbon nanotube is 0.5 to 40 mass %.

[12]

The surface-treated carbon nanotube according to any one of [6] to [11], wherein a ratio (Id/Ig) of a peak area (Id) of a band having a range of 1335 to 1365 $cm^{-1}$ to a peak area (Ig) of a band having a range of 1565 to 1600 $cm^{-1}$ in a Raman scattering spectrum is 0.1 to 0.9.

[13]

The surface-treated carbon nanotube according to any one of [6] and [8] to [12], wherein the surface treatment by using at least a maleic anhydride is applied.

[14]

The surface-treated carbon nanotube according to any one of [1] to [3] and [5] to [13], wherein the surface treatment is performed in the absence of a solvent.

[15]

A resin composition comprising a surface-treated carbon nanotube according to any one of [1] to [14] and a thermoplastic resin.

[16]

The resin composition according to [15], wherein the thermoplastic resin is at least a polyamide.

[17]

A molded article comprising a resin composition according to [15] or [16].

[18]

A surface-treated carbon nanotube containing a compound represented by any one of formula (1) to formula (4):

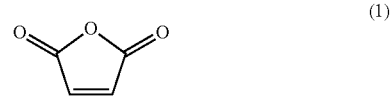
(1)

-continued $$\text{(2)}$$

$$\text{(3)}$$

$$\text{(4)}$$

[19]
The surface-treated carbon nanotube according to [18], further containing a compound represented by formula (5) or formula (6):

$$\left(\begin{array}{cc} \text{OH} & \text{OH} \\ \text{O}= & =\text{O} \\ -\text{CH}-\text{CH}- \end{array}\right)_{n^1} \quad (5)$$

where $n^1$ is an integer of 2 to 400, $$\left(\begin{array}{c} \text{OH} \\ =\text{O} \\ -\text{CH}_2\text{CH}- \end{array}\right)_{n^2} \quad (6)$$

where $n^2$ is an integer of 2 to 650.

[20]
The surface-treated carbon nanotube according to [18] or [19], wherein a surface treatment by using at least a maleic anhydride is applied.

[21]
The surface-treated carbon nanotube according to [20], wherein the surface treatment is performed in the absence of a solvent.

[22]
A resin composition comprising a surface-treated carbon nanotube according to any one of [18] to [21] and a thermoplastic resin.

[23]
The resin composition according to [22], wherein the thermoplastic resin is at least a polyamide.

[24]
A molded article comprising a resin composition according to [22] or [23].

[25]
A polyamide resin composition, comprising
a surface-treated carbon nanotube in which a ratio (Id/Ig) of a peak area (Id) of a band having a range of 1335 to 1365 cm$^{-1}$ to a peak area (Ig) of a band having a range of 1565 to 1600 cm$^{-1}$ in a Raman scattering spectrum is 0.1 to 2.0; and
a polyamide resin,
wherein a specific strength of an ISO36 Type3 dumbbell at 120° C. is 35 MPa or more.

[26]
The polyamide resin composition according to [25], wherein
the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum of the surface-treated carbon nanotube is 0.1 to 0.9; and
a peak temperature of cooling crystallization temperature of the polyamide resin composition measured by differential scanning calorimetry (DSC) is 240° C. or less.

[27]
The polyamide resin composition according to [25], wherein
the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum of the surface-treated carbon nanotube is 1.0 to 2.0; and
the peak temperature of cooling crystallization temperature of the polyamide resin composition measured by differential scanning calorimetry (DSC) is 234° C. or less.

[28]
A molded article comprising a polyamide resin composition according to any one of [25] to [27].

[29]
A polyamide resin composition comprising a surface-treated carbon nanotube and a polyamide resin, wherein
a content of an organic substance in the surface-treated carbon nanotube having a deposit of the organic substance and obtained by an elution treatment of the polyamide resin composition with hexafluoroisopropanol is 2 to 10 mass %.

[30]
The polyamide resin composition according to [29], wherein a surface sulfur concentration of the surface-treated carbon nanotube having a deposit of the organic substance and measured by X-ray photoelectron spectroscopy is less than 0.1 atm %.

[31]
The polyamide resin composition according to [29] or [30], wherein a surface nitrogen concentration of the surface-treated carbon nanotube having a deposit of the organic substance and measured by X-ray photoelectron spectroscopy (XPS) is 1 to 15 atm %.

[32]
The polyamide resin composition according to any one of [29] to [31], wherein the organic substance comprises a compound represented by any one of formula (1) to formula (4):

$$\text{(1)}$$

$$\text{(2)}$$

$$\text{(3)}$$

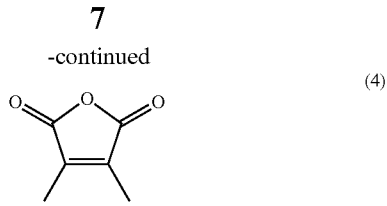

(4)

[33]
A molded article comprising a polyamide resin composition according to any one of [29] to [32].

Advantageous Effects of the Invention

According to the present invention, is possible to provide a surface-treated carbon nanotube having few surface fractures, not reducing the molecular weight of the resin to be mixed and also having excellent extrudability.

According to the present invention, it is possible to provide a surface-treated carbon nanotube providing excellent strength and toughness at high temperature when the carbon nanotube is mixed with a resin.

According to the present invention, it is possible to provide a resin composition having excellent strength and toughness at high temperature, as a carbon-nanotube composite material.

DESCRIPTION OF EMBODIMENTS

Figure 1:
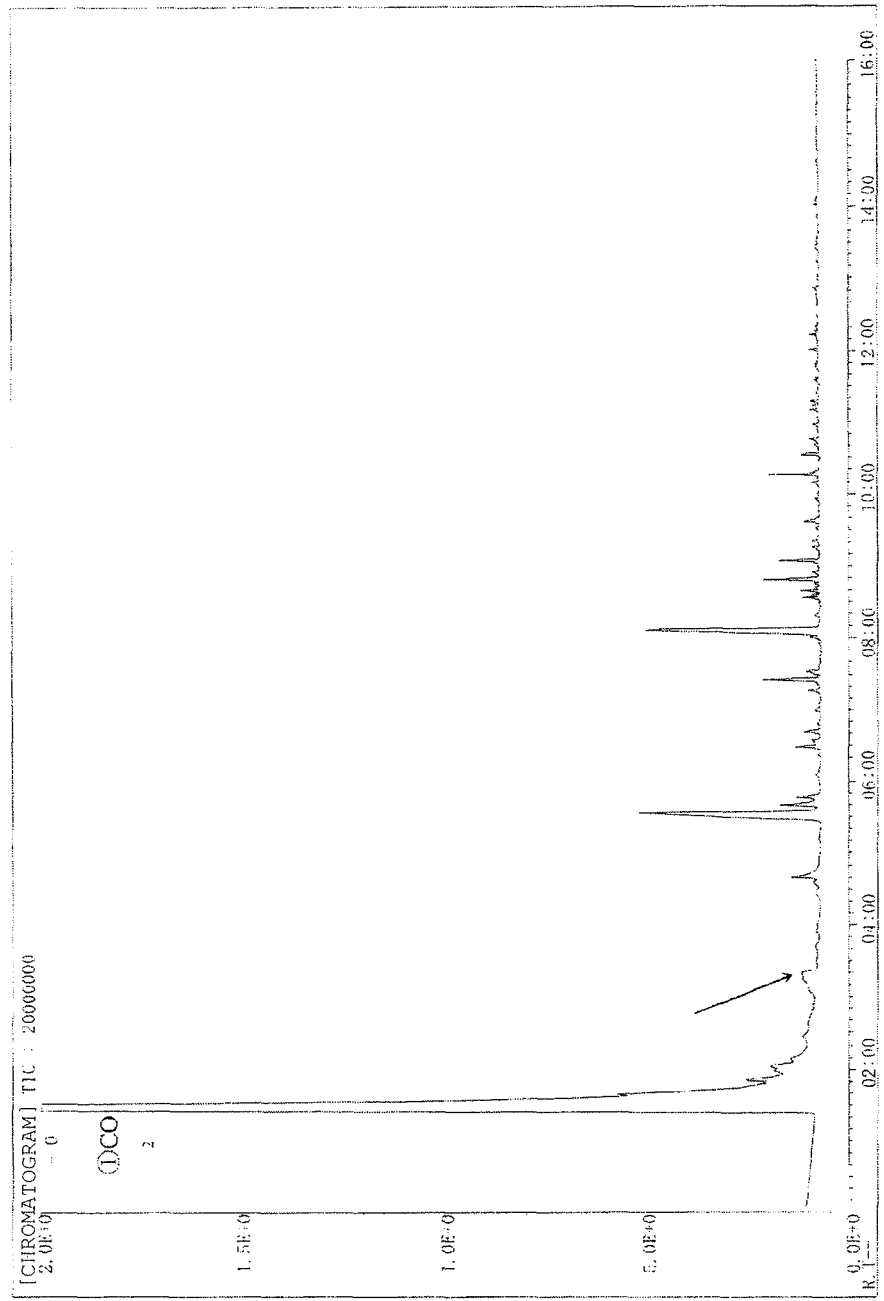
FIG. 1 is a chromatograph obtained by pyrolysis-gas chromatography/mass spectroscopy (Py-GC/MS) of the residue (bound substance) of the surface-treated carbon nanotube of Example 1-2 after washing.

Embodiments (hereinafter, simply referred to as "the embodiment") for carrying out the present invention will be more specifically described below. The embodiments below are just examples for illustrating the present invention and will not be construed as limiting the present invention to the following contents. The present invention can be carried out by appropriately modifying it within the scope of the present invention.

The First Embodiment

The carbon nanotube of the embodiment is a carbon nanotube whose surface is treated (hereinafter, sometimes simply referred to as "surface-treated carbon nanotube") and in which a thermal reduction amount at 600° C. in a nitrogen atmosphere is 0.2 to 40%; the surface oxygen concentration measured by X-ray photoelectron spectroscopy (XPS) is 1.5 to 40 atm %; and the surface sulfur concentration is less than 0.1 atm %. The surface-treated carbon nanotube has few surface fractures, does not reduce the molecular weight of the resin to be mixed and also has excellent extrudability.

(Raw Material for Carbon Nanotube)

A carbon nanotube (carbon nanotube before a surface treatment) serving as a raw material for the surface-treated carbon nanotube of the embodiment may be either a single-layer carbon nanotube or a multilayer carbon nanotube of two or more layers. The layer structure of the carbon nanotube can be selected depending upon the purpose. In view of manufacturing cost and dispersibility to a resin, a multilayer carbon nanotube of two or more layers is preferred. Since the multilayer carbon nanotube of two or more layers has good dispersibility to a resin, strength and the like can be further improved.

A manufacturing method for a carbon nanotube is not particularly limited and any manufacturing method conventionally known may be employed including a vapor-phase growth process, an arc discharge process, a laser vaporization process and a HiPco process (high-pressure carbon monoxide process).

Now, a method for manufacturing a multilayer carbon nanotube by the vapor-phase growth process will be described below by way of example. Specifically, e.g., a method for obtaining a fiber structure (hereinafter, referred to as an "ungraphitized carbon nanotube") by chemical pyrolysis of an organic compound such as a hydrocarbon by CVD method using an organic transition metal compound such as ferrocene and nickelocene as a metal catalyst; a method for producing a carbon nanotube in a suspension state; and a method for growing a carbon nanotube along a wall of a reacting furnace can be used. Alternatively, a carbon nanotube can be obtained by bringing a metal-containing particle previously fixed to a refractory support made of alumina, carbon or the like into contact with an organic compound such as a hydrocarbon at high temperature.

When a surface treatment described later is applied to a carbon nanotube, the carbon nanotube can be selected from an ungraphitized carbon nanotube, a graphitized carbon nanotube and an intermediate carbon nanotube between them depending upon the purpose.

To improve the strength of a carbon nanotube itself, it is preferable to use a graphitized carbon nanotube. The graphitized carbon nanotube can be prepared by annealing an ungraphitized carbon nanotube. The annealing temperature is preferably 1000 to 3000° C. and more preferably 2500 to 3000° C.

The graphitized carbon nanotube is preferably a multilayer carbon nanotube having a high degree of graphitization. The higher the annealing temperature, the higher the degree of graphitization tends to be. In addition, the annealing temperature is preferably high since an amorphous deposit and impurities such as remaining catalyst metal precipitated on the surface of a carbon nanotube are removed. It is preferable if the annealing temperature of a carbon nanotube is 2500° C. or more since the skeleton of the carbon nanotube is more highly graphitized (crystallized) and the number of defects of carbon nanotube is further reduced.

A method for manufacturing a carbon nanotube from an organic compound will be described. In manufacturing a carbon nanotube, as an organic compound serving as a raw material, carbon compounds including hydrocarbons such as benzene, toluene and xylene, carbon monoxide and alcohols such as ethanol are used. Of them, two or more carbon compounds different in decomposition temperature are preferably used as a carbon source. Note that the "two or more carbon compounds" refers to not only the case where two or more organic compounds serving as a raw material are used but also the case where, e.g., even if a single organic compound is used as a raw material, two or more carbon compounds different in decomposition temperature are produced during a carbon nanotube synthesis process, for example, through a hydrogenating dealkylation reaction of toluene and xylene and the following pyrolysis reaction. Examples of the atmosphere gas that can be employed for pyrolysis include inactive gases such as argon, helium and xenon, and hydrogen. As the catalyst, a mixture of a transition metal such as iron, cobalt and molybdenum or a transition metal compound such as ferrocene or an acetic acid metal salt and sulfur or a sulfur compound such as thiophene or iron sulfide can be used.

The intermediate can be produced in accordance with a CVD method of hydrocarbons or the like usually performed, by vaporizing a mixture solution of a hydrocarbon serving as a raw material and a catalyst, introducing e.g., hydrogen gas as a carrier gas into a reacting furnace, and performing pyrolysis at a temperature of 400 to 1300° C. Through such a pyrolysis, fibers having an outer diameter of about 10 to 500 nm may be mutually entangled around a granular material grown from a catalyst particle as a nucleus to form a less-dense carbon nanotube. The carbon nanotubes serving as structural units get together to form a carbon-nanotube assembly of several centimeters to several tens of centimeters in size.

In improving the surface reactivity of a carbon nanotube, an ungraphitized carbon nanotube is preferably used. To be more specific, the ungraphitized carbon nanotube is easily obtained by suppressing the annealing temperature to low levels (for example, about 900 to 1500° C.)

The reactivity of a carbon nanotube tends to be improved in the case where a carbon nanotube has a rough surface having many irregularities and wrinkles and rich in impurities and metals, in the case where crystallinity is low and in the case where fibers are not aligned in a uniform direction. Such different surface characteristics are also obtained by varying the manufacturing method. More specifically, if the surface of a carbon nanotube is annealed at a low temperature (for example, about 900 to 1500° C.), defects tend to be produced. In the carbon nanotube having many defects, since it has a surface having many irregularities and possibly has a highly active surface state, introduction of a functional group into the carbon nanotube surface can be effectively performed by a surface treatment described later. In this embodiment, in consideration of these findings in combination with desired physical properties and application or the like of a surface-treated carbon nanotube, preferable conditions can be appropriately selected.

In obtaining both reactivity and strength of a carbon nanotube surface, it is preferable to use an intermediate carbon nanotube between a graphitized carbon nanotube and an ungraphitized carbon nanotube. In general, the intermediate carbon nanotube mentioned above can be obtained by controlling the annealing temperature of an ungraphitized carbon nanotube. Specifically, it is preferable to control the annealing temperature to about 1500 to 2500° C.

The carbon nanotube may be a branched carbon nanotube as long as a strong aggregate (aggregate formed of densely entangled fibers) is not formed within the effect of the embodiment. The degree of branching of the carbon nanotube before a surface treatment is preferably low. Specifically, in view of this, the number of fibers branched from a single fiber is preferably 5 or less and more preferably 3 or less.

The outer diameter of a carbon nanotube fiber before a surface treatment is preferably 10 to 500 nm, more preferably 10 to 300 nm and further preferably 10 to 200 nm. If the fiber outer diameter is 10 nm or more, the cohesive force between fibers can be appropriately suppressed. As a result, dispersibility of the carbon nanotube when the carbon nanotube is mixed with a resin can be further improved and carbon nanotubes come to be easily entangled. In contrast, if the fiber outer diameter is 500 nm or less, carbon nanotubes are easily detangled. As a result, the dispersibility of the carbon nanotube when the carbon nanotube is kneaded with a resin can be improved.

Provided that the length of a carbon nanotube before a surface treatment is represented by L and the diameter by D, the ratio of the length to the diameter (L/D ratio:aspect ratio) is preferably 20 to 1000, more preferably 20 to 800 and further preferably 20 to 500. If the L/D ratio is 20 or more, the fiber length becomes appropriately long, entangling between carbon nanotube fibers is facilitated, with the result that the tensile strength at high temperature tends to improve when the carbon nanotube is mixed with a resin. In contrast, if the L/D ratio is 1000 or less, carbon nanotube fibers are not excessively coagulated and the dispersibility of the carbon nanotube tends to improve when the carbon nanotube is kneaded with a resin.

The surface oxygen concentration of a carbon nanotube before a surface treatment and measured by X-ray photoelectron spectroscopy is preferably 0.1 to 1.0 atm %, more preferably 0.1 to 0.8 atm % and further preferably 0.1 to 0.5 atm %. If the surface oxygen concentration falls within the above range, the number of reactive sites of the carbon nanotube increases and a larger number of functional groups can be introduced by the surface treatment described later. As a result, the effect of the embodiment is more significantly produced. The reason for this is unknown; however, it is conceivably because the lower the surface oxygen concentration, the higher the crystallinity of the carbon nanotube. It is also conceivable that the crystalline carbon nanotube has good compatibility particularly with an organic acid (described later) such as maleic anhydride and a polymer (described later) having an organic acid as a polymerization unit (however, the function of the embodiment is not limited to this).

The thermal reduction amount of a carbon nanotube before a surface treatment at 600° C. in a nitrogen atmosphere is preferably 3.0% or less, more preferably 1.0% or less and further preferably 0.5% or less. The thermal reduction amount refers to the weight loss at 600° C. measured after temperature is raised from 30° C. to 600° C. in a nitrogen atmosphere (flow rate: 250 mL/minute) at a temperature raising rate of 10° C./minute. If the thermal reduction amount is 3.0% or less, the purity of a carbon nanotube increases. Therefore, it is considered that a larger number of functional groups can be introduced into not impurities but a carbon nanotube itself by a surface treatment described later.

In the Raman scattering spectrum of a carbon nanotube before a surface treatment, the ratio (Id/Ig) of the peak area (Id) of the band having the range of 1335 to 1365 $cm^{-1}$ to the peak area (Ig) of the band having the range of 1565 to 1600 $cm^{-1}$ is preferably 0.1 to 2.8, more preferably 0.1 to 2.5 and further preferably 0.1 to 2.0.

(Surface-Treated Carbon Nanotube)

The thermal reduction amount of the surface-treated carbon nanotube of the embodiment at 600° C. in a nitrogen atmosphere is 0.2 to 40%, preferably 0.5 to 40%, more preferably 0.8 to 40%, further preferably 2.1 to 40%, still further preferably 5 to 40% and further more preferably 10 to 40%. The larger the thermal reduction amount, the larger the number of functional groups bound to or deposited on the carbon nanotube tends to be. In other words, a sufficient number of functional groups are introduced. Examples of substances which are vaporized (sublimated) at 600° C. include (i) a functional group (hereinafter, referred to as a "bound substance") derived from a surface treatment agent (a compound used for a surface treatment of a raw-material carbon nanotube; described later) and bound to a carbon nanotube through the reaction between a carbon nanotube and the surface treatment agent and (ii) a functional group (hereinafter, referred to as "deposit") derived from a surface treatment agent (and/or a substance derived from the surface treatment agent) and deposited on a carbon nanotube in a certain state not via a chemical reaction between a carbon nanotube and the surface treatment agent but via a certain attraction force (e.g., gravity).

The present inventors found that the thermal reduction amount of a surface-treated carbon nanotube at 600° C. serves as an index showing the proportion of a bound substance and a deposit in a surface-treated carbon nanotube. The larger the thermal reduction amount at 600° C., the more the bound substance and deposit are presumably present, indicating that the larger the thermal reduction amount, the more the functional groups capable of binding to a resin are present, and the affinity of the surface-treated carbon nanotube for a resin tends to improve. To describe more specifically, if the thermal reduction amount is less than 0.2%, the amount of bound substance and deposit is low and thus affinity for a resin is low (however, the function is not limited to this). Note that the amount of bound substance and deposit tends to be increased by allowing, for example, a surface treatment agent to react, in the absence of a solvent. Furthermore, the amount of deposit tends to be increased by using a non-polar solvent as a washing solvent described later.

The surface oxygen concentration of the surface-treated carbon nanotube of the embodiment measured by X-ray photoelectron spectroscopy (XPS) is 1.5 to 40 atm %, preferably 2 to 40 atm %, more preferably 5 to 40 atm %, further preferably 10 to 40 atm % and still further preferably 20 to 40 atm %. The present inventors found that the surface oxygen concentration of a surface-treated carbon nanotube serves as an index indicating how large number of functional groups is introduced into the carbon nanotube surface. If the surface oxygen concentration is less than 1.5%, a sufficient number of functional groups cannot be introduced into the carbon nanotube surface, and sufficient addition effect cannot be obtained when the carbon nanotube is mixed with a resin. If the surface oxygen concentration exceeds 40%, the carbon nanotube becomes fragile or turns into gel when kneaded with a resin (however, the function is not limited to this).

The surface sulfur concentration of the surface-treated carbon nanotube of the embodiment is less than 0.1 atm % and preferably 0 atm %. If the surface sulfur concentration is 0.1 atm % or more, sulfur remaining in the carbon nanotube cuts the molecular chain of the resin to be mixed to reduce the molecular weight of the resin. In contrast, if the surface sulfur concentration is 0.1 atm % or more, for example, a screw used in kneading with a resin is abraded away and corrosion of metal parts tends to occur. The surface sulfur concentration can be obtained by X-ray photoelectron spectroscopy (XPS), more specifically, can be calculated by the method described in Examples.

If the thermal reduction amount, surface oxygen concentration and surface sulfur concentration of a surface-treated carbon nanotube fall within the above respective ranges, the surface-treated carbon nanotube is excellent in dispersibility to a resin. In addition, when the surface-treated carbon nanotube is mixed with a resin into a composite material, breakage of the molecular chain of the resin can be prevented. As a result, the composite material can be provided with excellent strength and toughness not only at normal temperature but also at high temperature.

In the Raman scattering spectrum of the surface-treated carbon nanotube of the embodiment, the ratio (Id/Ig) of the peak area (Id) of the band having the range of 1335 to 1365 $cm^{-1}$ to the peak area (Ig) of the band having the range of 1565 to 1600 $cm^{-1}$ is preferably 0.1 to 2.8, more preferably 0.1 to 2.5 and further preferably 0.1 to 2.0.

Note that, although described later, it is preferable to control the surface-treated carbon nanotube of the embodiment so as to have a more suitable ratio (Id/Ig) depending upon the surface treatment agent (an inorganic acid, an organic acid, a polymer having an organic acid as a polymerization unit, etc.) to be used. If the ratio is further controlled in such a way, the surface state of the surface-treated carbon nanotube can be improved more suitably and the effect of the embodiment can be further improved.

The outer diameter of the surface-treated carbon nanotube fiber of the embodiment is preferably 10 to 500 nm, more preferably 10 to 300 nm and further preferably 10 to 200 nm. If the fiber outer diameter is 10 nm or more, the cohesive force between fibers can be properly controlled. As a result, the dispersibility of the carbon nanotube when the carbon nanotube is mixed with a resin can be further improved and carbon nanotubes are easily entangled. In contrast, if the fiber outer diameter is 500 nm or less, carbon nanotubes become easily detangled and the dispersibility of the carbon nanotube when the carbon nanotube is kneaded with a resin can be improved.

Provided that the length of the surface-treated carbon nanotube of the embodiment is represented by L and the diameter by D, the L/D ratio (aspect ratio) is preferably 20 to 1000, more preferably 20 to 800 and further preferably 20 to 500. If the L/D ratio is 20 or more, the fiber length becomes appropriately long, entangling between carbon nanotube fibers is facilitated, with the result that tensile strength of the composite material mentioned above at high temperature can be further improved. In contrast, if the L/D ratio is 1000 or less, carbon nanotube fibers are not excessively coagulated, with the result that dispersibility of the carbon nanotube when the carbon nanotube is kneaded with a resin can be improved.

Note that to improve the dispersibility of a carbon nanotube to a resin, if large shearing force is applied when a surface-treated carbon nanotube is kneaded with a resin, the structure of a carbon nanotube fiber aggregate is broken and the carbon nanotube can be dispersed/diffused in the resin; however the L/D ratio of the carbon nanotube tends to reduce. For this reason, in order to effectively obtain desired physical properties, it is preferable to keep the aspect ratio within the above range.

(Surface Treatment)

As the reaction for introducing a functional group into the surface of a carbon nanotube and performed as a surface treatment, examples include an ionic reaction, a radical reaction and a pericyclic reaction. The ionic reaction refers to a chemical reaction in which one of chemical species donates an electron pair to generate a new binding orbital and the direction for proceeding the reaction is controlled by charge bias between atoms, i.e., depending upon whether an atom has an electron-accepting property or an electron-donating property. The radical reaction refers to a chemical reaction in which two chemical species each donate a single electron to generate a new binding orbital. The pericyclic reaction refers to a chemical reaction in which the π orbit of chemical species is converted into the σ orbit via a cyclic transition state to generate a new bond at two or more sites. The conditions of the surface treatment can be appropriately selected depending upon the type of reaction, etc.

The reaction temperature of the surface treatment varies depending upon the type of reaction to be employed and the composition ratio; however, the reaction temperature is preferably 80 to 200° C., more preferably 85 to 180° C. and further preferably 90 to 180° C. When a substance to be used in the surface treatment is solid, powder or paste at a reaction temperature, it is preferable that the substance is reacted in a liquid phase using a solvent. In the surface treatment, a solvent can be used in order to improve flowability or simplify a reaction operation.

The pressure of the surface treatment reaction is not particularly limited and the reaction can be performed under vacuum, under an atmospheric pressure or under pressure. If the reaction is performed at a temperature of a boiling point or less, the reaction is generally performed under an atmospheric pressure. If the reaction is performed at a temperature of a boiling point or more, the reaction is preferably performed under pressure.

The time of the surface treatment reaction varies depending upon e.g., the type of reaction, the component composition to be employed, the reactor, temperature and pressure; however, the reaction time is preferably 0.5 to 36 hours, more preferably 2 to 24 hours and further preferably 3 to 24 hours. If the reaction time falls within the range of 0.5 to 36 hours, introduction of a functional group into a carbon nanotube can be further improved with satisfactory productivity. The reaction conditions (reaction temperature, time, pressure, etc.) for the surface treatment can be appropriately selected depending upon the object of the embodiment.

As the reactors to be used in individual reactions of the embodiment, known reactors can be used. For example, reactors conventionally known, which include a mixing vessel, a pressurizing mixing vessel, a reduced pressure mixing vessel, a column reactor, a distillation tower, a packed tower and a thin-film distillation tower, can be appropriately used in combination. As the material for a reactor, known materials known can be used. For example, a glass reactor, a stainless steel reactor, a carbon steel reactor, a Hastelloy reactor, a glass-lining reactor and a fluorine resin coated reactor can be used. Depending upon the step and conditions, corrosion with acid significantly may occur. In such a case, it is preferable to appropriately select a glass reactor, a glass-lining reactor, a fluorine resin coated reactor, a Hastelloy reactor, etc.

In the embodiment, the compound to be used in a surface treatment of a raw-material carbon nanotube is not particularly limited. Preferably, at least one selected from the group consisting of an inorganic acid, an organic acid and a polymer having an organic acid as a polymerization unit (hereinafter, sometimes simply referred to as a "polymer") is used for a surface treatment method. Specifically, an inorganic acid, an organic acid or a polymer is directly added to the carbon nanotube and stirred to perform the surface treatment reaction of a carbon nanotube. Alternatively, a raw-material carbon nanotube is dispersed in a solvent to obtain a solution and then an inorganic acid or an organic acid may be added to the solution to perform the surface treatment reaction of a carbon nanotube. After the reaction, a post treatment such as filtration and dehydration may be performed as necessary.

The inorganic acid to be used in the surface treatment refers to an acid containing a non-metal atom other than a carbon atom, such as a chlorine atom, a sulfur atom, a nitrogen atom and a phosphorus atom. Examples of the inorganic acid include hydrochloric acid, nitric acid, phosphoric acid, sulfuric acid, boric acid, hydrofluoric acid, hydrogen peroxide, perphosphoric acid, persulfuric acid and peroxo-perchloric acid. Of them, at least one selected from the group consisting of phosphoric acid, hydrogen peroxide and acetic acid is preferred and hydrogen peroxide is more preferred since they have satisfactory interaction with a resin such as a polyamide.

When an inorganic acid is used, in view of compatibility with a surface treatment reaction, an amorphous carbon nanotube is rather preferably used. When at least an inorganic acid is used in the surface treatment, the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum of a surface-treated carbon nanotube is preferably 1.0 to 2.0, more preferably 1.1 to 1.7 and further preferably 1.2 to 1.5. In this case, hydrogen peroxide is preferably used as an inorganic acid. If hydrogen peroxide is used and the ratio (Id/Ig) of the surface-treated carbon nanotube is controlled to fall within the above range, a further excellent effect of the embodiment will be produced.

The organic acid to be used in a surface treatment refers to any acid as long as the acid is an organic compound. Examples of the organic acid include sulfonic acid, citric acid, oxalic acid, formic acid, acetic acid, acrylic acid, diacrylic acid, methacrylic acid, crotonic acid, isocrotonic acid, cinnamic acid, maleic acid, fumaric acid, dimethyl fumaric acid, itaconic acid, citraconic acid, anhydrous percarbonic acid, peracetic acid, perbenzoic acid and anhydrides of these. Examples of the anhydrides include a fumaric anhydride, a maleic anhydride, a benzoic anhydride and an acetic anhydride. Of them, at least one selected from the group consisting of citric acid, oxalic acid, acrylic acid, diacrylic acid, methacrylic acid, maleic acid, fumaric acid, dimethyl fumaric acid, itaconic acid, citraconic acid, a fumaric anhydride, a maleic anhydride, benzoic anhydride and an acetic anhydride, in view of satisfactory interaction with a resin such as a polyamide. Of them, it is more preferable to use at least a maleic anhydride and further preferable that a maleic anhydride alone is used.

Examples of the polymer having an organic acid as a polymerization unit for use in the surface treatment include a copolymer of a maleic anhydride such as a styrene-maleic anhydride copolymer, an ethylene-maleic anhydride copolymer, a n-butene-maleic anhydride copolymer, an isobutene-maleic anhydride copolymer, a benzene-maleic anhydride copolymer, a 2-methyl-1-butene-maleic anhydride copolymer, a 4-methyl-1-benzene-maleic anhydride copolymer, a 1,3-heptadiene-maleic anhydride copolymer and a trimethyl benzene-maleic anhydride copolymer. Other than these, examples include copolymers obtained by copolymerizing at least two selected from the group consisting of sulfonic acid, citric acid, oxalic acid, formic acid, acetic acid, acrylic acid, diacrylic acid, methacrylic acid, crotonic acid, isocrotonic acid, cinnamic acid, maleic acid, fumaric acid, dimethyl fumaric acid, itaconic acid and citraconic acid. Of them, in view of satisfactory interaction with a resin such as a polyamide, at least one selected from the group consisting of a poly(acrylic acid), poly(acrylic acid-comaleic acid) copolymer, an ethylene-maleic anhydride copolymer and a styrene-maleic anhydride copolymer, is preferred.

When an organic acid or a polymer having an organic acid as a polymerization unit is used, in view of compatibility with a surface treatment reaction, a crystalline carbon nanotube is rather preferably used. Accordingly, when at least an organic acid or an a polymer having an organic acid as a polymerization unit is used in the surface treatment, the ratio (Id/Ig) of the peak area (Id) of the band having the range of 1335 to 1365 $cm^{-1}$ to the peak area (Ig) of the band having the range of 1565 to 1600 $cm^{-1}$ in the Raman scattering spectrum of a surface-treated carbon nanotube, is preferably 0.1 to 0.9, more preferably 0.1 to 0.5 and further preferably 0.1 to 0.3. In this case, a maleic anhydride is preferred as the organic acid and a poly(acrylic acid-co-maleic acid) copolymer, an ethylene-maleic anhydride copolymer or a styrene-maleic anhydride copolymer is preferred as the polymer having an organic acid as a polymerization unit. If these are used and the ratio (Id/Ig) of the surface-treated carbon nanotube is controlled to fall within the above range, a further excellent effect of the embodiment will be produced.

As the aforementioned inorganic acid, organic acid and polymer having an organic acid as a polymerization unit, in view of reactivity between a surface-treated carbon nanotube and a resin to be mixed, at least one selected from the group consisting of hydrogen peroxide, citric acid, oxalic acid, acrylic acid, diacrylic acid, methacrylic acid, maleic acid, fumaric acid, dimethyl fumaric acid, itaconic acid, citraconic acid, a fumaric anhydride, a maleic anhydride, a benzoic anhydride, an acetic anhydride, a poly(acrylic acid), a poly(acrylic acid-co-maleic acid) copolymer, an ethylene-maleic anhydride copolymer and a styrene-maleic anhydride copolymer, is preferred. Of them, a maleic anhydride and an ethylene-maleic anhydride copolymer are more preferred. If these are used, it is possible to introduce many functional groups into the surface of a carbon nanotube; however, the effect of few surface fractures by a reaction step and the effect of lowering a reduction of the molecular weight of the resin to be mixed are more significantly exerted. Note that these effects, as are described later, can be more significantly obtained by applying a surface treatment in a liquid phase and in the absence of a solvent.

When a solvent is used for dispersing a raw-material carbon nanotube in a surface treatment reaction, the type of solvent is not particularly limited. An aqueous solvent or a non-aqueous solvent may be used. Examples of the aqueous solvent include water and distilled water. Examples of the non-aqueous solvent include aliphatic hydrocarbon solvents such as hexane; aromatic solvents such as toluene, xylene, dimethylbenzene, trimethylbenzene, pyridine, methylnaphthalene, methylene chloride, chloroform, chlorobenzene and dichlorobenzene; ether solvents such as dioxane, tetrahydrofuran and methylcellosolve; acetone solvents such as ethoxyethanol, methoxyethoxyethanol, methyl acetate, ethyl acetate and acetone; acetone solvents such as cyclohexanone and methylethylketone; alcohol solvents such as methyl alcohol, ethyl alcohol, isopropyl alcohol, butyl alcohol, ethylene glycol, poly(ethylene glycol) and phenol; acetic acid, triethylamine, trimethanolamine, acrylonitrile, octadecylamine, aniline, N,N-dimethylformamide, dimethylacetamide, nitromethane, 1-methyl-2-pyrrolidone and dimethylsulfoxide. Of them, at least one selected from the group consisting of water, an alcohol solvent, a toluene solvent, an acetone solvent, an ether solvent and the absence of solvent is preferred.

A solvent may be used for dispersing a carbon nanotube; however, it is preferable that e.g., an inorganic acid, an organic acid and a polymer having an organic acid as a polymerization unit each are preferably reacted in the absence of a solvent. The reactivity of a surface treatment agent with a carbon nanotube is improved and more functional groups tend to be introduced by not using a solvent. Particularly, when a surface treatment is performed using at least maleic anhydride, the surface treatment is preferably performed in the absence of a solvent. The surface-treated carbon nanotubes containing compounds represented by formula (1) to formula (4) and compounds represented by formula (5) and (6) described later can be expected to be more effectively obtained at least by not using a solvent.

When a radical reaction is employed as the aforementioned reaction for introducing a functional group into the surface of a carbon nanotube, examples include a reaction of grafting the functional group to the main chain of a carbon nanotube. The radical initiator to be used in such a radical reaction is not particularly limited; however, in view of facilitating the radical reaction, an initiator that can generate radicals in mild reaction conditions is preferred. Preferable examples thereof include peroxide initiators and azo initiators, i.e., disulfide compounds such as tetramethylthiuram disulfide.

Specific examples of the peroxide initiators include diisobutyl peroxide, cumyl-peroxyneodecanoate, di-n-propyl-peroxydicarbonate, diisopropyl-peroxydicarbonate, di-sec-butyl-peroxydicarbonate, 1,1,3,3-tetramethylbutyl-peroxyneodecanoate, di-(4-t-butylcyclohexyl) peroxydicarbonate, 1-cyclohexyl-1-methylethylperoxyneodecanoate, di(2-ethoxyethyl) peroxydicarbonate, di(2-ethylhexyl)peroxydicarbonate, t-hexyl-peroxyneodecanoate, dimethoxybutyl-peroxydicarbonate, t-butyl-peroxyneodecanoate, t-hexyl-peroxypivalate, t-butyl-peroxypivalate, di(3,3,5-trimethylhexanoyl)peroxide, di-n-octanoyl peroxide, dilauroyl peroxide, distearoyl peroxide, 1,1,3,3-tetramethylbutylperoxy-2-ethylhexanoate, disuccinic acid peroxide, 2,5-dimethyl-2,5-di(2-ethylhexanoylperoxy)hexane, t-hexylperoxy-2-ethylhexanoate, di(4-methylbenzoyl)peroxide, t-butylperoxy-2-ethylhexanoate, di(3-methylbenzoyl)peroxide, benzoyl(3-methylbenzoyl)peroxide, dibenzoyl peroxide, t-butyl peroxyisobutyrate, 1,1,1-di(t-butylperoxy)-2-methylcyclohexane, 1,1-di(t-hexylperoxy)-3,3,5-trimethylcyclohexane, 1,1-di(t-hexylperoxy)cyclohexane, 1,1-di(t-hexylperoxy)-3,3,5-trimethylcyclohexane, 1,1-di(t-butylperoxy)cyclohexane, 2,2-di(4,4-di-(t-butylperoxy)cyclohexyl)propane, t-hexyl peroxyisopropylmonocarbonate, t-butylperoxymaleic acid, t-butylperoxy-3,3,5-trimethylhexanoate, t-butylperoxylaurate, 2,5-dimethyl-2,5-di-(3-methylbenzoylperoxy)hexane, t-butylperoxyisopropylmonocarbonate, t-butylperoxy-2-ethylhexylmonocarbonate, t-hexyl peroxybenzoate, 2,5-dimethyl-2,5-di-(benzoylperoxy)hexane, t-butyl peroxyacetate, 2,2-di-(t-butylperoxy)butane, t-butyl peroxybenzoate, n-butyl-4,4-di-(t-butylperoxy)valerate, di(2-t-butylperoxyisopropyl)benzene, dicumyl peroxide, di-t-hexyl peroxide, 2,5-dimethyl-2,5-di(t-butylperoxy)hexane, t-butylcumyl peroxide, di-t-butyl peroxide, p-menthane hydroperoxide, 2,5-dimethyl-2,5-di-(t-butylperoxy)hexyne-3, diisopropylbenzene hydroperoxide, 1,1,3,3-tetramethylbutyl hydroperoxide, cumene hydroperoxide, t-butyl hydroperoxide, t-butyltrimethylsilyl peroxide, 2,3-di-methyl-2,3-diphenylbutane, 1,1-bis(t-butylperoxy)-3,3,5-trimethylcyclohexane and 1,1-bis(t-butylperoxy)cyclohexane.

Specific examples of the azo initiators include azobisisobutyronitrile, azobisisovaleronitrile, 1,1-azobis(1-cyclohexanecarbonitrile), 2-2'-azobis(4-methoxy-2,4-dimethylvaleronitrile), 2-2'-azobis(2,4-dimethylvaleronitrile), 2-2'-azobisisobutyronitrile, 2-2'-azobis(2-methylbutyronitrile), 1-1'-azobis(cyclohexane-1-carbonitrile), 1-[(1-cyano-1-methylethyl)azo]formamide, 2-2'-azobis{2-methyl-N-[1,1-bis(hydroxymethyl)-2-hydroxyethyl]propionamide}, 2-2'-azobis{2-methyl-N-[2-(1-hydroxybutyl)]-propionamide}, 2-2'-azobis[2-methyl-N-(2-hydroxyethyl)-propionamide], 2-2'-azobis(N-butyl-2-methylpropionamide), 2-2'-azobis(N-cyclohexyl-2-methylpropionamide), 2-2'-azobis[2-(5-methyl-2-imidazolin-2-yl)-propane]dihydrochloride, 2-2'-azobis[2-(2-imidazolin-2-yl)propane]dihydrochloride, 2-2'-azobis[2-(2-imidazolin-2-yl)propane]disulfate dihydrate, 2-2'-azobis[2-(3,4,5,6-tetrahydropyrimidin-2-yl)propane]dihydrochloride, 2-2'-azobis{2-[1-(2-hydroxyethyl)-2-imidazolin-2-yl]propane}dihydrochloride, 2-2'-azobis[2-(2-imidazolin-2-yl)propane], 2-2'-azobis(2-methylpropioneamidine) dihydrochloride, 2-2'-azobis[N-(2-carboxyethyl)-2-methylpropioneamidine], 2-2'-azobis(2-methylpropionamideoxime), dimethyl-2-2'-azobis(2-methylpropionate), 4-4'-azobis(4-cyanovaleric acid) and 2-2'-azobis(2,2,4-trimethylpentane).

To disperse a carbon nanotube homogeneously in a solvent, an ultrasonic dispersion method or ball milling method can be used. Specific examples include a method of homogeneously dispersing a carbon nanotube in a solvent by driving a sonicator having a vibration number of 20 to 50 kHz and a power of 50 to 3000 W for 30 minutes to 60 hours, which are determined depending upon e.g., the volume of carbon nanotube and an amount of a solvent.

In the embodiment, a surface treatment reaction of a raw-material carbon nanotube is preferably performed in a liquid phase. "The surface treatment is performed in a liquid phase" herein means that the surface treatment is performed in a liquid state. Thus, for example, a surface treatment by an oxidation reaction in a gaseous phase (gas-phase oxidation) is not included in the above surface treatment. By performing a surface treatment of a carbon nanotube in a liquid phase, the occurrence of surface fracture of the carbon nanotube can be further reduced. When the carbon nanotube is mixed with a resin to form a composite material, the addition effect of the carbon nanotube can be further improved. In addition, extrudability during molding can be further improved. Furthermore, since the reaction is performed in a liquid phase, usually, the surface treatment can be performed in mild reaction conditions and a large-scale apparatus is not required. This is advantageous in view of a process.

As the surface treatment method performed in a liquid phase, for example, a method of using a treatment agent which is liquid at normal temperature and normal pressure, a method of using a treatment agent which is previously changed into a liquid state by heating, and a method of using a treatment agent which is previously changed into a liquid state by use of a solvent, can be employed. Accordingly, even if a treatment agent is, e.g., solid at normal temperature and normal pressure, it can be used by changing it into a solution by use of a solvent or changing it into a solution by heating it. Note that when a treatment agent which is liquid at normal temperature and normal pressure and a treatment agent which is previously changed into a liquid state, i.e., solution by heating it are used, a solvent may or may not be used. If a solvent is not used, a surface treatment is performed in a liquid phase and in the absence of a solvent. A surface treatment performed in a liquid phase and in the absence of a solvent is more preferred because the reactivity with a carbon nanotube is improved.

As the inorganic acids that can be used in a liquid phase reaction, e.g., phosphoric acid, hydrogen peroxide and acetic acid are preferred. As the organic acid that can be used in the liquid phase reaction, e.g., citric acid, oxalic acid, acrylic acid, diacrylic acid, methacrylic acid, maleic acid, fumaric acid, dimethyl fumaric acid, itaconic acid, citraconic acid, a fumaric anhydride, a maleic anhydride, a benzoic anhydride and an acetic anhydride are preferable. Of them, at least a maleic anhydride is preferably used.

As the polymer having an organic acid as a polymerization unit that can be used in the liquid phase reaction, e.g., poly(acrylic acid), poly(acrylic acid-co-maleic acid), ethylene-maleic anhydride and styrene-maleic anhydride are preferable. When the surface treatment of a carbon nanotube is performed by using each of these, a solvent can be used; however, the treatment is preferably performed in the absence of a solvent, in view of reactivity. More specifically, the surface treatment of a carbon nanotube is preferably performed by heating each of these into a molten state. Needless to say, in the case of a polymer having a considerably high melting point, the polymer can be dissolved in a solvent and used as a solution.

The surface treatment using a maleic anhydride will be more specifically described by way of example. As the surface treatment conditions using a maleic anhydride, preferable conditions can be appropriately selected depending upon the type of reaction employed and the composition ratio. For example, when a radical reaction is performed as a surface treatment reaction, the reaction temperature is preferably 80 to 190° C., more preferably 100 to 180° C. and further preferably 120 to 180° C. In contrast, when Diels-Alder reaction, which is one of the pericyclic reactions, is performed as a surface treatment reaction and by using a maleic anhydride, its reaction temperature, although it is not particularly limited, is estimated as preferably 80 to 250° C., more preferably 100 to 230° C. and further preferably 160 to 230° C.

The surface treatment using a maleic anhydride can be performed under any reaction pressure conditions, e.g., under vacuum, under an atmospheric pressure and under pressure. If the reaction is performed at a temperature of a boiling point or less, the reaction is generally performed under an atmospheric pressure; whereas if the reaction is performed at a temperature of boiling point or more, the reaction is preferably performed under pressure.

The reaction time of the surface treatment using a maleic anhydride varies depending upon the reaction conditions, etc.; however, the reaction time is preferably 0.5 to 36 hours, more preferably 2 to 24 hours and further preferably 3 to 24 hours.

The post treatment performed after the surface treatment will be described. After the surface treatment, a reaction product can be filtered, washed and dried as necessary. For example, a method for washing a reaction product is not particularly limited. For example, a method of washing a reaction product of the surface treatment reaction with a solvent after filtration and a method of washing the residue with a solvent while filtering under aspiration can be employed. The number of washing times is not particularly limited and can be controlled depending upon e.g., the volume and the yield of the surface-treated carbon nanotube. Usually, washing is made 1 to 20 times. After washing, the washed residue is dried to obtain a surface-treated carbon nanotube.

The washing solvent is not particularly limited and an aqueous solvent or a non-aqueous solvent may be used. Examples of the aqueous solvent include water such as pure water and distilled water. Examples of the non-aqueous solvent include aliphatic hydrocarbon solvents such as hexane; aromatic solvents such as toluene, xylene, dimethylbenzene, trimethylbenzene, pyridine, methylnaphthalene, methylene chloride, chloroform, chlorobenzene, and dichlorobenzene; ether solvents such as dioxane, tetrahydrofuran, and methylcellosolve; acetone solvents such as ethoxyethanol, methoxyethoxyethanol, methyl acetate, ethyl acetate and acetone; ketone solvents such as cyclohexanone and methylethylketone; alcohol solvents such as methyl alcohol, ethyl alcohol, isopropyl alcohol, butyl alcohol, ethylene glycol, polyethylene glycol and phenol; acetic acid, triethylamine, trimethanolamine, acrylonitrile, octadecylamine, aniline, N,N-dimethylformamide, dimethylacetamide, nitromethane, 1-methyl-2-pyrrolidone and dimethylsulfoxide.

Of them, as the washing solvent, one solvent selected from the group consisting of water, toluene, an ether solvent, an acetone solvent and an alcohol solvent. Furthermore, if a large amount of treatment is desired to remain on the surface of a carbon nanotube (for example, both bound substance and deposit are desired to remain), washing with a non-polar solvent (toluene, etc.) is preferred; whereas if only a substance (bound substance) strongly bound to a carbon nanotube is desired to remain, washing with a polar solvent (alcohol solvent, etc.) is preferred.

Since the surface-treated carbon nanotube of the embodiment has few surface fractures, the carbon nanotube has excellent adhesion to the resin to be blended. Because of this, it is expected that the physical properties of a composite material containing the surface-treated carbon nanotube and the resin are drastically improved. Furthermore, if surface fractures are few, e.g., peel-off of surface layer of the carbon nanotube can be effectively suppressed. Thus, it is expected that adhesion between the resin and the surface-treated carbon nanotube is improved. Also in this respect, drastic improvement in the physical properties of the composite material is expected.

Note that as an index for evaluating the degree of surface fracture by a surface treatment, examples include the Raman scattering spectrum of a carbon nanotube. Specifically, a spectrum having at least one peak top between 1565 and 1600 cm$^{-1}$ (hereinafter, referred to as "spectrum A"), which is derived from a graphite (also referred to as a "crystal") structure, is a spectrum that commonly emerges; whereas a spectrum having at least one peak top between 1335 and 1365 cm$^{-1}$ (hereinafter, referred to as "spectrum B") is a spectrum that is derived from a defect (referred to also as "amorphous structure") of a carbon nanotube. If a carbon nanotube has a point detect or a defective edge of a crystal, etc., the intensity of spectrum B increases. The intensity of spectrum B relative to spectrum A serves as a rough indication of the amount of defect.

Accordingly, if there is a large difference in the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum of a carbon nanotube between before and after the surface treatment, it is determined that the degree of the surface fracture is large by the difference. If the absolute value (ΔId/Ig) of the difference between the above ratios (Id/Ig) before and after the surface treatment is small, it is determined that the degree of the surface fracture in the surface treatment stage is small by the difference. In the surface-treated carbon nanotube of the embodiment, the above absolute value (ΔId/Ig) is small. Thus, a carbon nanotube having few surface fractures can be obtained. Note that, in the embodiment, examples of a method for reducing the above absolute value (ΔId/Ig) as much as possible include a method of using a milder surface treatment agent.

According to a preferable aspect of the surface-treated carbon nanotube of the embodiment, the absolute value (ΔId/Ig) of the difference between the above ratios (Id/Ig) before and after the surface treatment can be controlled to be 0 to 2.0, more preferably 0 to 1.0, further preferably 0 to 0.8 and still further preferably 0 to 0.5. If the absolute value (ΔId/Ig) of the difference between the above ratios (Id/Ig) falls within the above range, the surface fracture of a carbon nanotube by the reaction step can be more significantly suppressed.

Particularly, in view of preventing molecular weight reduction of a resin and further improving extrudability, it is preferable that a surface treatment is performed by use of at least one selected from the group consisting of the aforementioned inorganic acids, organic acids and polymers having an organic acid as a polymerization unit without using a strong acid. More specifically, a surface treatment is preferably performed by use of at least one selected from the group consisting of hydrogen peroxide, citric acid, oxalic acid, acrylic acid, diacrylic acid, methacrylic acid, maleic acid, fumaric acid, dimethylfumaric acid, itaconic acid, citraconic acid, a fumaric anhydride, a maleic anhydride, a benzoic anhydride, an acetic anhydride, a poly(acrylic acid), poly(acrylic acid-co-maleic acid), ethylene-maleic anhydride and styrene-maleic anhydride without using a strong acid. Note that the strong acid herein refers to, for example, sulfuric acid, nitric acid and hydrochloric acid.

If the surface treatment of a carbon nanotube is performed using a strong acid such as sulfuric acid and nitric acid, e.g., even if washing is carefully performed by increasing the number of washing times, a trace amount of strong acid remains on the surface of the carbon nanotube, with the result that cutting of the molecular chain of a resin, corrosion and abrasion of metal parts (screw, etc.) of an extruder, etc., may possibly occur. However, if the surface treatment is performed without using a strong acid as mentioned above, such problems can be extremely effectively suppressed.

Furthermore, the surface-treated carbon nanotube of the embodiment can be manufactured by the aforementioned methods, etc. Since the carbon nanotube to be used as a raw material is inexpensive, mass production can be made. This is preferable also from the industrial point of view.

According to a preferable aspect, the surface-treated carbon nanotube of the embodiment contains a compound represented by any one of formula (1) to formula (4):

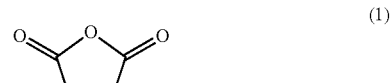

(1)

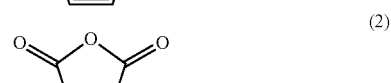

(2)

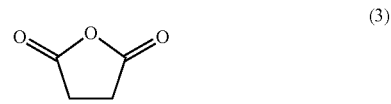

(3)

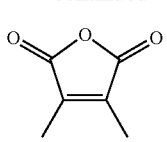
(4)

Since the surface-treated carbon nanotube of the embodiment contains at least a compound represented by any one of formula (1) to formula (4), the reactivity with and adhesion to a resin improve. Note that it is preferable that compounds represented by formula (1) to formula (4) chemically bind to the surface of a surface-treated carbon nanotube (correspond to a "bound substance" as described later). These compounds may be defined as maleic anhydrides or derivatives thereof. The substances chemically bound to the surface-treated carbon nanotube may be defined as "bound substances" whose functional groups are introduced into the carbon nanotube. Note that the presence of these can be confirmed after the surface treatment of a carbon nanotube by washing a deposit, the remaining surface treatment agent, etc., drying, and subjecting these to analysis by pyrolysis-gas chromatography/mass spectroscopy (Py-GC/MS), as described in detail later. Specifically, measurement can be made by the method described in Examples.

According to a further preferable aspect, the surface-treated carbon nanotube of the embodiment further contains a compound represented by formula (5) or formula (6). The compounds represented by formula (5) and formula (6) correspond to the "deposit" described later. If not only the compounds represented by formula (1) to formula (4) but also the compounds represented by formula (5) and formula (6) are contained, not only the strength and toughness at high temperature are further improved but also excellent strength and toughness can be obtained at normal temperature. The presence of compounds represented by formula (5) and formula (6) in the surface-treated carbon nanotube can be confirmed by $^{13}$C-NMR. Specifically measurement can be made by the method described in Examples.

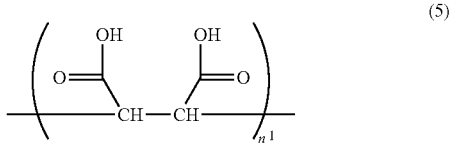
(5)

where $n^1$ is an integer of 2 to 400.

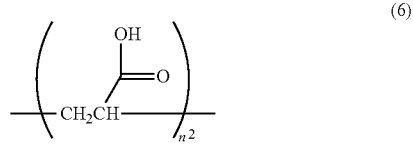
(6)

where $n^2$ is an integer of 2 to 650.

In formula (5), $n^1$ is 2 to 400, preferably 2 to 260, more preferably 2 to 130 and further preferably 2 to 70. If $n^1$ is 2 to 400, the strength of carbon nanotube fibers entangled with the resin to be mixed and toughness are improved.

In formula (6), $n^2$ is 2 to 650, preferably 2 to 350, more preferably 2 to 210 and further preferably 2 to 120. If $n^2$ is 2 to 650, the strength of carbon nanotube fibers entangled with the resin to be mixed and toughness are improved.

In the surface-treated carbon nanotube of the embodiment, the total content of the compound represented by any one of formula (1) to formula (4) is not particularly limited; however, the total content is preferably 0.1 to 40 mass %, more preferably 0.2 to 35 mass %, further preferably 0.3 to 30 mass %, still further preferably 0.4 to 25 mass % and further more preferably 0.5 to 20 mass %. The content of the compound mentioned above can be defined as the content of (i) bound substance of the substances: (i) bound substance and (ii) deposit, in the surface-treated carbon nanotube.

In the surface-treated carbon nanotube of the embodiment, the total content of a compound represented by formula (5) or formula (6) is not particularly limited; however, the content is preferably 0.5 to 40 mass %, more preferably 1 to 40 mass %, further preferably 2 to 37 mass %, still further preferably 5 to 35 mass % and further more preferably 10 to 35 wt %. The content of a compound represented by formula (5) or formula (6) can be defined as the content of the deposit in the surface-treated carbon nanotube.

When a surface treatment is performed under the atmospheric pressure, the longer the reaction time and the higher the reaction temperature, the larger the content of compounds represented by formula (1) to formula (4) and the content of compounds represented by formula (5) and formula (6) tends to be. In the surface-treated carbon nanotube, if the content of compounds represented by formula (1) to formula (4) and the content of compounds represented by formula (5) and formula (6) increase, the strength and toughness at high temperature tend to more improve, when the carbon nanotube is added to a resin or the like.

The compounds represented by formula (1) to formula (4) and compounds represented by formula (5) and formula (6) can be analyzed or quantified as follows.

The content of compounds represented by formula (1) to formula (4) and the content of compounds represented by formula (5) and formula (6) can be determined by determining the thermal reduction amount of a surface-treated carbon nanotube in a nitrogen atmosphere at 600° C. This is based on the finding of the present inventors that the thermal reduction amount of the surface-treated carbon nanotube in a nitrogen atmosphere at 600° C. can be used as an index showing the proportion of a bound substance and a deposit in the surface-treated carbon nanotube. In other words, the larger the thermal reduction amount at 600°, the larger the content of the aforementioned bound substance and deposit. In other words, the larger the thermal reduction amount at 600° C., the more the functional groups capable of binding to a resin are suggested to be present in a carbon nanotube. In such a surface-treated carbon nanotube, affinity for a resin tends to increase.

Examples of a substance vaporized (sublimated) at 600° C., include (i) the aforementioned bound substance (compounds represented by formula (1) to formula (4), etc.) and (ii) the aforementioned deposit (compounds represented by formula (5) and formula (6), etc.).

By washing a surface-treated carbon nanotube with a polar solvent such as methanol, deposit (compounds represented by formula (5) and formula (6), etc.) can be removed from the surface-treated carbon nanotube. Since the bound substance (compounds represented by formula (1) to formula (4), etc.) and the deposit (compounds represented by formula (5) and formula (6), etc.) can be separated in this manner, they can be separately quantified and analyzed.

For example, a surface-treated carbon nanotube is washed in methanol and filtered to separate the filtrate and the residue. The obtained residue is a surface-treated carbon nanotube from which deposit is washed away (a surface-treated carbon nanotube having only the bound substance). Accordingly, the carbon nanotube is analyzed by pyrolysis-gas chromatography/mass spectroscopy (Py-GC/MS) to detect the compounds represented by formula (1) to formula (4). Since the filtrate is obtained as a methanol solution of the deposit, the deposit can be taken out by removing methanol. The deposit is measured by NMR and GPC to detect compounds represented by formula (5) and formula (6).

(Resin Compositions, Etc.)

When the surface-treated carbon nanotube of the embodiment is mixed with a resin, excellent strength and toughness not only at normal temperature but also at high temperature can be imparted. Examples of the resin to be added include at least one selected from the group consisting of a thermoplastic resin, a thermosetting resin and a rubber component. Of them, a thermoplastic resin and a rubber component are preferred. Accordingly, in the embodiment, it is preferable to prepare a resin composition containing the aforementioned surface-treated carbon nanotube and a thermoplastic resin.

Examples of the thermoplastic resin include a polyethylene, a polypropylene, a polystyrene, an ABS resin, a polyacetal, a polyethylene terephthalate, a polybutylene terephthalate, a polyamide, a polycarbonate, a modified polyphenylene ether, a polyphenylene sulfide, a cycloolefin polymer, a liquid crystal polymer, a polyetherimide, a polysulfone, a polyethersulfone, a polyamideimide, a polyamide, a polyethylene, a thermoplastic polyimide, a polyether ketone, a polyetheretherketone, a fluororesin and a polybenzimidazole.

Examples of the thermosetting resin include an epoxy resin, a polyurethane, a phenol resin, a diarylphthalate resin, an unsaturated polyester resin, a urea resin, a melamine resin, a silicone resin, a polyimide resin and an arylester resin.

Examples of the rubber component include a natural rubber, a polybutadiene, a polyisoprene, a polyisobutylene, a neoprene, a polysulfide rubber, a Thiokol rubber, an acrylic rubber, a urethane rubber, a silicone rubber, an epichlorohydrin rubber, a styrene-butadiene block copolymer (SBR), a hydrogenated styrene-butadiene block copolymer (SEB), a styrene-butadiene-styrene block copolymer (SBS), a hydrogenated styrene-butadiene-styrene block copolymer (SEBS), a styrene-isoprene block copolymer (SIR), a hydrogenated styrene-isoprene block copolymer (SEP), a styrene-isoprene-styrene block copolymer (SIS), a hydrogenated styrene-isoprene-styrene block copolymer (SEPS), a styrene-butadiene random copolymer, a hydrogenated styrene-butadiene random copolymer, a styrene-ethylene-propylene random copolymer, a styrene-ethylene-butylene random copolymer, an ethylene-propylene copolymer (EPR), an ethylene-(1-butene)copolymer, an ethylene-(1-hexene)copolymer, an ethylene-(1-octene)copolymer, an ethylene-propylene-diene copolymer (EPDM), core-shell type rubbers such as siloxane-containing core-shell rubbers including a methyl methacrylate-butadiene-styrene-core shell rubber (MBS), a methyl methacrylate-butylacrylate-styrene-core shell rubber (MAS), an octyl acrylate-butadiene-styrene-core shell rubber (MABS), an alkyl acrylate-butadiene-acrylonitrile-styrene core-shell rubber (AABS), a butadiene-styrene-core shell rubber (SBR) and a methyl methacrylate-butylacrylate siloxane, a silicone elastomer, a nitrile elastomer, a butadiene elastomer, a urethane elastomer, a nylon elastomer, an ester elastomer, a fluorine elastomer and modified copolymers and elastomers obtained by introducing a reaction site (double bond, anhydrous carboxyl group, etc.) to these copolymers and elastomers.

Of them, for the reason that a surface-treated carbon nanotube exerts an excellent addition effect, a polyamide, a polyethylene, a polypropylene, a polystyrene, an ABS resin, a polyacetal, a polyethylene terephthalate, a polybutylene terephthalate, a polycarbonate, a modified polyphenylene ether, a polyphenylene sulfide, an epoxy resin, a polyurethane, a natural rubber, a polybutadiene, a polyisoprene, a polyisobutylene, a urethane rubber, a silicone rubber, a styrene-butadiene block copolymer (SBR), a hydrogenated styrene-butadiene block copolymer (SEB), a styrene-butadiene-styrene block copolymer (SBS), a hydrogenated styrene-butadiene-styrene block copolymer (SEBS), an ethylene-propylene-diene copolymer (EPDM) and a modified copolymer obtained by introducing an anhydrous carboxy group are preferred. Of them, a polyamide is more preferred as a thermoplastic resin.

(Polyamide)

Now, a polyamide (polyamide resin) will be more specifically described by way of example. The polyamide refers to a high molecular compound having a —CO—NH— bond (amide bond) in the main chain. Examples of the polyamide resin include, but are not particularly limited to, a polyamide obtained by condensation polymerization of a diamine and a dicarboxylic acid, a polyamide obtained by ring-opening polymerization of a lactam, a polyamide obtained by self-condensation of an ω-aminocarboxylic acid, and a copolymer obtained by copolymerization of two or more monomers constituting these polyamides. These polyamides may be used singly or in combinations of two or more.

Now, raw materials for polyamide resins will be described.

Examples of the diamine include an aliphatic diamine, an alicyclic diamine and an aromatic diamine.

Examples of the aliphatic diamine include linear saturated aliphatic diamines having 2 to 20 carbon atoms such as ethylenediamine, propylenediamine, tetramethylenediamine, pentamethylenediamine, hexamethylenediamine, heptamethylenediamine, octamethylenediamine, nonamethylenediamine, decamethylenediamine, undecamethylenediamine, dodecamethylenediamine and tridecamethylenediamine; and branched saturated aliphatic diamines having 3 to 20 carbon atoms such as 2-methylpentamethylenediamine (also referred to as 2-methyl-1,5-diaminopentane), 2,2,4-trimethylhexamethylenediamine, 2,4,4-trimethylhexamethylenediamine, 2-methyloctamethylenediamine and 2,4-dimethyloctamethylenediamine. Examples of the branched saturated aliphatic diamine include a diamine having a substituent and branched from the main chain.

Examples of the alicyclic diamine include 1,4-cyclohexanediamine, 1,3-cyclohexanediamine and 1,3-cyclopentanediamine.

Examples of the aromatic diamine include metaxylylenediamine, paraxylylenediamine, metaphenylenediamine, orthophenylenediamine and paraphenylendiamine.

Examples of the dicarboxylic acid include an aliphatic dicarboxylic acid, an alicyclic dicarboxylic acid and an aromatic dicarboxylic acid.

Examples of the aliphatic dicarboxylic acid include linear or branched saturated aliphatic dicarboxylic acids having 3 to 20 carbon atoms, such as malonic acid, dimethylmalonic acid, succinic acid, 2,2-dimethylsuccinic acid, 2,3-dimethylglutaric acid, 2,2-diethylsuccinic acid, 2,3-diethylglutaric acid, glutaric acid, 2,2-dimethylglutaric acid, adipic acid, 2-methyladipic acid, trimethyladipic acid, pimelic acid, suberic acid, azelaic acid, sebacic acid, dodecanedioic acid, tetradecanedioic acid, hexadecanedioic acid, octadecanedioic acid, eicosanedioic acid and diglycolic acid.

Examples of the alicyclic dicarboxylic acid include alicyclic carboxylic acids such as 1,4-cyclohexanedicarboxylic acid, 1,3-cyclohexanedicarboxylic acid and 1,3-cyclopentanedicarboxylic acid. The number of carbon atoms of the aliphatic ring of each of the alicyclic carboxylic acids is not particularly limited; however, the number of carbon atoms is preferably 3 to 10 and more preferably 5 to 10. Of them, in view of mechanical characteristic, 1,4-cyclohexanedicarboxylic acid is preferred.

The alicyclic dicarboxylic acid may be not substituted or may have a substituent. Examples of the substituent include alkyl groups having 1 to 4 carbon atoms such as a methyl group, an ethyl group, a n-propyl group, an isopropyl group, a n-butyl group, an isobutyl group and a tert-butyl group.

Examples of the aromatic dicarboxylic acid include aromatic dicarboxylic acids having 8 to 20 carbon atoms not substituted or substituted with a substituent. Examples of the substituent include alkyl groups having 1 to 6 carbon atoms, aryl groups having 6 to 12 carbon atoms, arylalkyl groups having 7 to 20 carbon atoms, halogen groups such as a chloro group and a bromo group, alkylsilyl groups having 3 to 10 carbon atoms, a sulfonic acid group and groups being salts thereof such as a sodium salt. Specific examples of the aromatic dicarboxylic acid include terephthalic acid, isophthalic acid, naphthalene dicarboxylic acid, 2-chloro terephthalate, 2-methyl terephthalate, 5-methyl isophthalate and 5-sodium sulfoisophthalate.

As long as the object of the embodiment is not damaged, a polyvalent carboxylic acid having a valence of 3 or more such as trimellitic acid, trimesic acid and pyromellitic acid may be further contained as the dicarboxylic acid. These may be used singly or in combinations of two or more.

Examples of the lactam include butyrolactam, pivalolactam, ε-caprolactam, caprylolactam, enantholactam, undecanolactam and laurolactam (dodecanolactam). Of them, in view of toughness, ε-caprolactam, laurolactam and the like are preferred, and ε-caprolactam is more preferred.

Examples of the aminocarboxylic acid include compounds obtained by opening the rings of the aforementioned lactams (ω-aminocarboxylic acid, α,ω-aminocarboxylic acid, etc.).

As the aminocarboxylic acid, a straight or branched saturated aliphatic carboxylic acid having 4 to 14 carbon atoms and substituted at the ω position with an amino group is preferred. Specific examples thereof include 6-aminocaproic acid, 11-aminoundecanoic acid and 12-aminododecanoic acid. Examples of the aminocarboxylic acid also include para-aminomethylbenzoic acid. Of them, in view of low water absorbing property, 12-aminododecanoic acid is preferred.

Specific examples of the polyamide resin include, but are not particularly limited to, polyamide 4 (polyα-pyrrolidone), polyamide 6 (polycaproamide), polyamide 11 (polyundecanamide), polyamide 12 (polydodecanamide), polyamide 46 (polytetramethylene adipamide), polyamide 56 (polypentamethylene adipamide), polyamide 66 (polyhexamethylene adipamide), polyamide 610 (polyhexamethylene sebacamide), polyamide 612 (polyhexamethylene dodecamide), polyamide 116 (polyundecamethylene adipamide), polyamide TMHT (trimethylhexamethylene terephthalamide), polyamide 6T (polyhexamethylene terephthalamide), polyamide 2Me-5T (poly2-methylpentamethylene terephthalamide), polyamide 9T (polynonamethylene terephthalamide), 2Me-8T (poly2-methyloctamethylene terephthalamide), polyamide 6I (polyhexamethylene isophthalamide), polyamide 6C (polyhexamethylene hexahydroterephthalamide), polyamide 2Me-5C (poly2-methylpentamethylene hexahydroterephthalamide), polyamide 9C (polynonamethylene hexahydroterephthalamide), 2Me-8C (poly2-methyloctamethylene hexahydroterephthalamide), polyamide PACM12 (polybis(4-aminocyclohexyl)methanedodecamide), polyamide dimethyl PACM12 (polybis(3-methyl-aminocyclohexyl)methanedodecamide, polyamide MXD6 (polymetaxylylene adipamide), polyamide 10T (polydecamethylene terephthalamide), polyamide 11T (polyundecamethylene terephthalamide), polyamide 12T (polydodecamethylene terephthalamide), polyamide 10C (polydecamethylene hexahydroterephthalamide), polyamide 11C (polyundecamethylene hexahydroterephthalamide) and polyamide 12C (polydodecamethylene hexahydroterephthalamide).

Of them, as the polyamide resin, polyamide 6 (polycaproamide), polyamide 66 (polyhexamethylene adipamide), polyamide 610 (polyhexamethylene sebacamide), polyamide 612 (polyhexamethylene dodecamide), polyamide 6T (polyhexamethylene terephthalamide), polyamide 2Me-5T (poly2-methylpentamethylene terephthalamide), polyamide 9T (polynonamethylene terephthalamide), 2Me-8T (poly2-methyloctamethylene terephthalamide), polyamide 6I (polyhexamethylene isophthalamide), polyamide 6C (polyhexamethylene hexahydroterephthalamide), polyamide 2Me-5C (poly2-methylpentamethylene hexahydroterephthalamide), polyamide 9C (polynonamethylene hexahydroterephthalamide), 2Me-8C (poly2-methyloctamethylene hexahydroterephthalamide) and polyamide 6I (polyhexamethylene isophthalamide) are preferred.

The polyamide resins may be polyamide copolymers obtained by copolymerizing two or more units constituting the aforementioned polyamides. Examples of polyamide copolymers include, but are not particularly limited to, polyamide 66/6I, polyamide 66/6T, polyamide 6T/2Me-5T, polyamide 9T/2Me-8T, polyamide 6C/2Me-5C and polyamide 9C/2Me-8C.

In polymerizing monomers of a polyamide, a terminal-blocking agent can be added in order to control the molecular weight. The terminal-blocking agent is not particularly limited and known terminal-blocking agents can be used.

Examples of the terminal-blocking agents include a monocarboxylic acid, a monoamine, an acid anhydride such as a phthalic anhydride, a monoisocyanate, a monoacid halide, a monoester and a monoalcohol. Of them, in view of thermal stability of a polyamide resin, a monocarboxylic acid and a monoamine are preferred. These may be used singly or in combinations of two or more.

The monocarboxylic acid that can be used as a terminal-blocking agent is not particularly limited as long as it has reactivity with an amino group. Examples thereof include aliphatic monocarboxylic acids such as formic acid, acetic acid, propionic acid, butyric acid, valeric acid, caproic acid, caprylic acid, lauric acid, tridecylic acid, myristic acid, palmitic acid, stearic acid, pivalic acid and isobutyric acid; alicyclic monocarboxylic acids such as cyclohexanecarboxylic acid; and aromatic monocarboxylic acids such as benzoic acid, toluic acid, α-naphtalenecarboxylic acid, β-naphtalenecarboxylic acid, methyl naphtalenecarboxylic acid and phenylacetic acid. These may be used singly or in combinations of two or more.

The monoamine that can be used as a terminal-blocking agent is not particularly limited as long as it has reactivity with a carboxyl group. Examples thereof include aliphatic monoamines such as methylamine, ethylamine, propylamine, butylamine, hexylamine, octylamine, decylamine, stearylamine, dimethylamine, diethylamine, dipropylamine and dibutylamine; alicyclic monoamines such as cyclohexylamine and dicyclohexylamine; and aromatic monoamines such as aniline, toluidine, diphenylamine and naphthylamine. These may be used singly or in combinations of two or more.

Examples of the acid anhydride that can be used as a terminal-blocking agent include a phthalic anhydride, a maleic anhydride, a benzoic anhydride, an acetic anhydride and a hexahydrophthalic anhydride. These may be used singly or in combinations of two or more.

Examples of the monoisocyanate that can be used as a terminal-blocking agent include phenyl isocyanate, tolyl isocyanate, dimethylphenyl isocyanate, cyclohexyl isocyanate, butyl isocyanate, and naphthyl isocyanate. These may be used singly or in combinations of two or more.

Examples of the monoacid halide that can be used as a terminal-blocking agent include halogen-substituted monocarboxylic acids, which are halides of monocarboxylic acids such as benzoic acid, diphenylmethanecarboxylic acid, diphenylsulfoncarboxylic acid, diphenylsulfoxidecarboxylic acid, diphenylsulfidecarboxylic acid, diphenylethercarboxylic acid, benzophenonecarboxylic acid, biphenylcarboxylic acid, α-naphtalenecarboxylic acid, β-naphtalenecarboxylic acid and anthracenecarboxylic acid. These may be used singly or in combinations of two or more.

Examples of the monoester that can be used as a terminal-blocking agent include glycerin monopalmitate, glycerin monostearate, glycerin monobehenate, glycerin monomontanate, pentaerythritol monopalmitate, pentaerythritol monostearate, pentaerythritol monobehenate, pentaerythritol monomontanate, sorbitan monopalmitate, sorbitan monostearate, sorbitan monobehenate, sorbitan monomontanate, sorbitan dimontanate, sorbitan trimontanate, sorbitol monopalmitate, sorbitol monostearate, sorbitol monobehenate, sorbitol tribehenate, sorbitol monomontanate and sorbitol dimontanate. These may be used singly or in combinations of two or more.

Examples of the monoalcohol that can be used as a terminal-blocking agent include propanol, butanol, pentanol, hexanol, heptanol, octanol, nonanol, decanol, undecanol, dodecanol, tridecanol, tetradecanol, pentadecanol, hexadecanol, heptadecanol, octadecanol, nonadecanol, eicosanol, docosanol, tricosanol, tetracosanol, hexacosanol, heptacosanol, octacosanol and triacontanol (these have linear and branched structures), oleyl alcohol, behenyl alcohol, phenol, cresol (o-, m-, p-form), biphenol (o-, m-, p-form), 1-naphthol and 2-naphthol. These may be used singly or in combinations of two or more.

A method for manufacturing a polyamide of the embodiment is not particularly limited and various methods, for example, those as described below, can be employed.

1) Method including steps of heating an aqueous solution or aqueous suspension solution of a dicarboxylic acid and a diamine or an aqueous solution or aqueous suspension solution of a mixture (hereinafter, sometimes simply referred to as a "mixture of them") containing a dicarboxylic acid and a diamine salt and other components such as a lactam and/or an aminocarboxylic acid and polymerizing while keeping a molten state (hereinafter, sometimes simply referred to as the "thermofusion polymerization method"), 2) Method of increasing a degree of polymerization of the polyamide obtained by the thermofusion polymerization method while keeping a solid state at a temperature of a melting point or less (hereinafter, sometimes simply referred to as "thermofusion polymerization/solid phase polymerization method"), 3) Method including steps of heating an aqueous solution or aqueous suspension solution of a dicarboxylic acid and a diamine or a mixture of them, and melting a precipitated prepolymer again by an extruder such as a kneader to increase the degree of polymerization (hereinafter, sometimes simply referred to as "prepolymer/extrusion polymerization method"), 4) Method including steps of heating an aqueous solution or aqueous suspension solution of a dicarboxylic acid and a diamine or a mixture of them, and increasing the degree of polymerization of the precipitated prepolymer while keeping a solid state at temperature of a melting point or less of a polyamide (hereinafter, sometimes simply referred to as "prepolymer/solid phase polymerization method"), 5) Method of polymerizing a dicarboxylic acid and a diamine or a mixture of them while keeping a solid state (hereinafter, sometimes simply referred to as a "monomer/solid phase polymerization method"), 6) Method of polymerizing "salts of a dicarboxylic acid and a diamine" or a mixture of them while keeping a solid state (hereinafter, sometimes simply referred to as a "salt/solid phase polymerization method"), 7) Method of polymerizing a dicarboxylic acid halide equivalent to a dicarboxylic acid and a diamine, "solution method"."

The method for manufacturing a polyamide preferably further includes a step of increasing the degree of polymerization of a polyamide.

The polymerization process in the method for manufacturing a polyamide is not particularly limited, for example, a batch process or a continuous process may be employed. The polymerization apparatus is not particularly limited, and known apparatuses (for example, an autoclave reactor, a tumbler reactor, an extruder reactor such as a kneader) can be employed.

The melting point of a polyamide resin is not particularly limited; however, the melting point is preferably 200 to 340° C., more preferably 210 to 335° C. and further preferably 240 to 330° C. If the melting point of a polyamide resin is the lower limit or more, the heat resistance of a polyamide resin composition can be improved. In contrast, if the melting point of a polyamide resin is the upper limit or less, it is possible to suppress pyrolysis and deterioration of a polyamide resin composition during melt processing.

The melting point of a polyamide resin can be measured in accordance with JIS-K7121. As a measuring apparatus, for example, Diamond DSC manufactured by PerkinElmer, Inc. can be used.

The peak temperature of the cooling crystallization temperature of polyamide resin measured by differential scanning calorimetry (DSC) is not particularly limited; however, the peak temperature is preferably 220° C. or more. If the peak temperature of the cooling crystallization temperature of a polyamide resin is controlled to be 220° C. or more, moldability further improves. The differential scanning calorimetry (DSC) can be performed in accordance with JIS-K7121 at a temperature raising rate of 20° C./minute. More specifically, measurement can be made by the method described in Examples.

Mechanism of mixing the surface-treated carbon nanotube of the embodiment and a resin is not known; however, the mechanism is presumed as follows. First, the surface-treated carbon nanotube of the embodiment is probably is in the state where fibers constituting the carbon nanotube are mutually entangled. In this state, the fibers are scattered with an appropriate space between them and entangled to form a structure. In the surface-treated carbon nanotube of the embodiment, a graphene layer of the carbon nanotube is maintained without breakage before and after a surface treatment. When the surface-treated carbon nanotube having such a specific structure is mixed with a resin, carbon nanotube fibers and the molecular chains of a resin are entangled well. In addition, the functional groups introduced into the carbon nanotube by a surface treatment serve as reaction sites to form an interfacial surface with the resin. Consequently, the carbon nanotube can be mixed with the resin with satisfactory dispersibility and without surface fracture. In the art, in order to introduce many functional groups into a carbon nanotube, a strong acid (for example, sulfuric acid, nitric acid and a mixture of these acids) was used; however, such a method had a problem in that sulfur derived from these acids remains and cuts the molecular chain of a resin. However, in the surface-treated carbon nanotube of the embodiment, since the surface sulfur concentration is less than 0.1 atm %, cutting of the molecular chain of the resin can be suppressed, preventing a reduction of the molecular weight of the resin. Furthermore, the content of substances (bound substance and deposit) formed by the surface treatment of a carbon nanotube is 0.2% or more and the concentration of oxygen considered to be highly reactive with the resin is 1.5 atm % or more. From these, quantitatively and qualitatively excellent interface is probably formed between the carbon nanotube and the resin and thus satisfactory physical properties tend to be obtained when the carbon nanotube is added to the resin.

In a resin composition (polyamide resin composition) containing the surface-treated carbon nanotube of the embodiment and a polyamide resin, the interfacial phase between the polyamide resin and the carbon nanotube will be described. The amount of interfacial phase is increased by a surface treatment. Since the amount of interfacial phase to be formed is greatly influenced by the surface treatment. More specifically, the surface treatment is preferably performed by a chemical species having a high reactivity with the polyamide resin, since the amount of interfacial phase to be formed increases. In view of this, if the carbon nanotube is used in a polyamide resin composition, the surface treatment of the carbon nanotube is preferably performed with at least one selected from the group consisting of a maleic anhydride, poly(acrylic acid), a poly(acrylic acid-co-maleic acid) copolymer, an ethylene-maleic anhydride copolymer and a styrene-maleic anhydride copolymer.

The amount of interfacial phase tends to be increased by performing a surface treatment in the absence of a solvent. Examples of such a surface treatment condition include a surface treatment condition using a maleic anhydride in the absence of a solvent.

The amount of interfacial phase can be controlled not only by conditions of the surface treatment but also by conditions of a post treatment (washing method, etc.) performed after the surface treatment. For example, in the case of the surface treatment using a maleic anhydride in the absence of a solvent, the amount of surface treatment and the amount of interfacial phase as mentioned above tend to be increased by using a non-polar solvent (toluene, etc.) as a washing solvent rather than using a polar solvent (methanol, etc.). As a result, high-temperature physical properties tend to more improve. The reason for this is not known; however it is conceivable that not only the bound substance layer on the surface of a carbon nanotube but also the deposit layer is greatly involved in formation of the interfacial phase with a polyamide resin. Consequently, it is considered that the interface reinforced by the bound substance layer is further reinforced.

The interface between a carbon nanotube and a polyamide resin can be quantified, for example, by dissolving a polyamide component of a carbon nanotube/polyamide composition in a polyamide soluble solvent (hexafluoroisopropanol, etc.) to remove the polyamide component; collecting insoluble components, i.e., carbon nanotube and the interfacial phase; heating them at 600° C. to pyrolytically remove the interfacial phase alone; and measuring a thermal reduction amount in this step to quantify the interfacial phase.

More specifically, the content of an organic substance is preferably 2 to 10 mass %, more preferably 2 to 8 mass %, further preferably 2.5 to 7.5 mass %, still further preferably 3 to 7.0 mass % and further more preferably 3.5 to 6.0 mass %. If the content of an organic substance is controlled so as to fall within the above range, physical properties and molding processability further improve.

The surface sulfur concentration of a surface-treated carbon nanotube having a deposit of an organic substance and measured by X-ray photoelectron spectroscopy is preferably less than 0.1 atm %. The surface sulfur concentration can be measured by detecting sulfur atoms present on the surface of the residue (a carbon nanotube with the interfacial phase) by an X-ray photoelectron spectrometric analyzer (XPS). This value tends to increase when a sulfur-containing compound is used for surface treatment.

The presence or absence of a reaction product derived from a polyamide in the interfacial phase (a phase formed in the boundary between a polyamide and a carbon nanotube) can be confirmed by determining the concentration of nitrogen atoms (when a nitrogen-containing compound is not used for a surface treatment). The interfacial phase also has a function of adhering the polyamide and the carbon nanotube. The nitrogen atoms of such an interfacial phase can be measured and the reaction product derived from a polyamide is preferably involved in the interfacial phase in view of interface strength. The effect of a surface treatment is confirmed by evaluating how high the surface nitrogen concentration of a polyamide resin composition containing a surface-treated carbon nanotube compared to a polyamide resin composition containing a carbon nanotube to which no surface treatment is applied.

In view of this, the surface nitrogen concentration of a surface-treated carbon nanotube having a deposit of an organic substance and determined by X-ray photoelectron spectroscopy is preferably 1 to 15 atm %, more preferably 2 to 15 atm % and further preferably 3 to 15 atm %. If the surface nitrogen is sufficiently present, a crystalline carbon nanotube tends to have further satisfactory physical properties. Thus, the ratio (Id/Ig) of the peak area (Id) of the band having the range of 1335 to 1365 $cm^{-1}$ to the peak area (Ig) of the band having the range of 1565 to 1600 $cm^{-1}$ in the Raman scattering spectrum of the surface-treated carbon nanotube, is preferably 0.1 to 2.0, more preferably 0.1 to 0.9, further preferably 0.1 to 0.5 and still further preferably 0.1 to 0.3.

In the polyamide resin composition, the content of the surface-treated carbon nanotube is preferably 0.5 to 50 mass %, more preferably 1 to 35 mass % and further preferably 5 to 25 mass %. If the content of the surface-treated carbon nanotube is controlled to be the aforementioned upper limit or less, not only the strength of the polyamide resin composition can be further improved but also toughness at high temperature can be further improved. If the content of the surface-treated carbon nanotube is controlled to be the aforementioned lower limit or more, a proper degree of entanglement between a resin component and the surface-treated carbon nanotube can be obtained, with the result that a resin interface can be effectively formed. Consequently, the strength and toughness at high temperature can be further improved.

It is preferable that the polyamide resin composition further contains additives that react with a polyamide resin and/or a surface-treated carbon nanotube as necessary. Such additives are not particularly limited and various types of additives can be used as long as the object of the embodiment is not damaged. Examples of such additives that can be used include also those used as a moldability improver, a colorant, a flame retardant, a plasticizer, a stabilizer, an antioxidant and a UV absorbent.

Examples of the moldability improver include, but are not particularly limited to, a higher fatty acid, a higher fatty acid metal salt, a higher fatty acid ester and a higher fatty acid amide.

Specific examples of the higher fatty acid include a saturated or unsaturated, linear or branched aliphatic monocarboxylic acid having 8 to 40 carbon atoms such as stearic acid, palmitic acid, behenic acid, erucic acid, oleic acid, lauric acid and montanic acid. Of them, stearic acid and montanic acid are preferred.

The higher fatty acid metal salt refers to a metal salt of a higher fatty acid. As a metal element of the metal salt, an element of the first, second and third groups of the periodic table, such as zinc and aluminum, is preferred, and an element such as calcium, sodium, potassium and magnesium is more preferred. Specific examples of the higher fatty acid metal salt include calcium stearate, aluminum stearate, zinc stearate, magnesium stearate, calcium montanate, sodium montanate and calcium palmitate. Of them, a metal salt of montanic acid and a metal salt of stearic acid are preferred.

The higher fatty acid ester refers to an esterified product of a higher fatty acid and an alcohol. Of the esterified products, an ester of an aliphatic carboxylic acid having 8 to 40 carbon atoms and an aliphatic alcohol having 8 to 40 carbon atoms is preferred. As the higher fatty acid, those mentioned above can be used. Examples of the aliphatic alcohol include stearyl alcohol, behenyl alcohol and lauryl alcohol. Specific examples of the higher fatty acid ester include stearyl stearate and behenyl behenate.

The higher fatty acid amide refers to an amide compound of a higher fatty acid. Specific examples of the higher fatty acid amide include stearic acid amide, oleic acid amide, erucamide, ethylenebis stearyl amide, ethylenebis oleyl amide, N-stearyl stearyl amide and N-stearyl erucamide. Of them, stearic acid amide, erucamide, ethylenebis stearyl amide and N-stearyl erucamide are preferred, and ethylenebis stearyl amide and N-stearyl erucamide are more preferred.

These higher fatty acids, higher fatty acid metal salts, higher fatty acid esters and higher fatty acid amides may be independently used singly or in combinations of two or more.

Examples of the colorant include, but are not particularly limited to, dyes such as nigrosine; pigments such as titanium oxide and carbon black; metal particles such as aluminum, coloring aluminum, nickel, tin, copper, gold, silver, platinum, iron oxide, stainless steel and titanium; and metallic pigments such as a pearl pigment made of mica, collar graphite, collar glass fiber, and colored glass flake.

A flame retardant may be blended. As the flame retardant, a non-halogen flame retardant and a bromine-flame retardant are preferred.

The non-halogen flame retardant is at least one flame retardant selected from the group consisting of phosphorus flame retardants such as red phosphorus, ammonium phosphate or ammonium polyphosphate; inorganic compound flame retardants such as metal hydroxides or hydrates of inorganic metal compounds including aluminum hydroxide, magnesium hydroxide, dolomite, hydrotalcite, calcium hydroxide, barium hydroxide, basic magnesium carbonate, zirconium hydroxide, tin oxide, zinc stannate and zinc hydroxystannate and boric acid compounds including zinc borate, zinc metaborate and barium metaborate; triazine flame retardants such as melamine, melam, melem, melon (product obtained by removing 3 ammonia molecule from 3 melem molecules at 300° C. or more), melamine cyanurate, melamine phosphate, melamine polyphosphate, succinoguanamine, adipoguanamine, methylglutaroguanamine and a melamine resin; and silicone flame retardants such as a silicone resin, silicone oil and silica.

The bromine flame retardant is at least one flame retardant selected from the compounds consisting of brominated polystyrenes, brominated polyphenylene ethers, brominated bisphenol epoxy polymers and bromine crosslinked aromatic polymers.

Examples of the plasticizer include aliphatic alcohols, aliphatic amides, aliphatic bisamides, bisurea compounds, polyethylene waxes, p-(octyloxy)benzoic acid and N-butylbenzene sulfonamides.

As the stabilizer, a deterioration inhibitor e.g., for preventing heat deterioration and decoloration during heating, and for improving heat-resistant aging and weather resistance may be included. Examples of the deterioration inhibitor include copper compounds such as copper acetate and copper iodide; phenolic stabilizers such as hindered phenol compounds; phosphite stabilizers; hindered amine stabilizers; triazine stabilizers; and sulfur stabilizers.

Examples of the antioxidant include alkyl phenols, alkylene bisphenols and alkylphenol thioethers.

Examples of the UV absorbent include salicylate ester, benzotriazole and hydroxybenzophenone.

Note that the additive that reacts with a polyamide resin and/or a surface-treated carbon nanotube is preferably at least one selected from the group consisting of carbodiimide group-containing compounds, inorganic acids, organic acids and polymers having an organic acid as a polymerization unit, in view of reactivity with the polyamide resin and the surface-treated carbon nanotube. Of them, an inorganic acid, an organic acid and a polymer having an organic acid as a polymerization unit is more preferable since they can serve also as the surface treatment agent for a carbon nanotube.

The carbodiimide group-containing compound refers to a compound having at least one carbodiimide group in a molecule and any carbodiimide group-containing compound may be used as long as it reacts with a polyamide resin or a surface-treated carbon nanotube. Examples thereof include monofunctional carbodiimide compounds such as N,N'-diisopropylcarbodiimide, N,N'-di(o-toluoyl)carbodiimide, N,N'-dicyclohexylcarbodiimide and N,N'-bis(2,6-diisopropylphenyl)carbodiimide; bifunctional carbodiimide compounds such as p-phenylene-bis(2,6-xylylcarbodiimide), p-phenylene-bis(t-butylcarbodiimide), p-phenylene-bis(mesitylcarbodiimide), tetramethylene-bis(t-butylcarbodiimide) and cyclohexane-1,4-bis(methylene-t-butylcarbodiimide); polyfunctional carbodiimide compounds including isocyanate condensates such as 1,5-naphthalene diisocyanate, 4,4'-diphenylmethane diisocyanate, 4,4'-diphenyldimethylmethane diisocyanate, 1,3-phenylene diisocyanate, 1,4-phenylene diisocyanate, 2,4-tolylene diisocyanate, 2,6- tolylene diisocyanate, a mixture of 2,4-tolylene diisocyanate and 2,6-tolylene diisocyanate, hexamethylene diisocyanate, cyclohexane-1,4-diisocyanate, xylylene diisocyanate, isophorone diisocyanate, dicyclohexylmethane-4,4'-diisocyanate, methylcyclohexane diisocyanate, tetramethylxylylene diisocyanate, 2,6-diisopropylphenyl isocyanate, 1,3,5-triisopropylbenzene-2,4-diisocyanate and polyphenyl polyisocyanate; and polycarbodiimide resins such as poly(t-butyl carbodiimide), poly(tetramethyl xylylene carbodiimide), poly(2,4-toluoylene carbodiimide), poly(2,6-toluoylene carbodiimide), poly(o-tolidine carbodiimide), poly(4,4'-diphenylmethane carbodiimide), poly(4,4'-dicyclohexylmethane carbodiimide), poly(4,4'-diphenylether carbodiimide), poly (3,3'-dimethoxy-4,4'-biphenyl carbodiimide), poly(p-phenylene carbodiimide), polynaphthylene-1,5-carbodiimide, poly(m-xylylene carbodiimide), poly(hydrogenated xylylene carbodiimide), poly(hexamethylene carbodiimide), poly(trimethylhexamethylene carbodiimide) and poly(isophorone carbodiimide). These may be used singly or in combinations of two or more.

The equivalent of a functional group of a carbodiimide compound, in view of the reactivity between a polyamide resin and a surface-treated carbon nanotube, is preferably 50 to 1000 g/eq, more preferably 100 to 800 g/eq and further preferably 200 to 600 g/eq.

Examples of the inorganic acid include the aforementioned inorganic acids for use in the surface treatment of a carbon nanotube; however, any inorganic acid may be used as long as it has a reactivity with a polyamide resin or a surface-treated carbon nanotube. Examples thereof include hydrochloric acid, nitric acid, phosphoric acid, sulfuric acid, boric acid, hydrofluoric acid, hydrogen peroxide, perphosphoric acid, persulfuric acid and peroxo-perchloric acid. Of them, in view of interaction with a polyamide resin, phosphoric acid and hydrogen peroxide are preferred.

Examples of the organic acid include the aforementioned organic acids for use in the surface treatment of a carbon nanotube; however any organic acid may be used as long as it has a reactivity with a polyamide resin or a surface-treated carbon nanotube. Examples thereof include sulfonic acid, citric acid, oxalic acid, formic acid, acetic acid, acrylic acid, diacrylic acid, methacrylic acid, crotonic acid, isocrotonic acid, cinnamic acid, maleic acid, fumaric acid, dimethyl fumaric acid, itaconic acid, citraconic acid, anhydrous percarbonic acid, peroxo-perchloric acid, peracetic acid, perbenzoic acid and anhydrides of these. Examples of the anhydrides include a fumaric anhydride, a maleic anhydride, a benzoic anhydride and an acetic anhydride.

Of them, in view of interaction with a polyamide resin, acetic acid, fumaric acid, citric acid, oxalic acid, acrylic acid, maleic acid and maleic anhydride are preferred and maleic anhydride is more preferred.

Examples of the polymer having an organic acid as a polymerization unit include the aforementioned polymers for use in the surface treatment of a carbon nanotube; however, any polymer may be used as long as it has a reactivity with a polyamide resin or a surface-treated carbon nanotube. Examples of the copolymer of a maleic anhydride include a styrene-maleic anhydride copolymer, an ethylene-maleic anhydride, a n-butene-maleic anhydride copolymer, an isobutene-maleic anhydride copolymer, a n-benzene-maleic anhydride copolymer, a 2-methyl-1-butene-maleic anhydride copolymer, a 4-methyl-1-benzene-maleic anhydride copolymer, a 1,3-heptadiene-maleic anhydride copolymer and a trimethyl benzene-maleic anhydride copolymer. Other examples thereof include copolymers obtained by copolymerizing at least two selected from the group consisting of sulfonic acid, citric acid, oxalic acid, formic acid, acetic acid, acrylic acid, diacrylic acid, methacrylic acid, crotonic acid, isocrotonic acid, cinnamic acid, maleic acid, fumaric acid, dimethyl fumaric acid, itaconic acid and citraconic acid. Of them, at least one selected from the group consisting of poly(acrylic acid), poly(acrylic acid-co-maleic acid), ethylene-maleic anhydride and styrene-maleic anhydride is preferred since they have satisfactory interaction with a polyamide resin.

The total content of additives in a polyamide resin composition is not particularly limited; however, the total content is preferably 15 mass % or less, more preferably 10 mass % or less and further preferably 5 mass % or less. If the total content of additives is controlled to be the aforementioned upper limit or less, e.g., an excessive polymerization reaction with a polyamide resin can be further suppressed and gelatinization of the polyamide resin composition can be further effectively suppressed. As a result, desired physical properties can be further improved.

The polyamide resin composition may contain a resin other than a polyamide and a rubber component as necessary as long as the object of the embodiment is not damaged. Specifically, examples include at least one selected from a thermoplastic resin, a thermosetting resin and a rubber component. Of them, a thermoplastic resin and a rubber component are preferred.

The polyamide resin composition may further contain a filler other than a carbon nanotube as necessary as long as the object of the embodiment is not damaged. Examples of the filler other than a carbon nanotube include glass fiber, carbon fiber, wollastonite, talc, mica, kaolin, silicon nitride, potassium titanate, barium sulfate, calcium carbonate, apatite, sodium phosphate, fluorite and molybdenum disulfide. Of them, in view of physical properties, safety and economic aspect, glass fiber, carbon fiber, wollastonite, talc, mica, kaolin, boron nitride, potassium titanate and apatite are preferred and glass fiber is more preferred.

The glass fiber and carbon fiber are not particularly limited. Any glass fiber and carbon fiber can be used, regardless of whether they are a long or short fiber and regardless of shapes including irregular sectional shapes (for example, cocoon and elongated circle).

The number average fiber diameter of a glass fiber and a carbon fiber is preferably 3 to 30 µm in view of exhibiting high physical properties. The weight average fiber length of a glass fiber and a carbon fiber is preferably 100 to 750 µm, in view of exhibiting high physical properties. The aspect ratio (L/D) of weight average fiber length (L) to number average fiber diameter (D) of each of a glass fiber and carbon fiber is preferably 10 to 100 in view of exhibiting high physical properties. In particular, a glass fiber and carbon fiber having a number average fiber diameter of 3 to 30 µm, a weight average fiber length of 100 to 750 µm and an aspect ratio (L/D) of 10 to 100 are more preferred.

The number average fiber diameter of wollastonite is preferably 3 to 30 µm, in view of exhibiting high physical properties. The weight average fiber length of wollastonite is preferably 10 to 500 µm, in view of exhibiting high physical properties. The aspect ratio (L/D) of the weight average fiber length (L) to the number average fiber diameter (D) of wollastonite is preferably 3 to 100 in view of exhibiting high physical properties. In particular, a wollastonite having a number average fiber diameter of 3 to 30 µm, a weight average fiber length of 10 to 500 µm and an aspect ratio (L/D) of 3 to 100 is more preferred.

The number average fiber diameters of talc, mica, kaolin, silicon nitride and potassium titanate are preferably 0.1 to 3 µm in view of exhibiting high physical properties.

The total content of fillers other than a carbon nanotube in a polyamide resin composition is not particularly limited; however, the total content is preferably 50 mass % or less, more preferably 40 mass % or less and further preferably 35 mass % or less. If the total content of fillers is controlled to be 50 mass % or less, the physical properties desirable for a polyamide resin composition can be further improved.

The specific strength of a polyamide resin composition at 120° C. is preferably 35 MPa or more, preferably 37 MPa or more, more preferably 38 MPa or more, further preferably, 40 MPa or more and most preferably 42 MPa or more. If the specific strength of a polyamide resin composition is controlled to be the above value or more, deformation against stress can be suppressed. Furthermore, as described later, the specific strength refers to tensile strength per density. The larger the value of a specific strength, the more preferable in view of reducing weight of automotive parts, etc.

The specific strength used herein refers to tensile strength per density. The tensile strength can be measured as follows. The temperature is raised up to 120° C. by "Autograph AG-5000D" manufactured by Shimadzu Corporation, and then a dumbbell test piece of ISO36 Type3 (size of the middle parallel portion of the dumbbell between the chucks: length 16 mm×width 4 mm×thickness 2 mm) is placed there, allowed to stand still for 30 minutes, and thereafter, the tensile strength is measured by a tensile tester (chuck distance: 25 mm). The obtained tensile strength value is divided by the density of the polyamide resin composition to obtain the specific strength of the polyamide resin composition. More specifically, the specific strength can be obtained by the method described in Examples.

The breaking elongation of the polyamide resin composition at 120° C. is preferably 20% or more, more preferably 30% or more and further preferably 35% or more. If the breaking elongation of a polyamide resin composition is controlled to be 20% or more, it is preferable because the practical resistance of materials and parts against breaking and cracking caused by some displacement/deformation increases.

The breaking elongation at 120° C. mentioned herein can be measured as follows. The temperature is raised up to 120° C. by "Autograph AG-5000D" manufactured by Shimadzu Corporation and then a dumbbell test piece of ISO36 Type3 (size of the middle parallel portion of the dumbbell between the chucks: length 16 mm×width 4 mm×thickness 2 mm) is placed there, allowed to stand still for 30 minutes and thereafter, the breaking elongation is measured by a tensile tester (chuck distance: 25 mm). More specifically, the breaking elongation can be obtained by the method described in Examples.

The creep property (the time until deformation reaches 15% by application of a stress of 30 MPa) of a polyamide resin composition at 120° C. is preferably 10000 seconds or more. The creep property shows a life duration of the polyamide resin composition when a load which will not destroy the polyamide resin composition in a short time is continuously applied. Thus, the longer the life duration, the more preferable. The creep property is more preferably 13000 seconds or more, further preferably 15000 seconds or more, still further preferably 20000 seconds or more, further more preferably 30000 seconds or more and most preferably 40000 seconds or more. More specifically, the creep property can be obtained by the method described in Examples.

A method for manufacturing a polyamide resin composition of the embodiment, for example, the following methods can be employed: (i) a method (melt-kneading method) in which a surface-treated carbon nanotube, a polyamide resin and other components are kneaded in a molten state by a kneader (for example, single screw or multi screw kneading machine, a kneader, a Henschel mixer, a ball mill, a planetary mill, a Banbury mixer, a roll and Brabender Plastograph); and (ii) a method in which a surface-treated carbon nanotube, a polyamide resin and other components are added to a solvent (for example, a hydrocarbon such as hexane, heptane, benzene, toluene and xylene and a derivative thereof). The above (ii) method includes a method of mixing soluble components with each other or a method of mixing a soluble component and an insoluble component in a suspension state (solution mixture method).

Of them, the melt-kneading method (i) is preferred in view of industrial cost. In the melt-kneading, a single screw extruder and a twin screw extruder are preferably used and use of a twin screw extruder is more preferred.

The temperature (melt-kneading temperature) for melt-kneading a surface-treated carbon nanotube, a polyamide resin and other components is not particularly limited. When a polyamide resin having a melting point is used, the melt-kneading temperature is preferably the melting point of the polyamide resin or more and more preferably (the melting point of the polyamide resin+50)° C. or less. When a polyamide resin having no melting point, the melt-kneading temperature is preferably (the glass transition temperature of the polyamide resin+50)° C. or more and (the glass transition temperature of the polyamide resin+150)° C. or less. The melting point and glass transition temperature of the polyamide can be measured by a differential scanning calorimetry (DSC) apparatus.

It may be usually sufficient if the shearing speed of the extruder for melt-kneading a surface-treated carbon nanotube, a polyamide resin and other components is about 10 to 10000 $sec^{-1}$. The shearing hysteresis time may be generally about 10 to 1200 seconds.

Such a polyamide resin composition is molded and a molded product can be used as various types of members. As the method of molding a polyamide resin composition to obtain a molded article, known methods such as extrusion molding, injection molding, vacuum molding, blow molding, injection compression molding, decorative molding, multi-material molding, gas assist injection molding, foaming injection molding, low pressure molding, super thin-wall injection molding (super-high-speed injection molding) and in-mold composite molding (insert molding and outsert molding) can be used.

The molded article of a polyamide resin composition can be formed into various forms depending upon the uses. Examples of the forms include pellet forms, fibrous forms, thread forms, sheet forms, film forms, plate forms, stick forms and tubular forms.

The material containing the surface-treated carbon nanotube of the embodiment rarely reduces the molecular weight of the resin to be mixed and the molded article is excellent in strength and toughness at high temperature and low in warp and deformation. Thus, the molded article can be used in various uses. Examples of preferable uses include, but are not particularly limited to, materials for automotive parts, electrical parts, electronic parts, portable device parts, machine/industrial parts, business machine parts and aviation/space parts and components of paints.

Since the surface-treated carbon nanotube of the embodiment can be manufactured by the aforementioned methods, etc. and the carbon nanotube to be used as a raw material is inexpensive, mass production can be made. This is preferable also from the industrial point of view.

Since the surface-treated carbon nanotube of the embodiment has a functional group, the surface-treated carbon nanotube can be added to a resin and a rubber component. The material containing the surface-treated carbon nanotube has few surface fractures. In addition, when the material is mixed with a resin, the molecular weight of the resin rarely reduces. For the reasons, the material can be preferably used in various uses. Examples of preferable uses of the material include, but are not particularly limited to, automotive parts, electrical parts, electronic parts, portable device parts, machine/industrial parts, business machine parts and aviation/space parts.

Second Embodiment

Now, the second embodiment will be described. Note that descriptions on the same contents as in the first embodiment will be appropriately omitted.

The surface-treated carbon nanotube of the embodiment contains a compound represented by any one of formula (1) to formula (4). If the surface-treated carbon nanotube containing at least a compound represented by any one of formula (1) to formula (4) is used, at least excellent strength and toughness at high temperature can be provided when the surface-treated carbon nanotube is mixed with a resin.

Since the surface-treated carbon nanotube of the embodiment contains at least a compound represented by any one of formula (1) to formula (4), the reactivity with and adhesion to a resin improves. Note that it is preferable that a compound represented by any one of formula (1) to formula (4) chemically binds to the surface of the surface-treated carbon nanotube. These compounds are maleic anhydrides or derivatives thereof. The compound chemically bound to a surface-treated carbon nanotube is defined as a "bound substance" whose functional group is introduced into the carbon nanotube. Note that a method for confirming whether a functional group is introduced or not, the method as described in the first embodiment can be employed.

It is preferable that the surface-treated carbon nanotube of the embodiment further contains a compound represented by formula (5) or formula (6). If not only compounds represented by formula (1) to formula (4) but also compounds represented by formula (5) and formula (6) are further contained, not only the strength and toughness at high temperature are further improved but also excellent strength and toughness can be obtained at normal temperature. The presence of compounds represented by formula (5) and formula (6) in the surface-treated carbon nanotube can be confirmed by the method described in the first embodiment.

In formula (5), $n^1$ is 2 to 400, preferably 2 to 260, more preferably 2 to 130 and further preferably 2 to 70. If $n^1$ is 2 to 400, the strength of carbon nanotube fibers entangled with the resin to be mixed and toughness are improved.

In formula (6), $n^2$ is 2 to 650, preferably 2 to 350, more preferably 2 to 210 and further preferably 2 to 120. If $n^2$ is 2 to 650, the strength of carbon nanotube fibers entangled with the resin to be mixed and toughness are improved.

(Carbon Nanotube Raw-Material)

As a carbon nanotube serving as a raw material for the surface-treated carbon nanotube of the embodiment, the carbon nanotubes described in the first embodiment can be appropriately used.

(Surface Treatment)

As the surface treatment, the reactions, compounds (surface treatment agent), treatment conditions and the like as described in the first embodiment will be employed. Of them, the surface-treated carbon nanotube of the embodiment is preferably obtained by treating the surface at least with maleic anhydride. The present inventors surprisingly found that if the surface-treated carbon nanotube of the embodiment obtained by treating the surface at least with maleic anhydride is mixed with a resin, further excellent strength and toughness at least at high temperature can be provided. Note that in the embodiment, unless otherwise specified, derivatives of a maleic anhydride are included in "maleic anhydride."

As described in the first embodiment, a functional group can be introduced into the surface of a carbon nanotube by treating the surface at least with maleic anhydride. In addition, surface-treated carbon nanotubes containing compounds represented by formula (1) to formula (4) as mentioned above and further compounds represented by formula (5) and formula (6) can be effectively obtained.

As the conditions of a surface treatment with a maleic anhydride, the conditions described in the first embodiment can be appropriately employed. As a reactor for use in the embodiment, known reactors can be used. The reactors described in the first embodiment can be used, for example.

In the embodiment, not only a maleic anhydride is used but also other surface treatment agents may be used in combination. Examples of such a surface treatment agent include at least one selected from the group consisting of an inorganic acid, an organic acid and a polymer having an organic acid as a polymerization unit (hereinafter, sometimes simply referred to as a "polymer"). As the other surface treatment agents, those described in the first embodiment can be used.

When a solvent is used for dispersing a raw-material carbon nanotube in a surface treatment reaction, the type of solvent is not particularly limited. An aqueous solvent or a non-aqueous solvent may be used. As the aqueous solvent and non-aqueous solvent, those described in the first embodiment can be appropriately used. As to the methods and conditions for improving dispersibility to a solvent, those described in the first embodiment can be appropriately employed. Of them, at least one selected from the group consisting of water, toluene, an alcohol solvent, an ether solvent, an acetone solvent and the absence of a solvent is preferred.

A solvent may be used for dispersing a carbon nanotube; however, it is preferable that a surface treatment is performed by using at least a maleic anhydride in the absence of a solvent. As is described in the first embodiment, it is preferred not to use a solvent because the reactivity of a maleic anhydride with a carbon nanotube is improved and a functional group is further effectively introduced into the carbon nanotube if a solvent is not used. Furthermore, surface-treated carbon nanotubes containing the compounds represented by formula (1) to formula (4) and compounds represented by formula (5) and (6) can be effectively obtained.

If a radical reaction is performed as the reaction for introducing a functional group into the surface of a carbon nanotube, examples thereof include a reaction for grafting the functional group to the main chain of a carbon nanotube as described in the first embodiment. As the radical initiator to be used in such a radical reaction, those described in the first embodiment can be appropriately used.

The reaction for treating the surface of a raw-material carbon nanotube is preferably performed in a liquid phase, as is described in the first embodiment. Particularly, a maleic anhydride is convenient since it can be easily changed into a liquid state by heating as it has a melting point of 52.8° C.

In the carbon nanotube whose surface is treated in a liquid phase, occurrence of the surface fracture is further reduced. Thus, when the carbon nanotube is mixed with a resin to form a composite material, the addition effect of the carbon nanotube can be further improved. In addition, extrudability during molding can be further improved. Since the reaction is performed in a liquid phase, usually, the surface treatment can be performed in mild reaction conditions and a large-scale apparatus is not required. This is advantageous in view of a process.

As the surface treatment method in a liquid phase, for example, a method of using a treatment agent, which is liquid at normal temperature and normal pressure, a method of using a treatment agent, which is previously changed into liquid by heating, and a method of using a treatment agent, which is previously changed into a liquid state by using a solvent, can be employed. Accordingly, even if a treatment agent is, for example, solid at normal temperature and normal pressure, the treatment agent can be used by changing it into a solution by use of a solvent or changing it into a solution by heating it.

Note that when a treatment agent, which is liquid at normal temperature and normal pressure and a treatment agent which is previously changed into a liquid state, i.e., solution by heating it are used, the surface treatment comes to be performed in a liquid phase and in the absence of a solvent. By performing a surface treatment in a liquid phase and in the absence of a solvent, a surface-treated carbon nanotube containing a compound represented by any one of formula (1) to formula (4) can be effectively obtained. Furthermore, a surface-treated carbon nanotube not only containing a compound represented by any one of formula (1) to formula (4) but also containing a compound represented by formula (5) or formula (6) can be effectively obtained.

Specific examples of the surface treatment performed in a liquid phase include a surface treatment of using a maleic anhydride, which is liquid at normal temperature and normal pressure, a surface treatment of using a maleic anhydride, which is previously changed into a liquid state by heating it and a surface treatment of using a maleic anhydride, which is previously changed into a liquid state by dissolving it in a solvent. To describe more specifically, since the melting point of a maleic anhydride is 52.8° C., the maleic anhydride can be changed into a solution by heating it and the maleic anhydride can be dispersed in a solvent to obtain a solution. In this manner, the surface treatment of a carbon nanotube using a maleic anhydride can be performed in a liquid phase. Whether a maleic anhydride is changed into a solution by heating it or a maleic anhydride is dispersed in a solvent to obtain a solution can be appropriately chosen in consideration of reaction conditions for a surface treatment, etc.

A post treatment performed after the surface treatment will be described. After the surface treatment, if necessary, a reaction product can be filtered, washed and dried. As the post treatment performed after the surface treatment, the treatments described in the first embodiment can be appropriately employed.

Since a surface treatment is performed with a maleic anhydride, the surface-treated carbon nanotube of the embodiment has few surface fractures. Owing to this, the carbon nanotube is excellent in adhesion to the resin to be blended. As a result, it is expected that the physical properties of a composite material containing the surface-treated carbon nanotube and the resin are drastically improved. Furthermore, if surface fractures are few, irregularities on the surface of a carbon nanotube will not be removed. Thus, it is expected to obtain a highly active surface. Also in this respect, drastic improvement in the physical properties of the composite material is expected.

Subsequently, a more preferred aspect of the surface-treated carbon nanotube will be more specifically described. The thermal reduction amount of the surface-treated carbon nanotube of the embodiment at 600° C. in a nitrogen atmosphere is preferably 0.2 to 40%, more preferably 0.5 to 40% and further preferably 0.8 to 40%. As is described in the first embodiment, the larger the thermal reduction amount, the larger the number of functional groups bound to or deposited on the carbon nanotube tends to be. In other words, a sufficient number of functional groups are introduced. Substances vaporized (sublimated) at 600° C. include (i) the bound substance described in the first embodiment and (ii) the deposit described in the first embodiment. Thus, the thermal reduction amount at 600° C. in the surface-treated carbon nanotube may serve as an index showing the proportion of the bound substance and the deposit. More specifically, the larger the thermal reduction amount at 600° C., the more the bound substance and deposit are presumably present, indicating that the larger the thermal reduction amount at 600° C., the more the functional groups capable of binding to a resin are present and the affinity of the surface-treated carbon nanotube for a resin tends to improve. More specifically, if the thermal reduction amount at 600° C. is controlled to be 0.2% or more, the affinity for a resin is further improved by the presence of the aforementioned bound substance and deposit (however, the function is not limited to this). The thermal reduction amount can be obtained by the method described in the first embodiment.

The surface oxygen concentration and surface sulfur concentration of the surface-treated carbon nanotube of the embodiment, which are measured by X-ray photoelectron spectroscopy (XPS), are each preferably controlled to be preferable values as described in the first embodiment.

The physical property values (Id/Ig, ΔId/Ig, etc.) in the Raman scattering spectrum of the surface-treated carbon nanotube of the embodiment are each preferably controlled to be preferable values as described in the first embodiment.

Furthermore, as is described in the first embodiment, in the cases where an organic acid (maleic anhydride, etc.) and a polymer having an organic acid as a polymerization unit (a poly(acrylic acid-co-maleic acid) copolymer, an ethylene-maleic anhydride copolymer, a styrene-maleic anhydride copolymer, etc.) are used, a crystalline carbon nanotube is preferably used as the carbon nanotube before the surface treatment. In addition, the surface-treated carbon nanotube to be obtained is preferably a crystalline carbon nanotube. In view of this, the ratio (Id/Ig) of the aforementioned surface-treated carbon nanotube is preferably 0.1 to 0.9, more preferably 0.1 to 0.5 and further preferably 0.1 to 0.3.

The fiber outer diameter and L/D ratio (=aspect ratio) of the surface-treated carbon nanotube of the embodiment are each preferably controlled to be preferable values as described in the first embodiment.

If the surface-treated carbon nanotube of the embodiment is mixed with a resin, excellent strength and toughness not only at normal temperature but also at high temperature can be provided. Examples of the resin to be added include at least one selected from a thermoplastic resin, a thermosetting resin and a rubber component. Of them, a thermoplastic resin and a rubber component are preferred. Those described in the first embodiment can be appropriately used as these components.

Mechanism of mixing the surface-treated carbon nanotube of the embodiment and a resin is not known; however, the mechanism is presumed as follows. First, the surface-treated carbon nanotube of the embodiment probably is in the state where fibers constituting the carbon nanotube are mutually entangled. In this state, the fibers are scattered with an appropriate space between them and entangled to form a structure. In the surface-treated carbon nanotube of the embodiment, the graphene layer of the carbon nanotube is maintained without breakage before and after a surface treatment. When the surface-treated carbon nanotube having such a specific structure is mixed with a resin, the carbon nanotube fibers and the molecular chains of the resin are entangled well. In addition, the functional groups introduced into the carbon nanotube by a surface treatment serve as reaction sites to form an interface with the resin. Consequently, the carbon nanotube can be mixed with the resin with satisfactory dispersibility and without surface fracture. Conventionally, in order to introduce many functional groups into a carbon nanotube, a strong acid (for example, sulfuric acid, nitric acid and a mixture of these acids) was used; however, such a method had a problem in that sulfur derived from these acids remains and cuts the molecular chain of a resin. In view of this, the surface sulfur concentration of the surface-treated carbon nanotube is preferably less than 0.1 atm %. If so, cutting of the molecular chain of a resin can be effectively suppressed and reduction in the molecular weight of the resin can be further prevented.

Since the surface-treated carbon nanotube of the embodiment can be manufactured by the aforementioned methods, etc. and the carbon nanotube to be used as a raw material is inexpensive, mass production can be made. This is preferable also from the industrial point of view.

When the surface-treated carbon nanotube of the embodiment is mixed with a resin, excellent strength and toughness at high temperature can be provided. More specifically, in the embodiment, it is possible to obtain a resin composition containing the aforementioned surface-treated carbon nanotube and a thermoplastic resin. The thermoplastic resin is not particularly limited, for example, those described in the first embodiment can be appropriately employed. As the thermoplastic resin, at least a polyimide is preferred.

Since the surface-treated carbon nanotube of the embodiment has a functional group, it can be added to a resin and a rubber component. The material containing such a surface-treated carbon nanotube has few surface fractures. In addition, when the material is mixed with a resin, the molecular weight of the resin rarely reduces. For the reasons, the material can be used in various uses. Examples of preferable uses of the material include, but are not particularly limited to, automotive parts, electrical parts, electronic parts, portable device parts, machine/industrial parts, business machine parts and aviation/space parts.

Third Embodiment

Now, the third embodiment will be described. Note that descriptions on the same contents as in the first embodiment and second embodiment will be appropriately omitted.

(Polyamide Resin Composition (3))

The third embodiment is directed to a polyamide resin composition containing a surface-treated carbon nanotube and a polyamide resin, and more specifically, a polyamide resin composition (3) containing a surface-treated carbon nanotube, in which the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum is 0.1 to 2.0, and a polyamide resin; in which a specific strength of ISO36 Type3 dumbbell at 120° C. is 35 MPa or more. The polyamide resin composition, if constituted as mentioned above, may serve as a composite material of a carbon nanotube having excellent in strength and toughness at least at high temperature.

The peak temperature of the cooling crystallization temperature of the polyamide resin composition (3) measured by differential scanning calorimetry (DSC) is preferably 240° C. or less, more preferably 239° C. or less, further preferably 238° C. or less and still further preferably 234° C. or less. If the peak temperature of the cooling crystallization temperature of the polyamide resin composition is controlled to fall within the above range, crystallization can be effectively controlled. As a result, quality reduction of the crystal can be suppressed. Differential scanning calorimetry (DSC) can be performed in accordance with JIS-K7121 at a temperature raising rate of 20° C./minute. More specifically, measurement can be made by the method described in Examples.

The peak temperature of the cooling crystallization temperature of the polyamide resin composition (3) tends to decrease, e.g., if a surface-treated carbon nanotube having a higher surface oxygen concentration or a surface-treated carbon nanotube having a higher thermal reduction amount is used.

The specific strength of the polyamide resin composition (3) at 120° C. is 35 MPa or more. If the specific strength of the polyamide resin composition (3) is controlled to be 35 MPa or more, deformation against stress can be suppressed. Furthermore, as will be described later, the specific strength refers to tensile strength per density. The strength value is preferably large in view of reducing weight of automotive parts, etc. The specific strength of the polyamide resin composition is preferably 37 MPa or more, more preferably 38 MPa or more, further preferably 40 MPa or more and most preferably 42 MPa or more.

The specific strength herein refers to tensile strength per density. The tensile strength can be measured as follows. The temperature is raised up to 120° C. by "Autograph AG-5000D" manufactured by Shimadzu Corporation, and then a dumbbell test piece of ISO36 Type3 (size of the middle parallel portion of the dumbbell between the chucks: length 16 mm×width 4 mm×thickness 2 mm) is placed there, allowed to stand still for 30 minutes, and thereafter, the tensile strength is measured by a tensile tester (chuck distance: 25 mm). The obtained tensile strength value is divided by the density of the polyamide resin composition to obtain the specific strength of the polyamide resin composition. More specifically, the tensile strength can be obtained by the method described in Examples.

The breaking elongation of the polyamide resin composition (3) at 120° C. is preferably 20% or more, more preferably 30% or more and further preferably 35% or more. If the breaking elongation of a polyamide resin composition is controlled to be 20% or more, it is preferable because the practical resistance of materials and parts against breaking and cracking caused by some displacement/deformation increases.

The breaking elongation at 120° C. mentioned herein can be measured as follows. The temperature is raised up to 120° C. by "Autograph AG-5000D" manufactured by Shimadzu Corporation and then a dumbbell test piece of ISO36 Type3

(size of the middle parallel portion of the dumbbell between the chucks: length 16 mm×width 4 mm×thickness 2 mm) is placed there, allowed to stand still for 30 minutes and thereafter, the breaking elongation is measured by a tensile tester (chuck distance: 25 mm). More specifically, the breaking elongation can be obtained by the method described in Examples.

The creep property (the time until deformation reaches 15% by application of a stress of 30 MPa) of the polyamide resin composition (3) at 120° C. is preferably 10000 seconds or more. The creep property shows a life duration of the polyamide resin composition when a load which will not destroy the polyamide resin composition in a short time is continuously applied. Thus, the longer the life duration, the more preferable. The creep property is more preferably 13000 seconds or more, further preferably 15000 seconds or more, still further preferably 20000 seconds or more, further more preferably 30000 seconds or more and most preferably 40000 seconds or more. More specifically, the creep property can be obtained by the method described in Examples.

(Polyamide Resin)

As the polyamide resin, those described in the first embodiment and the second embodiment can be appropriately used.

(Carbon Nanotube Raw-Material)

As a carbon nanotube serving as a raw material for the surface-treated carbon nanotube, the materials described in the first embodiment and the second embodiment can be appropriately used.

As described in the first embodiment and the second embodiment, the Raman scattering spectrum of a carbon nanotube can be used as an index for evaluating the degree of surface fracture by a surface treatment. Specifically, spectrum ("spectrum A") having at least one peak top between 1565 and 1600 cm$^{-1}$ is a spectrum that commonly emerges in a graphite substance; whereas a spectrum ("spectrum B") having at least one peak top between 1335 and 1365 cm$^{-1}$ is a spectrum that is derived from a defect of the carbon nanotube. If the carbon nanotube has a point detect or a defective edge of a crystal, etc., the intensity of spectrum B increases. The intensity of spectrum B relative to spectrum A serves as a rough indication of the amount of defect.

Accordingly, if there is a large difference in the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum of a carbon nanotube before and after the surface treatment, the degree of surface fracture becomes large by the difference. If the absolute value ($\Delta$Id/Ig) of the difference between the above ratios (Id/Ig) before and after the surface treatment is adjusted, the state of the surface fracture in the surface treatment stage can be controlled. If the absolute value ($\Delta$Id/Ig) of the difference between the above ratios (Id/Ig) before and after the surface treatment is small, the surface-treated carbon nanotube having few surface fractures in the surface treatment stage by the difference can be obtained. Examples of a method for reducing the above absolute value ($\Delta$Id/Ig) include a method of using a milder surface treatment agent.

According to a preferable aspect of the surface-treated carbon nanotube, the absolute value ($\Delta$Id/Ig) of the difference between the above ratios (Id/Ig) before and after the surface treatment can be 0 to 1.0, more preferably 0 to 0.6, further preferably 0 to 0.4 and still preferably 0 to 0.5. If the absolute value ($\Delta$Id/Ig) of the difference between the above ratios (Id/Ig) falls within the above range, the surface fracture of a carbon nanotube by the reaction step can be more significantly suppressed.

(Surface Treatment)

As the surface treatment, e.g., the reactions, compounds (surface treatment agents) and treatment conditions as described in the first embodiment and the second embodiment can be appropriately employed.

Mechanism of mixing the surface-treated carbon nanotube of the embodiment and a resin is not known; however, the mechanism is presumed as follows. First, the surface-treated carbon nanotube is in the state where fibers constituting the carbon nanotube are mutually entangled. In this state, the fibers are scattered with an appropriate space between them and entangled to form a structure. In the surface-treated carbon nanotube, a graphene layer of the carbon nanotube is maintained without breakage before and after a surface treatment. When the surface-treated carbon nanotube having such a specific structure is mixed with a resin, carbon nanotube fibers and the molecular chains of a resin are entangled well. In addition, since the functional groups introduced into the carbon nanotube by a surface treatment serve as reaction sites to form an interface with the resin. Consequently, the carbon nanotube can be mixed with the resin with satisfactory dispersibility and without surface fracture. Conventionally, in order to introduce many functional groups into a carbon nanotube, a strong acid (for example, sulfuric acid, nitric acid and a mixture of these acids) was used; however, such a method had a problem in that sulfur derived from these acids remains and cuts the molecular chain of a resin. In view of this, the surface sulfur concentration of the surface-treated carbon nanotube is preferably less than 0.1 atm %. If so, cutting of the molecular chain of a resin can be effectively suppressed and reduction in the molecular weight of the resin can be further prevented.

In the conventional surface-treated carbon nanotube, if the surface of the carbon nanotube is treated with a strong acid such as sulfuric acid and nitric acid, even if washing is carefully performed by increasing the number of washing times, a trace amount of strong acid inevitably remains on the surface of the carbon nanotube. The remaining strong acid cuts the molecular chain of a resin and reduces a molecular weight. In addition to this problem, metal parts (e.g., screws) of an extruder, etc. are eroded and abraded, lowering extrudability. However, in the surface-treated carbon nanotube of the embodiment, extrudability does not decrease.

Accordingly, in view of preventing molecular weight reduction and further improving extrudability, it is preferable that a surface treatment is performed by use of at least one selected from the group consisting of the aforementioned inorganic acids, organic acids and polymers having an organic acid as a polymerization unit and without using a strong acid. More specifically, it is preferable that a surface treatment is performed by use of at least one selected from the group consisting of hydrogen peroxide, citric acid, oxalic acid, acrylic acid, diacrylic acid, methacrylic acid, maleic acid, fumaric acid, dimethyl fumaric acid, itaconic acid, citraconic acid, fumaric anhydride, maleic anhydride, benzoic anhydride, acetic anhydride, poly(acrylic acid), poly (acrylic acid-co-maleic acid), an ethylene-maleic anhydride copolymer and a styrene-maleic anhydride copolymer, and without using a strong acid. Of them, it is further preferable that a surface treatment is performed by use of at least a maleic anhydride or an ethylene-maleic anhydride copolymer and without using a strong acid; and it is further preferable that a surface treatment is performed by use of at least a maleic anhydride and without using a strong acid.

Note that the strong acid herein refers to, for example, sulfuric acid, nitric acid and hydrochloric acid.

The surface-treated carbon nanotube can be manufactured by the aforementioned methods, etc. Since the carbon nanotube to be used as a raw material is inexpensive, mass production can be made. This is preferable also from the industrial point of view.

Subsequently, a more preferred aspect of the surface-treated carbon nanotube will be more specifically described. The thermal reduction amount of the surface-treated carbon nanotube of the embodiment at 600° C. in a nitrogen atmosphere is preferably 0.2 to 40%, more preferably 0.5 to 40% and further preferably 0.8 to 40%. As is described in the first embodiment and the second embodiment, the larger the thermal reduction amount, the larger the number of functional groups bound to or deposited on the carbon nanotube tends to be. In other words, a sufficient number of functional groups are introduced. Substances vaporized (sublimated) at 600° C. include (i) a bound substance described in the first embodiment and (ii) a deposit described in the first embodiment. Thus, the thermal reduction amount at 600° C. in the surface-treated carbon nanotube may serve as an index showing the proportion of the bound substance and the deposit. More specifically, the larger the thermal reduction amount at 600° C., the more the bound substance and deposit are presumably present, indicating that the larger the thermal reduction amount at 600° C., the more the functional groups capable of binding to a resin are present and the affinity of the surface-treated carbon nanotube for a resin tends to improve. More specifically, if the thermal reduction amount at 600° C. is controlled to be 0.2% or more, the affinity for a resin is further improved by the presence of the aforementioned bound substance and deposit (however, the function is not limited to this). The thermal reduction amount can be obtained by the method described in the first embodiment and the second embodiment.

The surface oxygen concentration and surface sulfur concentration of the surface-treated carbon nanotube, which are measured by X-ray photoelectron spectroscopy (XPS), are each preferably controlled to be preferable values as described in the first embodiment and the second embodiment.

In the polyamide resin composition, the content of the surface-treated carbon nanotube is preferably 0.5 to 50 mass %, more preferably 1 to 35 mass % and further preferably 5 to 25 mass %. If the content of the surface-treated carbon nanotube is controlled to be 50 mass % or less, not only the strength but also toughness at high temperature can be improved. If the content of the surface-treated carbon nanotube is controlled to be 0.5 mass % or more, a proper degree of entanglement between a resin component and the surface-treated carbon nanotube can be obtained, with the result that a resin interface can be effectively formed.

(Polyamide Resin Composition (3-1))

A preferred aspect of the third embodiment is directed to a polyamide resin composition (3-1) containing a surface-treated carbon nanotube in which the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum is 0.1 to 0.9, and a polyamide resin; in which a peak temperature of the cooling crystallization temperature measured by differential scanning calorimetry (DSC) is 240° C. or less, and a specific strength of ISO36 Type3 dumbbell at 120° C. is 35 MPa or more.

As is described in the first embodiment, when a surface treatment is performed with an organic acid or a polymer having an organic acid as a polymerization unit, a crystalline carbon nanotube is preferably used in view of a surface treatment reaction. Also in this respect, the ratio (Id/Ig) of the peak area (Id) of the band having the range of 1335 and 1365 cm$^{-1}$ to the peak area (Ig) of the band having the range of 1565 to 1600 cm$^{-1}$ in the Raman scattering spectrum of the carbon nanotube before the surface treatment, to be used in the polyamide resin composition (3-1) is preferably 0.1 to 0.9, more preferably 0.1 to 0.6 and further preferably 0.1 to 0.4.

In the polyamide resin composition (3-1), the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum of the surface-treated carbon nanotube of the embodiment is preferably 0.1 to 0.9, more preferably 0.1 to 0.6 and further preferably 0.1 to 0.4. When at least an organic acid or a polymer having an organic acid as a polymerization unit is used in the surface treatment, the above ratio (Id/Ig) of the surface-treated carbon nanotube to be obtained is preferably controlled to fall within the above range. If the above ratio (Id/Ig) is controlled to fall within the above range, the increase in a point defect and a defective edge of a crystal, etc. of the carbon nanotube can be suppressed, with the result that the strength and rigidity of the polyamide resin composition at high temperature can be further improved. In addition, since crystallization can be facilitated, the solidification time during molding can be reduced, shortening a molding cycle.

(Polyamide Resin Composition (3-2))

Another preferred aspect of the third embodiment is directed to a polyamide resin composition (3-2) containing a surface-treated carbon nanotube in which the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum is 1.0 to 2.0, and a polyamide resin; in which a peak temperature of the cooling crystallization temperature measured by differential scanning calorimetry (DSC) is 234° C. or less, and a specific strength of ISO36 Type3 dumbbell at 120° C. is 35 MPa or more.

As is described in the first embodiment, when a surface treatment is performed with an inorganic acid, an amorphous carbon nanotube is preferably used in view of a surface treatment reaction. Also in this respect, the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum of the carbon nanotube before the surface treatment, to be used in the polyamide resin composition (3-2) is preferably 1.0 to 2.0, more preferably 1.2 to 2.0 and further preferably 1.4 to 2.0.

In the polyamide resin composition (3-2), the ratio (Id/Ig) of the peak area (Id) of the band having the range of 1335 to 1365 cm$^{-1}$ to the peak area (Ig) of the band having the range of 1565 to 1600 cm$^{-1}$ in the Raman scattering spectrum of the surface-treated carbon nanotube is preferably 1.0 to 2.0, more preferably 1.2 to 2.0 and further preferably 1.4 to 2.0. When at least an inorganic acid is used in the surface treatment, the above ratio (Id/Ig) of the surface-treated carbon nanotube to be obtained is preferably controlled to fall within the above range. If the above ratio (Id/Ig) is the aforementioned lower limit value or more, defective portions can be allowed to interact with a resin, further improving the strength. In contrast, if the above ratio (Id/Ig) is the aforementioned upper limit or less, the increase in a point defect and a defective edge of a crystal, etc. of the carbon nanotube can be more or less suppressed, with the result that the strength and toughness of the polyamide resin composition can be further improved. In addition, since crystallization can be facilitated, favorable surface appearance of the molded product can be obtained It is preferable that the polyamide resin compositions (3), (3-1) and (3-2) of the embodiment further contain, if necessary, additives that can react with a polyamide resin and/or a surface-treated carbon nanotube. As such additives, those described in the first embodiment and the second embodiment can be used.

The polyamide resin compositions (3), (3-1) and (3-2) of the embodiment may contain, if necessary, a resin other than a polyamide and a rubber component as long as the object of the embodiment is not damaged. As the resin and rubber component, those described in the first embodiment and the second embodiment can be used.

The molded articles of the polyamide resin compositions (3), (3-1) and (3-2), since they have strength and toughness at high temperature, a nucleating additive suppression effect and a small amount of deformation of the resultant molded article, can be used in various uses. Uses of the molded articles are not particularly limited. The molded articles can be preferably used in a wide variety of uses including, for example, automotive parts, electrical parts, electronic parts, portable electronic device parts, machine/industrial parts, business machine parts and aviation/space parts.

Fourth Embodiment

Now, the fourth embodiment will be described. Note that descriptions on the same contents as in the first embodiment to third embodiment will be appropriately omitted.

The polyamide resin composition (4) of the embodiment is a polyamide resin composition containing a surface-treated carbon nanotube and a polyamide resin, in which the content of an organic substance attached to the surface-treated carbon nanotube, which is obtained by an elution treatment of the polyamide resin composition with hexafluoroisopropanol, is 2 to 10 mass %. The above polyamide resin composition has excellent physical properties (tensile strength at 120° C., specific strength and fracture elongation) due to the presence of the interfacial phase sufficiently formed between the carbon nanotube and a polyamide resin which is a base resin, and further has an excellent creep property at high temperature. The interfacial phase can also have a function of adhering the polyamide and the carbon nanotube.

The surface-treated carbon nanotube having a deposit of an organic substance, and obtained by an elution treatment of the polyamide resin composition (4) with hexafluoroisopropanol is an insoluble component obtained by removing soluble components such as a polyamide resin, from the polyamide resin composition. The insoluble component contains not only a surface-treated carbon nanotube (surface-treated carbon nanotube containing not only a "bound substance" but also a "deposit," as is described in the first embodiment) but also an interfacial phase formed by some interaction (e.g., chemical binding) between the bound substance as well as the deposit on the CNT surface and the polyamide. This conceivably suggests that the polyamide itself is partly taken into the interfacial (adhesive) phase. In the polyamide resin composition (4), the content of the organic substance is an index showing the amount of interfacial phase formed between the carbon nanotube and the polyamide present in the polyamide resin composition (4). The interfacial phase can also have a function of adhering the polyamide and the carbon nanotube.

The organic substance preferably contains a compound represented by any one of formula (1) to formula (4):

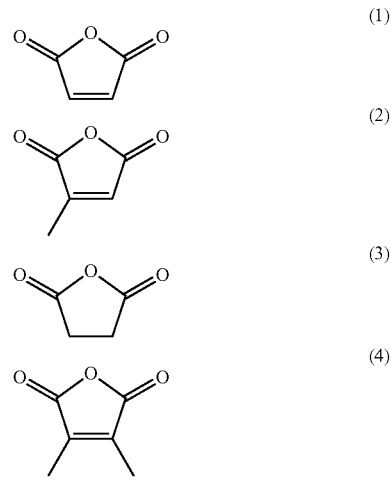

The amount of organic substances corresponds to the amount of interfacial (adhesive) phase formed between the carbon nanotube and the polyamide. Accordingly, detecting the compounds represented by formula (1) to formula (4) in the interfacial phase means that the interfacial phase can be further formed by facilitating take-up of a polyamide by the bound substance on the carbon nanotube surface. The interfacial phase can also have a function of adhering the polyamide and the carbon nanotube. Owing to this, further excellent physical properties are obtained.

The surface sulfur concentration of a surface-treated carbon nanotube having a deposit of an organic substance and measured by X-ray photoelectron spectroscopy is preferably 0.1 atm %.

The surface nitrogen concentration of the surface-treated carbon nanotube having a deposit of an organic substance and measured by X-ray photoelectron spectroscopy is preferably 1 to 15 atm %.

In a resin composition (polyamide resin composition) containing the surface-treated carbon nanotube of the embodiment and a polyamide resin, the interfacial phase formed between the polyamide resin and the carbon nanotube will be described. The amount of interfacial phase is increased by a surface treatment. The amount of interfacial phase to be formed is greatly influenced by the surface treatment. More specifically, the surface treatment is preferably performed by a chemical species having a high reactivity with the polyamide resin since the amount of interfacial phase to be formed increases. In view of this, if a carbon nanotube is used in a polyamide resin composition, the surface treatment of the carbon nanotube is preferably performed with at least one selected from the group consisting of a maleic anhydride, a poly(acrylic acid), a poly(acrylic acid-co-maleic acid) copolymer, an ethylene-maleic anhydride copolymer and a styrene-maleic anhydride copolymer.

The amount of interfacial phase tends to be increased by performing a surface treatment in the absence of a solvent.

Examples of such a surface treatment condition include a surface treatment condition using a maleic anhydride in the absence of a solvent.

The amount of interfacial phase can be controlled not only by conditions of the surface treatment but also by conditions of a post treatment (washing method, etc.) performed after the surface treatment. For example, in the case of a surface treatment using a maleic anhydride in the absence of a solvent, the amount of surface treatment and the amount of interfacial phase as mentioned above tend to be increased by using a non-polar solvent (toluene, etc.) as a washing solvent rather than using a polar solvent (methanol, etc.). As a result, high-temperature physical properties tend to more improve. The reason for this is not known; however it is conceivable that not only the bound substance layer on the surface of a carbon nanotube but also the deposit layer is greatly involved in formation of the interface with a polyamide resin. Consequently, it is considered that the interface reinforced by the bound substance layer is further reinforced.

The interface between a carbon nanotube and a polyamide resin can be quantified, for example, by dissolving a carbon nanotube/polyamide composition in a polyamide soluble solvent (hexafluoroisopropanol, etc.), thereby removing a polyamide component, collecting insoluble components, i.e., carbon nanotube and the interfacial phase, heating them at 600° C., thereby pyrolytically removing the interfacial phase alone, and measuring a thermal reduction amount in this step to quantify the interfacial phase.

More specifically, the content of an organic substance is preferably 2 to 10 mass %, more preferably 2 to 8 mass %, further preferably 2.5 to 7.5 mass %, still further preferably 3 to 7.0 mass % and further more preferably 3.5 to 6.0 mass %. If the content of an organic substance is controlled so as to fall within the above range, physical properties and molding processability further improve.

The surface sulfur concentration of a surface-treated carbon nanotube having a deposit of an organic substance and measured by X-ray photoelectron spectroscopy is preferably less than 0.1 atm %. The surface sulfur concentration can be measured by detecting sulfur atoms on the surface of the residue (a carbon nanotube with the interfacial phase) by an X-ray photoelectron spectrometer (XPS). This value tends to increase when a sulfur-containing compound is used for the surface treatment.

The presence or absence of a reaction product derived from a polyamide in the interfacial phase (a phase formed in the boundary between the polyamide and the carbon nanotube) in the surface treatment can be confirmed by determining the concentration of nitrogen atoms (when a nitrogen-containing compound is not used for a surface treatment). The interfacial phase also has a function of adhering the polyamide and the carbon nanotube. The nitrogen atoms of such an interfacial phase can be measured and the reaction product derived from a polyamide is preferably involved in the interfacial phase in view of interface strength. The effect of a surface treatment is confirmed by evaluating how high the surface nitrogen concentration of a polyamide resin composition containing a surface-treated carbon nanotube compared to a polyamide resin composition containing a carbon nanotube to which no surface treatment is applied.

In view of this, the surface nitrogen concentration of a surface-treated carbon nanotube having a deposit of an organic substance and determined by X-ray photoelectron spectroscopy is preferably 1 to 15 atm %, more preferably 2 to 15 atm % and further preferably 3 to 15 atm %. If the surface nitrogen is sufficiently present, a crystalline carbon nanotube tends to have further satisfactory physical properties. Thus, the ratio (Id/Ig) of the peak area (Id) of the band having the range of 1335 to 1365 $cm^{-1}$ to the peak area (Ig) of the band having the range of 1565 to 1600 $cm^{-1}$ in the Raman scattering spectrum of the surface-treated carbon nanotube, is preferably 0.1 to 2.0, more preferably 0.1 to 0.9, further preferably 0.1 to 0.5 and still further preferably 0.1 to 0.3.

It is preferable that the polyamide resin composition (4) of the embodiment further contains additives that react with a polyamide resin and/or a surface-treated carbon nanotube, as necessary. As such additives, those described in the first to third embodiments can be used.

The polyamide resin composition (4) of the embodiment may contain, as necessary, a resin other than a polyamide and a rubber component as long as the object of the embodiment is not damaged. As the resin and rubber component, those described in the first to third embodiments can be used.

The molded article of the polyamide resin composition (4), since it has strength and toughness at high temperature and a nucleating additive suppression effect and a small amount of deformation of the resultant molded article, can be used in various uses. Uses of the molded articles are not particularly limited. The molded articles can be preferably used in a wide variety of uses including, for example, automotive parts, electrical parts, electronic parts, portable electronic device parts, machine/industrial parts, business machine parts and aviation/space parts.

EXAMPLES

Now, the present invention will be more specifically described by way of Examples and Comparative Examples; however, the present invention is not limited by these examples.

Experiment 1

(Measurement Method)

X-Ray Photoelectron Spectroscopy (XPS)

Using an X-ray photoelectron spectrometer (X-ray photoelectron spectroscopy, XPS; "ESCALAB 250," manufactured by Thermo Fisher), the surface oxygen concentration of a carbon nanotube was measured. First, the carbon nanotube was placed on a sample dish of 2 mmφ×0.3 mm in depth and subjected to measurement. The surface oxygen concentration of the carbon nanotube was measured based on the following measurement conditions. The types of elements in the surface of the carbon nanotube detected by XPS were oxygen, carbon and sulfur. Note that the surface sulfur concentration was calculated based on XPS. Note that "less than detection limit" in Tables means that detection could not be made since the concentration was less than a detection limit.

<Measurement Conditions>

Excitation source: monochroic AlKα 15 kV×10 mA

Analysis size: about 1 mm (shape is ellipse)

Photoelectron drawing angle: 0° (perpendicular to sample surface)

Take-up region

Survey scan: 0 to 1,100 eV

Narrow scan: C1s, O 1s

Pass Energy

Survey scan: 100 eV

Narrow scan: 20 eV

Detection limit: 0.1 atm %

<Curve Fitting of C1s Spectrum>

Curve fitting of C1s spectrum was performed. With respect to carbon nanotube components serving as a base, curve fitting was performed as to the C1s spectrum of untreated carbon nanotube to obtain configuration parameters.

Amount of Weight Loss

Measurement was performed by "TG/DTA220" manufactured by Seiko Instruments Inc. The temperature of the samples was raised from 30° C. to 600° C. at a temperature raising rate of 10° C./minute in a nitrogen atmosphere (flow rate: 250 mL/minute) and the amount of the weight loss of the samples at 600° C. was measured.

Raman Scattering Spectroscopy

Microscopic laser Raman analyzer ("Almega XR," manufactured by Thermo Fisher Scientific K.K.) was used. First, samples were dried in a vacuum dry oven at 80° C. for 12 hours to prepare measurement samples. Then, the measurement samples were subjected to Raman scattering spectroscopy to determine the ratio (Id/Ig) of the peak area (Id) of a spectrum having a peak top between 1335 and 1365 cm$^{-1}$ to the peak area (Ig) of a spectrum having a peak top between 1565 to 1600 cm$^{-1}$. The peak area was calculated by curve fitting of the peak strength. Measurement was performed three times in total and an arithmetic average of three measurement values was calculated. Note that with respect to the above ratio (Id/Ig), the ratio (Id/Ig) of a carbon nanotube whose surface was not treated and the ratio (Id/Ig) of a surface-treated carbon nanotube were individually determined and an absolute value (ΔId/Ig) of the difference between them was calculated. Then, if the absolute value (ΔId/Ig) was small, the surface fractures were determined to be few.

Detection of Bound Substance to Carbon Nanotube (Pyrolysis-Gas Chromatography/Mass Spectroscopy (Py-GC/MS))

A gas chromatography mass spectrometer (GC/MS apparatus; "Automass SUN," manufactured by JEOL Ltd.), which has a pyrolysis apparatus ("Py 2010D," manufactured by Frontier Laboratories Ltd.) connected to the sample inlet portion thereof, was used for measurement. First, 10 mL of methanol was added to 500 mg of a surface-treated carbon nanotube and stirred for 30 minutes. The solution was filtered under aspiration to separate the surface-treated carbon nanotube and a filtrate. The operation was repeated five times to obtain the surface-treated carbon nanotube filtered. The surface-treated carbon nanotube filtered was dried under vacuum at 80° C. for 12 hours to obtain a surface-treated carbon nanotube sample. This sample was subjected to measurement by pyrolysis-gas chromatography/mass spectroscopy (Py-GC/MS) to analyze components of the surface-treated carbon nanotube. In Py-GC/MS, the presence or absence of the compounds represented by formula (1) to formula (4) was confirmed. Note that in the column of "formula (5) and formula (6)" of the "deposit (surface treatment)" of Tables, the molecular weight of the peak top detected was listed.

<Py-GC/MS Measurement Conditions>

Pyrolysis apparatus: "Py 2010D," manufactured by Frontier Laboratories Inc.

Heating temperature: 600° C.

Interface temperature: 320° C.

Heating atmosphere: He

GC/MS apparatus: "Automass SUN," manufactured by JEOL Ltd.

Column: DB-1 (0.25 mm i.d.×30 m) liquid phase thickness: 0.25 μm column temperature: 40° C. (5 minutes)→(temperature raising rate: 20° C./minute)→320° C. (retention time: 11 minutes)

Injection port temperature: 320° C.

Injection method: Sprit method (sprit ratio 1/10)

Ion source: EI, temperature of 240° C., I/F 300° C., PM=400 V

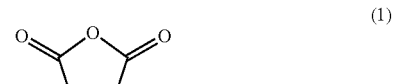

(1)

(2)

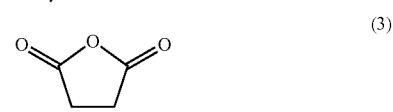

(3)

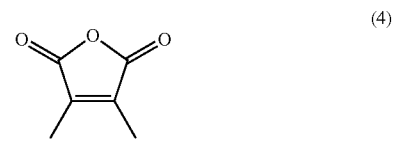

(4)

Detection of Deposit on Carbon Nanotube (Carbon Nuclear Magnetic Resonance Spectroscopy ($^{13}$C-NMR))

$^{13}$C-NMR measurement was performed by using a nuclear magnetic resonance apparatus ("Avance 600," manufactured by Bruker BioSpin K.K.). First, 10 mL of methanol was added to 500 mg of a surface-treated carbon nanotube and stirred for 30 minutes. The solution was filtered under aspiration to separate the surface-treated carbon nanotube and a filtrate. This operation was repeated five times and the filtrates were collected. Methanol was distilled away from the filtrate by an evaporator. The filtrate was dried in air to obtain a dry product. The dry product was dissolved in deuterated methanol to prepare a measurement sample, which was subjected to $^{13}$C-NMR measurement. In the $^{13}$C-NMR measurement, the presence or absence of the compounds represented by formula (5) and formula (6) was confirmed. The sample in which at least one of the compounds was detected was subjected to molecular weight measurement performed by GPC described in the next section and the peak molecular weight was listed in Tables. If a plurality of peaks were observed, a plurality of peak molecular weights were listed in Tables. The case where no peaks were detected was indicated as "none."

<$^{13}$C-NMR Measurement Conditions>

Nucleus observed: $^{13}$C

Observation frequency: 150.91 MHz

Pulse program: zgig30 (quantification mode)

Flip angle: 30°

Measurement temperature: Room temperature

Cumulated number: 6000 times

Chemical shift base: Deuterated methanol 49 ppm

Test tube: 5 mmφ

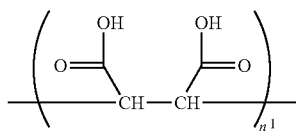

(5)

where $n^1$ is an integer of 2 to 400.

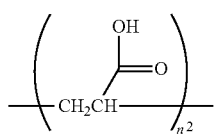

(6)

where $n^2$ is an integer of 2 to 650.

GPC Measurement

In the above "carbon nuclear magnetic resonance spectroscopy ($^{13}$C-NMR)," the weight average molecular weight of the obtained dry product was measured. To the dry product, an eluent (N,N-dimethylacetamide: DMAc) was added. In this manner, a sample was prepared so as to have a concentration of 1.0 mg/mL, and allowed to stand still overnight. This sample was filtered by a 0.45 micron filter and the obtained filtrate was used as a measurement sample. The weight average molecular weight (PMMA equivalent) of the obtained measurement sample was measured by a GPC apparatus ("HLC-8220GPC," manufactured by Tosoh Corporation). The peak molecular weight was listed in Tables. If a plurality of peaks were observed, a plurality of peak molecular weights were listed in Tables.

Measurement Conditions

Column: TSKgel SuperAWM-H (6.0 mm ID×15 cm), 2 columns

Oven: 40° C.

Eluent: DMAc (10 mmol LiBr) 0.6 mL/min

Detector: RI

Calibration curve: PMMA

Extrudability Evaluation 90 parts by mass of Polyamide 66 and 10 parts by mass of carbon nanotube were supplied in a kneader ("XPlore:" a kneader equipped with a small kneading extruder and a molding machine; manufactured by Royal DSM) and melt extrusion was performed. Then, extrudability was evaluated. The melt extrusion conditions were a melting temperature: 290 to 320° C., rotation number: 100 rpm and kneading time: 2 minutes. A thin carbon steel was attached to a screw surface so as not to impede kneading and kneading was performed. The state of the carbon steel before and after the kneading was observed by a stereoscopic microscope to evaluate abrasion and the presence or absence of metal corrosion of the screw after the melt-kneading.

◯ . . . Neither abrasion nor metal corrosion of a screw was observed.

X . . . At least either abrasion or metal corrosion of a screw was observed.

Viscosity of Formic Acid Solution

The melt viscosity of formic acid was measured in accordance with JIS K6810.

First, polyamide 66 (trade name: "Leona 1300S," manufactured by Asahi Kasei Chemicals Corporation) and a carbon nanotube were blended in accordance with the ratios shown in Tables to prepare polyamide resin compositions. The polyamide resin composition containing polyamide 66 and the carbon nanotube was kneaded by a kneader ("XPlore:" a kneader equipped with a small kneading extruder and a molding machine; manufactured by Royal DSM) to prepare dumbbell test pieces of ISO36 Type3 (size of the middle parallel portion of the dumbbell between the chucks: length 16 mm×width 4 mm×thickness 2 mm). To describe more specifically, the polyamide resin and the carbon nanotube were supplied in the kneader, kneaded at a kneader-screw rotation number of 100 rpm and a kneading temperature of 300° C. for 2 minutes and injected at a mold temperature of 80° C. and an injection pressure of 11 bar (30 seconds) to obtain the dumbbell test pieces. The obtained dumbbell test pieces were cut into pieces by a nipper in order to facilitate dissolution and dissolved in formic acid (concentration of 90%) such that the content of the polyamide resin was 8.4 mass % to prepare a formic acid solution (a formic acid solution of the polyamide resin composition).

Subsequently, a formic acid solution of a polyamide resin containing 8.4 mass % of polyamide 66 was prepared. The formic acid solution of a polyamide resin contained no carbon nanotube and used as a blank. The formic acid melt viscosity of the formic acid solution of a polyamide resin was 48.

Amount of Remaining Organic Substance (TGA)

First, polyamide 66 (trade name: "Leona 1300S," manufactured by Asahi Kasei Chemicals Corporation) and a carbon nanotube were blended in accordance with the ratios shown in Tables to prepare polyamide resin compositions. The polyamide resin composition containing polyamide 66 and the carbon nanotube was kneaded by a kneader ("XPlore:" a kneader equipped with a small kneading extruder and a molding machine; manufactured by Royal DSM) to prepare dumbbell test pieces of ISO36 Type3 (size of the middle parallel portion of the dumbbell between the chucks: length 16 mm×width 4 mm×thickness 2 mm).

The polyamide resin and the carbon nanotube were supplied in the kneader, kneaded at a kneader-screw rotation number of 100 rpm and a kneading temperature of 300° C. for 2 minutes and injected at a mold temperature of 80° C. and an injection pressure of 11 bar (30 seconds) to obtain the dumbbell test pieces.

About 4 g of the obtained dumbbell test pieces were cut into pieces by a nipper. To the test pieces, about 100 mL of HFIP (hexafluoroisopropanol) was added. The mixture was stirred by a stirrer at room temperature for about 2 hours. After visually confirming that the polyamide was almost completely dissolved, the solution was transferred to centrifuge tubes and centrifuged by a centrifugal machine (10000 rpm, 30 minutes). After the supernatant was discarded, about 100 mL of fresh HFIP was added. The mixture was stirred in the same manner by a stirrer for 2 hours, washed and again subjected to centrifugation. The supernatant was discarded. The washing with HFIP was performed five times. After washing with HFIP, about 100 mL of ethanol was added and stirred in the same manner by a stirrer for 2 hours, washed and again subjected to centrifugation and then, the supernatant was discarded. Washing with ethanol was performed three times. After washing, the precipitate was dried at 60° C. overnight by a vacuum dryer. In this manner, soluble components such as a polyamide were eluted from the composition by the elution treatment with HFIP to take out about 120 mg of insoluble components (carbon nanotube and the remaining organic substances (interfacial phase)). The thermal reduction amount at 600° C. was measured by use of "TG/DTA220," manufactured by Seiko Instruments Inc. The temperature of the sample was raised from 30° C. to 600° C. at a temperature raising rate of 10° C./minute in a nitrogen atmosphere (flow rate: 250 mL/minute) and the amount of the weight loss of the sample at 600° C. was measured.

Measurement of Peak Temperature of Cooling Crystallization Temperature Measured by Differential Scanning Calorimetry (DSC)

Differential scanning calorimetry (DSC) was performed by use of Diamond DSC apparatus manufactured by PerkinElmer, Inc. in accordance with JIS-K7121 at a temperature raising rate of 20° C./minute.

Preparation of Test Piece

Using a kneader ("XPlore" (a kneader equipped with a small kneading extruder and a molding machine) manufactured by Royal DSM), dumbbell test pieces of ISO36 Type3 (size of the middle parallel portion of the dumbbell between the chucks: length 16 mm×width 4 mm×thickness 2 mm) were prepared. To describe more specifically, the polyamide resin and the carbon nanotube were supplied in the kneader and kneaded at a kneader-screw rotation number of 100 rpm and a kneading temperature of 300° C. for 2 minutes and injected at a mold temperature of 80° C. and an injection pressure of 11 bar (30 seconds) to obtain the dumbbell test pieces.

Tension Test

First, dumbbell test pieces of ISO36 Type3 (size of the middle parallel portion of the dumbbell between the chucks: length 16 mm×width 4 mm×thickness 2 mm) were prepared. Using a tensile tester ("Autograph AG-5000D" manufactured by Shimadzu Corporation), temperature was raised up to 120° C., and then the dumbbell was placed and allowed to stand still for 30 minutes. The tensile strength and tensile elongation of the dumbbell were determined at a distance between chucks of 25 mm and a tension rate of 50 mm/minute. Furthermore, the tensile elongation was calculated as the ratio of elongation (displacement) when broken relative to the distance between chucks.

Provided that the density of the polyamide was 1.14 g/cm$^3$ and the density of the carbon nanotube was 2.00 g/cm$^3$, the density of the polyamide resin composition was calculated. The tensile strength was divided by the density of the polyamide resin composition to calculate a specific strength.

Creep Test

Using a creep tester ("CP6-L-250" manufactured A&D Company Limited), temperature was raised up to 120°. In the tester, the dumbbell was placed and allowed to stand still for 2 hours. The time (seconds) required until the dumbbell elongated and reached a deformation rate of 15% under the conditions: a distance between chucks of 25 mm and a stress of 30 MPa was measured.

TABLE 1

| CNT | | Raw material A | Raw material B | Raw material C |
|---|---|---|---|---|
| Fiber diameter | φ (nm) | 150 | 150 | 15 |
| XPS | Oxygen (atm %) | 0.2 | 0.4 | 0.3 |
|  | Sulfur (atm %) | Less than detection limit | Less than detection limit | Less than detection limit |
| TGA | Weight loss (%) | 0.1 | 0.1 | 0.1 |
| Raman scattering spectroscopy | Id/Ig | 0.1 | 1.4 | 1.2 |

Example 1-1 (Carbon Nanotube Whose Surface was Treated with a Maleic Anhydride)

In a 2000-mL three-necked flask, 10 g of carbon nanotube A and 200 g of a maleic anhydride (manufactured by Wako Pure Chemical Industries, Ltd.) were supplied. Ultrasonic wave was applied for 10 minutes. While stirring by a stirrer chip, the mixture was bubbled with argon for 30 minutes. Thereafter, the mixture was heated to 180° C. and a reaction was performed for 3 hours. After the reaction, the reaction solution was cooled to room temperature. To the reaction solution, toluene was added and the mixture was filtered under aspiration. Toluene was further added, and washing and filtration were repeated four times in total. After filtration, the carbon nanotube was dried under vacuum at 80° C. for 12 hours to obtain the carbon nanotube. Note that the carbon nanotube was a carbon nanotube whose surface was treated with a maleic anhydride in a liquid phase and in the absence of a solvent.

Example 1-2 (Carbon Nanotube Whose Surface was Treated with a Maleic Anhydride)

A carbon nanotube was obtained in the same manner as in Example 1-1 except the conditions shown in the following table. Note that the carbon nanotube was a carbon nanotube whose surface was treated with a maleic anhydride in a liquid phase and in the absence of a solvent.

Example 1-3 (Carbon Nanotube Whose Surface was Treated with a Maleic Anhydride)

A carbon nanotube was obtained in the same manner as in Example 1-1 except the conditions shown in the following table. Note that the carbon nanotube was a carbon nanotube whose surface was treated with a maleic anhydride in a liquid phase and in the absence of a solvent.

Example 1-4 (Carbon Nanotube Whose Surface was Treated with a Maleic Anhydride)

A carbon nanotube was obtained in the same manner as in Example 1-1 except the conditions shown in the following table. Note that the carbon nanotube was a carbon nanotube whose surface was treated with a maleic anhydride in a liquid phase and in the absence of a solvent.

Example 1-5 (Carbon Nanotube Whose Surface was Treated with a Maleic Anhydride)

A carbon nanotube was obtained in the same manner as in Example 1-1 except the conditions shown in the following table. Note that the carbon nanotube was a carbon nanotube whose surface was treated with a maleic anhydride in a liquid phase and in the absence of a solvent.

Example 1-6 (Carbon Nanotube Whose Surface was Treated with a Maleic Anhydride)

A carbon nanotube was obtained in the same manner as in Example 1-1 except the conditions shown in the following table. Note that the carbon nanotube was a carbon nanotube whose surface was treated with a maleic anhydride in a liquid phase and in the absence of a solvent.

Example 1-7 (Carbon Nanotube Whose Surface was Treated with a Maleic Anhydride)

A carbon nanotube was obtained in the same manner as in Example 1-1 except the conditions shown in the following table. Note that the carbon nanotube was a carbon nanotube whose surface was treated with a maleic anhydride in a liquid phase and in the absence of a solvent.

Example 1-8 (Carbon Nanotube Whose Surface was Treated with a Maleic Anhydride)

A carbon nanotube was obtained in the same manner as in Example 1-1 except the conditions shown in the following table. Note that the carbon nanotube was a carbon nanotube whose surface was treated with a maleic anhydride in a liquid phase and in the absence of a solvent.

Example 1-9 (Carbon Nanotube Whose Surface was Treated with a Maleic Anhydride)

A carbon nanotube was obtained in the same manner as in Example 1-1 except the conditions shown in the following table. Note that the carbon nanotube was a carbon nanotube whose surface was treated with a maleic anhydride in a liquid phase and in the absence of a solvent.

Example 1-10 (Carbon Nanotube Whose Surface was Treated with a Maleic Anhydride)

In a 2000-mL autoclave, 10 g of carbon nanotube B, 280 mL of toluene as a solvent and 56 g of a maleic anhydride were supplied. While stirring by a mixing impeller, the mixture was heated to 180° C. and a reaction was performed for 24 hours. After the reaction, the reaction solution was cooled to room temperature. To the reaction solution, toluene was added and the mixture was filtered under aspiration. Toluene was further added and washing and filtration were repeated four times in total. After filtration, the carbon nanotube was dried under vacuum at 80° C. for 12 hours to obtain the carbon nanotube. Note that the carbon nanotube was a carbon nanotube whose surface was treated with a maleic anhydride in a liquid phase.

Example 1-11 (Carbon Nanotube Whose Surface was Treated with a Maleic Anhydride)

In a 2000-mL autoclave, 10 g of carbon nanotube A, 280 mL of toluene as a solvent and 56 g of a maleic anhydride were supplied. While stirring by a mixing impeller, the mixture was heated to 180° C. and a reaction was performed for 24 hours. After the reaction, the reaction solution was cooled to room temperature. To the reaction solution, toluene was added and the mixture filtered under aspiration. Toluene was further added and washing and filtration were repeated four times in total. After filtration, the carbon nanotube was dried under vacuum at 80° C. for 12 hours to obtain the carbon nanotube. Note that the carbon nanotube was a carbon nanotube whose surface was treated with a maleic anhydride in a liquid phase.

Example 1-12 (Carbon Nanotube Whose Surface was Treated with a Maleic Anhydride)

A carbon nanotube was obtained in the same manner as in Example 1-11 except that the total number of times of washing and filtration of a carbon nanotube after the reaction was changed to ten. Note that the carbon nanotube was a carbon nanotube whose surface was treated with a maleic anhydride in a liquid phase.

Example 1-13 (Carbon Nanotube Whose Surface was Treated with Hydrogen Peroxide Solution)

In a 500-mL egg-plant flask, 10 g of carbon nanotube B and 350 mL of hydrogen peroxide solution (a 30% aqueous solution, manufactured by Wako Pure Chemical Industries, Ltd.) were supplied. The mixture was heated to 90° C. while stirring by a mixing impeller and a reaction was performed for 12 hours. After the reaction, the reaction solution was cooled to room temperature. To the reaction solution, ion exchange water was added. The mixture was filtered under aspiration. Ion exchange water was further added and washing and filtration were repeated until the filtrate was neutralized (until the pH value did not virtually change). After the filtration, the carbon nanotube was dried under vacuum at 80° C. for 12 hours to obtain the carbon nanotube. Note that the carbon nanotube was a carbon nanotube whose surface was treated with hydrogen peroxide solution in a liquid phase.

Example 1-14 (Carbon Nanotube Whose Surface was Treated with Citric Acid)

In a 500-mL autoclave, 20 g of carbon nanotube A and 200 g of citric acid (manufactured by Wako Pure Chemical Industries, Ltd.) were supplied. While stirring by a mixing impeller, the mixture was bubbled with nitrogen for 30 minutes. Then, the mixture was heated to 200° C. and a reaction was performed for 5 hours. After the reaction, the reaction solution was cooled to room temperature and warm water of 70° C. was added to the reaction solution. The reaction solution was filtered under aspiration. Warm water of 70° C. was further added and washing and filtration were repeated until the filtrate was neutralized (until the pH value did not virtually change). After the filtration, the carbon nanotube was dried under vacuum at 80° C. for 12 hours to obtain the carbon nanotube. Note that the carbon nanotube was a carbon nanotube whose surface was treated with citric acid in a liquid phase and in the absence of a solvent.

Example 1-15 (Carbon Nanotube Whose Surface was Treated with Citric Acid)

A carbon nanotube was obtained in the same manner as in Example 1-14 except that carbon nanotube A was changed to carbon nanotube B. Note that the carbon nanotube was a carbon nanotube whose surface was treated with citric acid in a liquid phase and in the absence of a solvent.

Example 1-16 (Surface-Activated Carbon Nanotube)

In a heat resistant tube having a gas inlet and a discharge port, carbon nanotube B was placed. Argon gas was allowed to flow in the heat resistant tube for about 30 minutes to replace the atmosphere of the tube with argon. The resultant heat resistant tube was placed in a Lindberg furnace. The furnace was heated up to 300° C. while supplying argon gas and maintained for 30 minutes. Thereafter, the furnace was heated up to 1000° C. at a temperature raising rate of 100° C./min and maintained further for 16 hours. In this manner, the surface of the carbon nanotube was activated. Thereafter, the carbon nanotube was allowed to cool while supplying argon gas and allowed to stand still up to approximately room temperature. Thereafter, a container containing a maleic anhydride (in argon gas) heated to 80° C. was prepared. Argon gas was passed through the molten maleic anhydride and then supplied to the tube and the reaction was directly performed for 6 hours. Finally, argon gas was replaced to terminate the reaction. After the reaction, the carbon nanotube was taken out and dried under vacuum at 100° C. for 12 hours to obtain a surface-treated carbon nanotube.

Example 1-17 (Carbon Nanotube Whose Surface was Treated with a Maleic Anhydride)

In a 2000-mL three-necked flask, 10 g of carbon nanotube A, 200 g of a maleic anhydride (manufactured by Wako Pure Chemical Industries Ltd.) and 2-2'-azobisisobutyronitrile (AIBN, manufactured by Tokyo Chemical Co., Ltd.) as a radical initiator were supplied. Ultrasonic wave was applied for 10 minutes. While stirring by a stirrer chip, the mixture was bubbled with argon for 30 minutes. Thereafter, the mixture was heated to 120° C. and a reaction was performed for 6 hours. After completion of the reaction, the reaction solution was cooled to room temperature. While toluene was poured into the reaction solution, the reaction solution was filtered under aspiration. 300 mL of toluene was further added and washing and filtration were repeated four times in total. After filtration, the carbon nanotube was dried under vacuum at 80° C. for 12 hours to obtain the carbon nanotube. Note that the carbon nanotube was a carbon nanotube whose surface was treated with a maleic anhydride in a liquid phase and in the absence of a solvent.

Example 1-18 (Carbon Nanotube Whose Surface was Treated with an Ethylene-Maleic Anhydride Copolymer)

In a 500-mL egg-plant flask, 10 g of carbon nanotube A, 200 g of 1-methyl-2-pyrrolidone as a solvent and 6 g of an ethylene-maleic anhydride copolymer (trade name: "ZeMac E400," manufactured by Vertellus Specialties Inc.; weight average molecular weight: 400,000, ethylene:maleic anhydride=1:1 (mole ratio)) were supplied. While stirring by a mixing impeller, the mixture was bubbled with nitrogen for 30 minutes. The mixture was heated to 180° C. and a reaction was performed for 6 hours. After the reaction, the reaction solution was cooled to room temperature. Acetone was added to the reaction solution and the mixture was filtered under aspiration. 200 mL of acetone was further added, and washing and filtration were repeated four times in total. After filtration, the carbon nanotube was dried under vacuum at 80° C. for 12 hours to obtain carbon nanotube K. Note that the carbon nanotube was a carbon nanotube whose surface was treated with the ethylene-maleic anhydride copolymer in a liquid phase.

Example 1-19 (Carbon Nanotube Whose Surface was Treated with a Poly(Acrylic Acid))

In a 500-mL three-necked flask, 10 g of carbon nanotube A, 200 g of 1-methyl-2-pyrrolidone (manufactured by Wako Pure Chemical Industries, Ltd.) as a solvent and 6 g of poly(acrylic acid) (manufactured by Aldrich Chemical Company; weight average molecular weight: 1800) were supplied. Ultrasonic wave was applied for 10 minutes. While stirring by a stirrer chip, the mixture was bubbled with argon for 30 minutes. Thereafter, the mixture was heated to 180° C. and a reaction was performed for 6 hours. After the reaction, the reaction solution was cooled to room temperature. To the reaction solution, acetone was added and the mixture was filtered under aspiration. Acetone was further added and washing and filtration were repeated four times in total. After filtration, the carbon nanotube was dried under vacuum at 80° C. for 12 hours to obtain the carbon nanotube. Note that the carbon nanotube was a carbon nanotube whose surface was treated with a poly(acrylic acid) in a liquid phase.

Example 1-20 (Carbon Nanotube Whose Surface was Treated with Poly(Acrylic Acid-Co-Maleic Acid))

In a 500-mL three-necked flask, 10 g of carbon nanotube A, 200 g of 1-methyl-2-pyrrolidone (manufactured by Wako Pure Chemical Industries, Ltd.) as a solvent and 12 g of a poly(acrylic acid-co-maleic acid) copolymer (weight average molecular weight: 3000) were supplied. Ultrasonic wave was applied for 10 minutes. While stirring by a stirrer chip, the mixture was bubbled with argon for 30 minutes. Thereafter, the mixture was heated to 180° C. and a reaction was performed for 6 hours. After the reaction, the reaction solution was cooled to room temperature. To the reaction solution, acetone was added and the mixture was filtered under aspiration. Acetone was further added and washing and filtration were repeated four times in total. After filtration, the carbon nanotube was dried under vacuum at 80° C. for 12 hours to obtain the carbon nanotube. Note that as the poly(acrylic acid-co-maleic acid), an aqueous solution of a poly(acrylic acid-co-maleic acid) (manufactured by Aldrich Chemical Company) was dried and used. Note that the carbon nanotube was a carbon nanotube whose surface was treated with the poly(acrylic acid-co-maleic acid) in a liquid phase.

Reference Example 1-1 (Carbon Nanotube Whose Surface was not Treated)

A raw-material carbon nanotube A was used as it was.

Comparative Example 1-1 (Carbon Nanotube Whose Surface was Treated with a Mixed Acid of Sulfuric Acid and Nitric Acid)

To a 1000-mL egg-plant flask, 10 g of carbon nanotube A, and 250 mL of a mixed acid solution containing sulfuric acid (manufactured by Wako Pure Chemical Industries, Ltd.; concentration: 96 to 98%) and nitric acid (manufactured by Wako Pure Chemical Industries, Ltd.; concentration: 69 to 70%) in a volume ratio of 1:3, were supplied. While stirring by a stirrer chip, the mixture was heated to 70° C. and a reaction was performed for 24 hours. After the reaction, the reaction solution was cooled to room temperature. Water was added to the reaction solution and the mixture was filtered under aspiration. Water was further added, washing and filtration were repeated until the filtrate was neutralized (until the pH value did not virtually change). After filtration, the carbon nanotube was dried under vacuum at 80° C. for 12 hours to obtain the carbon nanotube.

Comparative Example 1-2 (Carbon Nanotube Whose Surface was Treated with a Mixed Acid of Sulfuric Acid and Nitric Acid)

A carbon nanotube was obtained in the same manner as in Comparative Example 1-3 except that the washing solvent was changed from water to ion exchange water and washing and filtration was further repeated 20 times in total even if the filtrate was neutralized (until the pH value did not virtually change).

Comparative Example 1-3 (Carbon Nanotube Whose Surface was Treated with Sulfuric Acid)

To a 500-mL egg-plant flask, 10 g of carbon nanotube A and 500 mL of sulfuric acid (manufactured by Wako Pure Chemical Industries, Ltd.; concentration: 96 to 98%) were supplied. While stirring by a mixing impeller, the mixture was heated to 180° C. and a reaction was performed for 24 hours. After the reaction, the reaction solution was cooled to room temperature. Ion exchange water was added to the reaction solution and the mixture was filtered under aspiration. Ion exchange water was further added, washing and filtration were repeated until the filtrate was neutralized (until the pH value did not virtually change). After filtration, the carbon nanotube was dried under vacuum at 80° C. for 12 hours to obtain a carbon nanotube.

Comparative Example 1-4 (Carbon Nanotube Whose Surface was Treated with Nitric Acid)

To a 500-mL egg-plant flask, 10 g of carbon nanotube A and 250 mL of nitric acid (manufactured by Wako Pure Chemical Industries, Ltd.; concentration: 69 to 70%) were supplied. While stirring by a mixing impeller, the mixture was heated to 70° C. and a reaction was performed for 24 hours. After the reaction, the reaction solution was cooled to room temperature. Ion exchange water was added to the reaction solution and the mixture was filtered under aspiration. Ion exchange water was further added, and washing and filtration were repeated until the filtrate was neutralized (until the pH value did not virtually change). After filtration, the carbon nanotube was dried under vacuum at 80° C. for 12 hours to obtain a carbon nanotube.

Comparative Example 1-5 (Carbon Nanotube e Whose Surface was Treated with Hydrogen Peroxide and Sulfuric Acid)

To a 500-mL egg-plant flask, 10 g of carbon nanotube A, 155 mL of hydrogen peroxide solution (manufactured by Wako Pure Chemical Industries, Ltd.; 30% aqueous solution) and 155 mL of sulfuric acid (manufactured by Wako Pure Chemical Industries, Ltd.; concentration 96 to 98%) were supplied. While stirring by a mixing impeller, the mixture was heated to 80° C. and a reaction was performed for 24 hours. After the reaction, the reaction solution was cooled to room temperature. Ion exchange water was added to the reaction solution and the mixture was filtered under aspiration. Ion exchange water was further added, washing and filtration were repeated until the filtrate was neutralized (until the pH value did not virtually change). After filtration, the carbon nanotube was dried under vacuum at 80° C. for 12 hours to obtain a carbon nanotube.

Comparative Example 1-6 (Carbon Nanotube Oxidatively Treated in a Gaseous Phase)

Carbon nanotube A was placed in a heating furnace in an atmosphere (table-top electric furnace "AMF-20N," manufactured by Asahi Rika Seisakusho) and treated with heat at a temperature of 690° C. for 2 hours to obtain a carbon nanotube oxidatively treated in a gaseous phase. Note that the absolute value of $\Delta Id/Ig$ was 0.1. The compounds corresponding to those represented by formula (1) to formula (6) was not detected in the carbon nanotube.

Example 1-21 (Resin Composition Containing an Additive)

To the surface-treated carbon nanotube obtained in Example 1-3, carbodilite was blended as an additive in accordance with the conditions shown in the following table to prepare a resin composition. Subsequently, the physical properties of the resin composition were evaluated in the same manner as in Example 1-3.

Example 1-22 (Resin Composition Containing an Additive)

To the surface-treated carbon nanotube obtained in Example 1-3, a maleic anhydride was blended as an additive in accordance with the conditions shown in the following table to prepare a resin composition. Subsequently, the physical properties of the resin composition were evaluated in the same manner as in Example 1-3.

Reference Example 1-2

A resin composition was prepared in which the blending ratio of the resin composition and carbon nanotube A was shown in the following table. Subsequently, the physical properties of the resin composition were evaluated in the same manner as in Example 1-1.

Reference Example 1-3

The physical properties of the polyamide resin were evaluated in the same manner as in Example 1-1.

The physical properties and evaluation results of Examples and Comparative Examples are shown in Table 2 to Table 5. Note that the symbol "–" in the tables indicates that no measurement was made.

Figure 2:
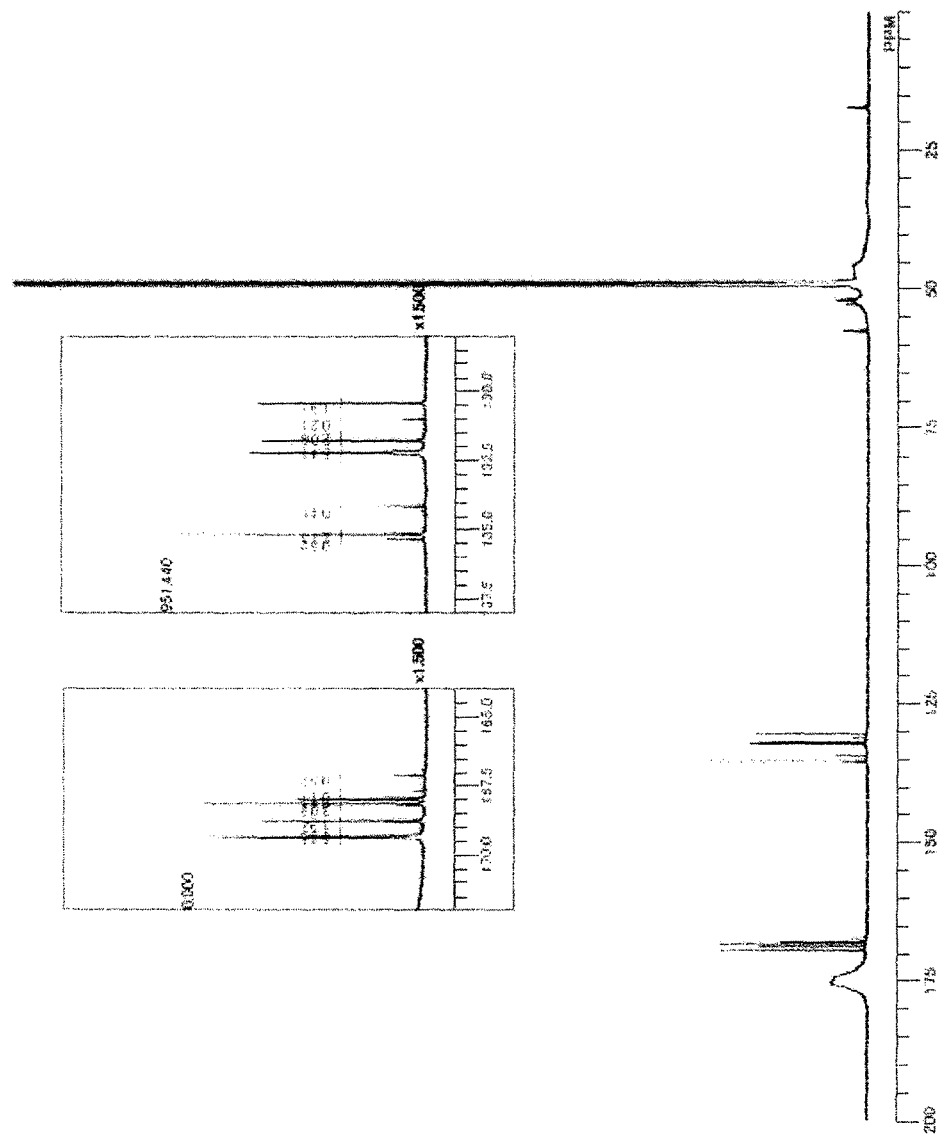
FIG. 2 is $^{13}$C-NMR spectrum of the filtrate (deposit) of the surface-treated carbon nanotube of Example 1-2 after washing.
Figure 3:
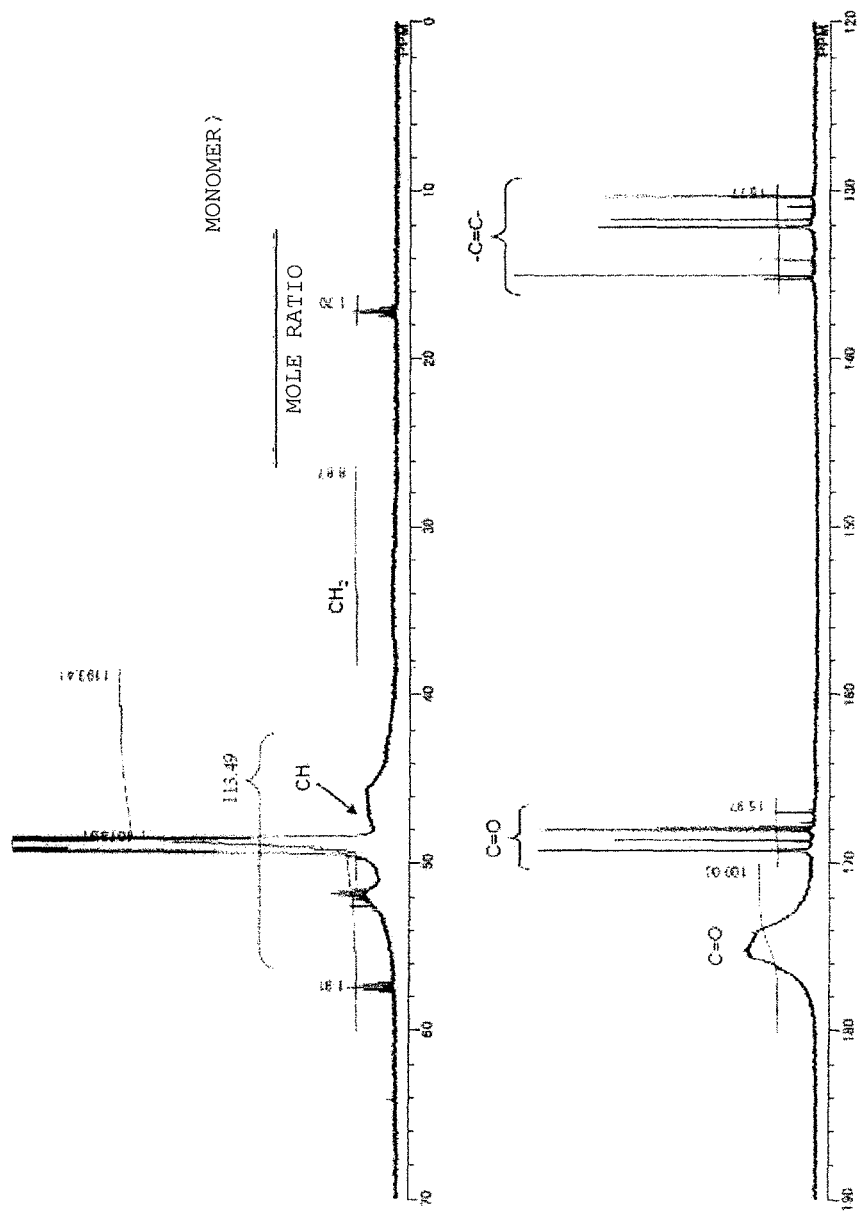
FIG. 3 is a partly enlarged view of FIG. 2.
Figure 4:
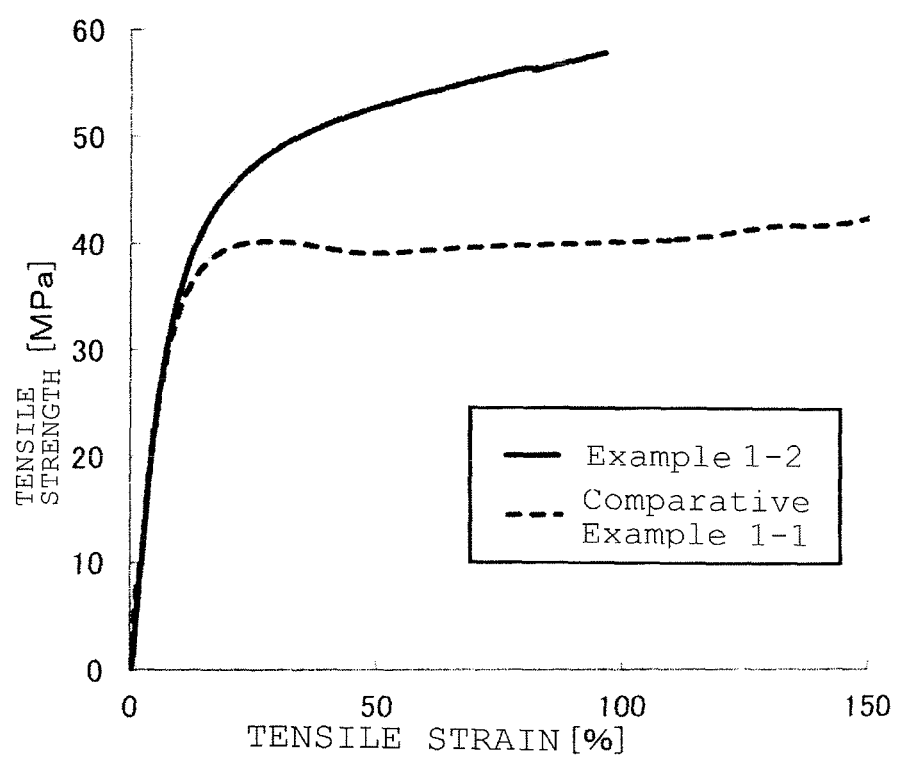
FIG. 4 is a graph showing tensile strength-tensile strain curves of the resin composition prepared in Example 1-2 and the resin composition prepared in Comparative Example 1-1.
Figure 5:
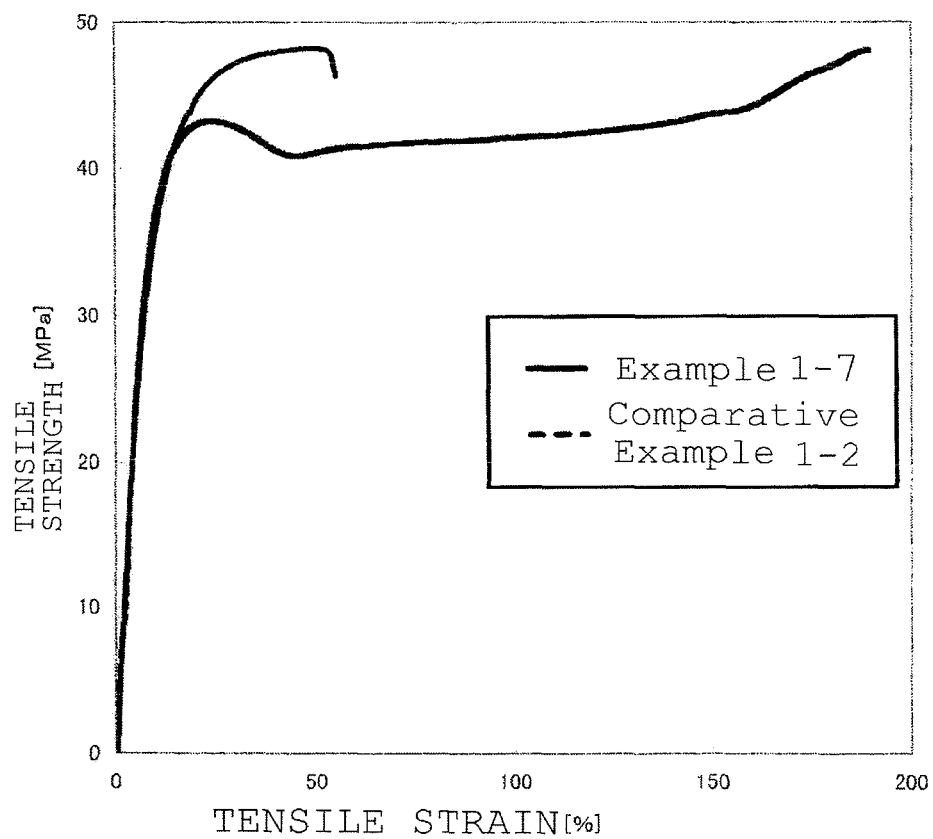
FIG. 5 is a graph obtained by plotting the tensile strain and tensile strength of the resin composition prepared in Example 1-7 and the resin composition prepared in Comparative Example 1-2.

Note that the chromatograph of the residue (bound substance) of the surface-treated carbon nanotube of Example 1-2 after washing obtained by pyrolysis-gas chromatography/mass spectroscopy (Py-GC/MS) is shown by way of example in FIG. 1. A $^{13}$C-NMR spectrum of the filtrate (deposit) of the surface-treated carbon nanotube of Example 1-2 after washing is shown in FIG. 2 and a partially enlarged view of FIG. 2 is shown in FIG. 3. Furthermore, a graph showing tensile strength-tensile strain curves of the resin composition prepared in Example 1-2 and the resin composition prepared in Comparative Example 1-1 is shown in FIG. 4; whereas, a graph obtained by plotting the tensile strain and the tensile strength of the resin composition prepared in Example 1-7 and the resin composition prepared in Comparative Example 1-2 is shown in FIG. 5.

TABLE 2

|  |  |  | Example 1-1 | Example 1-2 | Example 1-3 | Example 1-4 | Example 1-5 | Example 1-6 | Example 1-7 | Example 1-8 |
|---|---|---|---|---|---|---|---|---|---|---|
| CNT | Surface treatment reaction condition | Raw-material CNT | A | A | A | A | A | B | B | C |
|  |  | Treatment agent | Maleic anhydride | Maleic anhydride | Maleic anhydride | Maleic anhydride | Maleic anhydride | Maleic anhydride | Maleic anhydride | Maleic anhydride |
|  |  | Solvent | None | None | None | None | None | None | None | None |
|  |  | Reaction (° C.) | 180 | 180 | 180 | 180 | 200 | 180 | 180 | 180 |
|  |  | Time (hr) | 3 | 6 | 12 | 24 | 24 | 6 | 12 | 12 |
|  |  | Washing solvent | Toluene | Toluene | Toluene | Toluene | Toluene | Toluene | Toluene | Toluene |
|  | Surface element analysis XPS | Oxygen (%) | 9.6 | 18.0 | 22.7 | 28.6 | 30.4 | 18.9 | 21.6 | 22.1 |
|  |  | Sulfur (%) | Less than detection limit | Less than detection limit | Less than detection limit | Less than detection limit | Less than detection limit | Less than detection limit | Less than detection limit | Less than detection limit |
|  | Thermal reduction amount TGA | Weight loss (%) | 2.5 | 11.2 | 19.1 | 9.6 | 15.1 | 10.6 | 10.6 | 13.2 |
|  | Id/Ig Raman scattering spectroscopy | Id/Ig before reaction | 0.1 | 0.1 | 0.1 | 0.1 | 0.1 | 1.4 | 1.4 | 1.2 |
|  |  | Id/Ig after reaction | 0.2 | 0.1 | 0.1 | 0.1 | 0.1 | 2 | 1.9 | 1.6 |
|  |  | Absolute value of ΔId/Ig | 0.1 | 0 | 0 | 0 | 0.1 | 0.6 | 0.5 | 0.4 |
| Composition | Formulation | PA66 | 90 | 90 | 90 | 90 | 90 | 90 | 90 | 95 |
|  |  | Concentration of CNT (wt %) | 10 | 10 | 10 | 10 | 10 | 10 | 10 | 5 |
|  | Extrudability | Visual observation | ○ | ○ | ○ | ○ | ○ | ○ | ○ | ○ |
|  | Viscosity of PA composition solution | Viscosity of formic acid solution | 52 | 56 | 57 | 57 | 56 | — | — | — |
|  | Amount of remaining organic substance TGA | Organic substance (mass %) | 5.0 | 5.3 | 5.4 | 5.7 | 5.3 | 3.8 | 4.4 | 5 |
|  |  | Peak temperature of cooling crystallization temperature (° C.) | 239 | 239 | 231 | 232 | 229 | 232 | 230 | 230 |
|  | Physical properties at 120° C. | Tensile strength (MPa) | 53 | 56 | 55 | 58 | 52 | 44 | 48 | 51 |
|  |  | Specific strength (MPa) | 45 | 47 | 46 | 48 | 44 | 37 | 41 | 44 |
|  |  | Tensile elongation (%) | 105 | 91 | 47 | 96 | 77 | 50 | 55 | 68 |
|  | Creep property | Time (sec) until deformation reaches 15% by application of stress of 30 MPa | $4.1 \times 10^4$ | $5.0 \times 10^4$ | $5.3 \times 10^4$ | $6.6 \times 10^4$ | $4.5 \times 10^4$ | $3.0 \times 10^4$ | $3.4 \times 10^4$ | $3.4 \times 10^4$ |

TABLE 3

|  |  |  | Example 1-9 | Example 1-10 | Example 1-11 | Example 1-12 | Example 1-13 | Example 1-14 | Example 1-15 | Example 1-16 |
|---|---|---|---|---|---|---|---|---|---|---|
| CNT | Surface treatment reaction condition | Raw-material CNT | A | B | A | A | B | A | B | B |
|  |  | Treatment agent | Maleic anhydride | Maleic anhydride | Maleic anhydride | Maleic anhydride | Hydrogen peroxide | Citric acid | Citric acid | Surface activation |
|  |  | Solvent | None | Toluene | Toluene | Toluene | None | None | None |  |
|  |  | Reaction (° C.) | 180 | 180 | 180 | 180 | 90 | 200 | 200 |  |
|  |  | Time (hr) | 3 | 24 | 24 | 24 | 12 | 5 | 5 |  |
|  |  | Washing solvent | Methanol | Toluene | Toluene | Toluene | Ion exchange water | Warm water | Warm water |  |
|  | Surface element analysis XPS | Oxygen (%) | 1.9 | 4.8 | 3.4 | 3.4 | 3.5 | 7.5 | 13.3 | 0.9 |
|  |  | Sulfur (%) | Less than detection limit | Less than detection limit | Less than detection limit | Less than detection limit | Less than detection limit | Less than detection limit | Less than detection limit | Less than detection limit |
|  | Thermal reduction amount TGA | Weight loss (%) | 0.6 | 1.4 | 0.5 | 0.5 | 0.2 | 1.6 | 1.9 | 0.2 |
|  | Id/Ig Raman scattering spectroscopy | Id/Ig before reaction | 0.1 | 1.4 | 0.1 | 0.1 | 1.4 | 0.1 | 1.4 | 1.4 |
|  |  | Id/Ig after reaction | 0.1 | 1.4 | 0.1 | 0.1 | 1.2 | 0.1 | 1.2 | 1.1 |
|  |  | Absolute value of ΔId/Ig | 0 | 0 | 0 | 0 | 0.2 | 0 | 0.2 | 0.3 |
| Composition | Formulation | PA66 | 90 | 90 | 90 | 85 | 90 | 90 | 90 | 90 |
|  |  | Concentration of CNT (wt %) | 10 | 10 | 10 | 15 | 10 | 10 | 10 | 10 |
|  | Extrudability | Visual observation | ○ | ○ | ○ | ○ | ○ | ○ | ○ | ○ |
|  | Viscosity of PA composition solution | Viscosity of formic acid solution | 50 | 51 | 52 | 52 | 51 | 48 | 49 | — |
|  | Amount of remaining organic substance TGA | Organic substance (mass %) | 2.7 | 2.7 | 2.9 | 2.9 | 2.3 | 2.4 | 2.5 | 1.2 |

TABLE 3-continued

|  |  | Example 1-9 | Example 1-10 | Example 1-11 | Example 1-12 | Example 1-13 | Example 1-14 | Example 1-15 | Example 1-16 |
|---|---|---|---|---|---|---|---|---|---|
|  | Peak temperature of cooling crystallization temperature (° C.) |  |  |  | 240 |  |  |  | 241 |
| Physical properties at 120° C. | Tensile strength (MPa) | 44 | 45 | 44 | 47 | 47 | 44 | 44 | 43 |
|  | Specific strength (MPa) | 37 | 38 | 37 | 39 | 40 | 37 | 37 | 36 |
|  | Tensile elongation (%) | 130 | 143 | 133 | 141 | 112 | 163 | 148 | 154 |
| Creep property | Time (sec) until deformation reaches 15% by application of stress of 30 MPa | $1.3 \times 10^4$ | $1.0 \times 10^4$ | $1.2 \times 10^4$ | $1.2 \times 10^4$ | $2.0 \times 10^4$ | $1.2 \times 10^4$ | $1.1 \times 10^4$ | $4.9 \times 10^3$ |

TABLE 4

|  |  |  | Comparative Example 1-1 | Comparative Example 1-2 | Comparative Example 1-3 | Comparative Example 1-4 | Comparative Example 1-5 | Comparative Example 1-6 | Reference Example 1-1 | Reference Example 1-2 | Reference Example 1-3 |
|---|---|---|---|---|---|---|---|---|---|---|---|
| CNT | Surface treatment reaction condition | Raw-material CNT | A | A | A | A | A | A | A | A |  |
|  |  | Treatment agent | Sulfuric acid + nitric acid | Sulfuric acid + nitric acid | Sulfuric acid | Nitric acid | Hydrogen peroxide + sulfuric acid | Gas-phase oxidation | Not treated | Not treated |  |
|  |  | Solvent | — | — | — | — | — |  |  |  |  |
|  |  | Reaction (° C.) | 70 | 70 | 180 | 70 | 80 |  |  |  |  |
|  |  | Time (hr) | 24 | 24 | 24 | 24 | 24 |  |  |  |  |
|  |  | Washing solvent | Water | Ion exchange water | Ion exchange water | Ion exchange water | Ion exchange water |  |  |  |  |
|  | Surface element analysis XPS | Oxygen (%) | 14.2 | 13.3 | 0.7 | 0.3 | 3.5 | 0.3 | 0.2 | 0.2 |  |
|  |  | Sulfur (%) | 0.3 | 0.1 | 0.1 | Less than detection limit | 0.1 | Less than detection limit | Less than detection limit | Less than detection limit |  |
|  | Thermal reduction amount TGA | Weight loss (%) | 18.1 | 16.7 | 0.4 | 0.3 | 0.4 | 0.2 | 0.1 | 0.1 |  |
|  | Id/Ig Raman scattering spectroscopy | Id/Ig before reaction | 0.1 | 0.1 | 0.1 | 0.1 | 1.4 | 0.1 | 0.1 | 0.1 |  |
|  |  | Id/Ig after reaction | 1.7 | 1.4 | 0.1 | 0.1 | 1.1 | 0.2 |  |  |  |
|  |  | Absolute value of ΔId/Ig | 1.6 | 1.3 | 0 | 0 | 0.3 | 0.1 | — | — |  |
| Composition | Formulation | PA66 | 90 | 85 | 90 | 90 | 90 | 85 | 90 | 85 | 100 |
|  |  | Concentration of CNT (wt %) | 10 | 15 | 10 | 10 | 10 | 15 | 10 | 15 | 0 |
| Extrudability |  | Visual observation | x | x | x | x | x | ○ | ○ | ○ | ○ |
| Viscosity of PA composition solution |  | Viscosity of formic acid solution | 20 | 24 | 40 | 42 | 42 | — | 51 | 51 | 48 |
| Amount of remaining organic substance TGA |  | Organic substance (mass %) | 1.3 | 1.4 | 0.2 | 0.2 | 1.4 | 0.8 | 0.2 | 0.3 | 0 |
|  |  | Peak temperature of cooling crystallization temperature (° C.) |  |  | 241 | 241 |  | 241 | 241 | 241 | 221 |
| Physical properties at 120° C. |  | Tensile strength (MPa) | 35 | 35 | 38 | 39 | 40 | 41 | 40 | 41 | 35 |
|  |  | Specific strength (MPa) | 29 | 29 | 32 | 33 | 34 | 34 | 33 | 33 | 31 |
|  |  | Tensile elongation (%) | 13 | 10 | 223 | 225 | 72 | 188 | 201 | 173 | 371 |
| Creep property |  | Time (sec) until deformation reaches 15% by application of stress of 30 MPa | $1.5 \times 10^3$ | $1.6 \times 10^3$ | $1.6 \times 10^3$ | $1.7 \times 10^3$ | $2.5 \times 10^3$ | $3.8 \times 10^3$ | $1.8 \times 10^3$ | $1.7 \times 10^3$ | — |

TABLE 5

|  |  |  | Example 1-17 | Example 1-18 | Example 1-19 | Example 1-20 | Example 1-21 | Example 1-22 |
|---|---|---|---|---|---|---|---|---|
| CNT | Surface treatment reaction condition | Raw-material CNT | A | A | A | A | A | A |
|  |  | Treatment agent | Maleic anhydride | Ethylene-maleic anhydride copolymer | Poly (acrylic acid) | Poly (acrylic acid)-maleic acid | Maleic anhydride | Maleic anhydride |
|  |  | Solvent | None | 1-Methyl-2-pyrrolidone | 1-Methyl-2-pyrrolidone | 1-Methyl-2-pyrrolidone | None | None |
|  |  | Initiator | AIBN | None | None | None | None | None |
|  |  | Reaction (° C.) | 120 | 180 | 180 | 180 | 180 | 180 |
|  |  | Time (hr) | 6 | 6 | 6 | 6 | 12 | 12 |
|  |  | Washing solvent | Toluene | Acetone | Acetone | Acetone | Toluene | Toluene |
|  | Surface element analysis XPS | Oxygen (%) | 12.3 | 7.3 | 5.1 | 5.9 | 22.7 | 22.7 |
|  |  | Sulfur (%) | Less than detection limit | Less than detection limit | Less than detection limit | Less than detection limit | Less than detection limit | Less than detection limit |
|  | Thermal reduction amount TGA | Weight loss (%) | 18.6 | 3.7 | 0.9 | 3.7 | 19.1 | 19.1 |
|  | Id/Ig Raman scattering spectroscopy | Id/Ig before reaction | 0.1 | 0.1 | 0.1 | 0.1 | 0.1 | 0.1 |
|  |  | Id/Ig after reaction | 0.2 | 0.1 | 0.1 | 0.1 | 0.1 | 0.1 |
|  |  | Absolute value of ΔId/Ig | 0.1 | 0 | 0 | 0 | 0 | 0 |
| Composition | Formulation | PA66 | 90 | 90 | 90 | 90 | 89 | 87 |
|  |  | Concentration of CNT (wt %) | 10 | 10 | 10 | 10 | 10 | 10 |
|  |  | Other additives | None | None | None | None | Cabodilite | Maleic anhydride |
|  |  | Concentration of others (%) | 0 | 0 | 0 | 0 | 1 | 3 |
|  | Extrudability | Visual observation | ○ | ○ | ○ | ○ | ○ | ○ |
|  | Viscosity of PA composition solution | Viscosity of formic acid solution | — | 53 | 55 | 55 | — | — |
|  | Amount of remaining organic substance TGA | Organic substance (mass %) | — | — | — | — | — | — |
|  | Physical properties at 120° C. | Tensile strength (MPa) | 44 | 44 | 46 | 44 | 56 | 47 |
|  |  | Specific strength (MPa) | 37 | 37 | 39 | 37 | 47 | 39 |
|  |  | Tensile elongation (%) | 92 | 137 | 120 | 113 | 119 | 35 |
|  | Creep property | Time (sec) until deformation reaches 15% by application of stress of 30 MPa | — | — | — | — | $1.0 \times 10^4$ | — |

As shown in the tables, it was confirmed at least that, in Examples, the surface damage of carbon nanotubes is low before and after the surface treatment. Furthermore, it was confirmed that since the value of formic acid melt viscosity is high, and the molecular weight of a resin does not decrease when carbon nanotubes are mixed with resins. Moreover, it was confirmed that extrudability is also excellent. In contrast, in Comparative Examples, it was confirmed that at least one of absolute value of ΔId/Ig, formic acid melt viscosity and extrudability is inferior.

The surface states of surface-treated carbon nanotubes of Examples 1-1 to 1-15 and 1-17 to 1-20 were further analyzed. The presence or absence of a bound substance and a deposit was confirmed in accordance with the aforementioned methods and the bound substance and the deposit were quantified. The results are shown in Table 6 to Table 8.

TABLE 6

|  |  |  | Example 1-1 | Example 1-2 | Example 1-3 | Example 1-4 | Example 1-5 | Example 1-6 | Example 1-7 |
|---|---|---|---|---|---|---|---|---|---|
| CNT | Surface treatment reaction condition | Raw-material CNT | A | A | A | A | A | B | B |
|  |  | Treatment agent | Maleic anhydride | Maleic anhydride | Maleic anhydride | Maleic anhydride | Maleic anhydride | Maleic anhydride | Maleic anhydride |
|  |  | Solvent | None | None | None | None | None | None | None |
|  |  | Reaction (° C.) | 180 | 180 | 180 | 180 | 200 | 180 | 180 |
|  |  | Time (hr) | 3 | 6 | 12 | 24 | 24 | 6 | 12 |
|  |  | Washing solvent | Toluene | Toluene | Toluene | Toluene | Toluene | Toluene | Toluene |
|  | Bound substance (surface treatment) Py-GC/MS | Detection of components (1) to (4) | Detected | Detected | Detected | Detected | Detected | Detected | Detected |

TABLE 6-continued

|  |  | Example 1-1 | Example 1-2 | Example 1-3 | Example 1-4 | Example 1-5 | Example 1-6 | Example 1-7 |
|---|---|---|---|---|---|---|---|---|
| Deposit (surface treatment) 13C-NMR, GPC | Detection of components (5) and (6) | 6300/900 | 6500/900 | 7000/900 | 7200/900 | 7500/900 | 6800/900 | 7000/900 |

TABLE 7

| | | | Example 1-8 | Example 1-9 | Example 1-10 | Example 1-11 | Example 1-12 | Example 1-13 | Example 1-14 | Example 1-15 |
|---|---|---|---|---|---|---|---|---|---|---|
| CNT | Surface treatment reaction condition | Raw-material CNT | C | A | B | A | A | B | A | B |
| | | Treatment agent | Maleic anhydride | Maleic anhydride | Maleic anhydride | Maleic anhydride | Maleic anhydride | Hydrogen peroxide | Citric acid | Citric acid |
| | | Solvent | None | None | Toluene | Toluene | Toluene | None | None | None |
| | | Reaction (° C.) | 180 | 180 | 180 | 180 | 180 | 90 | 200 | 200 |
| | | Time (hr) | 12 | 3 | 24 | 24 | 24 | 12 | 5 | 5 |
| | | Washing solvent | Toluene | Methanol | Toluene | Toluene | Toluene | Ion exchamge water | Warm water | Warm water |
| | Bound substance (surface treatment) Py-GC/MS | Detection of components (1) to (4) | Detected | Detected | Detected | Detected | Detected | Not detected | Not detected | Not detected |
| | Deposit (surface treatment) 13C-NMR, GPC | Detection of components (5) and (6) | 7200/900 | Not detected | Not detected | Not detected | Not detected | Not detected | Not detected | Not detected |

TABLE 8

| | | | Example 1-17 | Example 1-18 | Example 1-19 | Example 1-20 |
|---|---|---|---|---|---|---|
| CNT | Surface treatment reaction condition | Raw-material CNT | A | A | A | A |
| | | Treatment agent | Maleic anhydride | Ethylene-maleic anhydride copolymer | Poly(acrylic acid) | Poly(acrylic acid)-maleic acid |
| | | Solvent | None | 1-Methyl-2-pyrrolidone | 1-Methyl-2-pyrrolidone | 1-Methyl-2-pyrrolidone |
| | | Initiator | AIBN | None | None | None |
| | | Reaction (° C.) | 120 | 180 | 180 | 180 |
| | | Time (hr) | 6 | 6 | 6 | 6 |
| | | Washing solvent | Toluene | Acetone | Acetone | Acetone |
| | Bound substance (surface treatment) Py-GC/MS | Detection of (1) to (4) in interface | Detected | — | — | — |
| | Deposit (surface treatment) 13C-NMR, GPC | Detection of (5) and (6) in interface | 1000 | — | — | — |

With respect to carbon nanotubes of Comparative Examples and Experimental Examples shown below, the surface elements of the surface-treated carbon nanotubes having a deposit of an organic substance after HFIP elution were analyzed. The results are shown in Table 9.

TABLE 9

| | | | Reference Example 1-1 | Example 1-9 | Comparative Example 1-2 | Example 1-3 |
|---|---|---|---|---|---|---|
| Composition | Surface element analysis of residue after HFIP elution XPS | Carbon | 98.2 | 93.4 | 97.1 | 86.7 |
| | | Oxygen | 1.4 | 3.4 | 2.2 | 6.8 |
| | | Nitrogen | 0.4 | 3.2 | 0.6 | 6.5 |
| | | Sulfur | Less than detection limit | Less than detection limit | 0.1 | Less than detection limit |

Experiment 2

(Measurement Method)

Unless otherwise specified, individual measurements were performed in accordance with the methods described in <Experiment 1>.

(Raw Material)

Unless otherwise specified, the raw material described in <Experiment 1> was used. Note that a resin composition was prepared in accordance with the method described in <Experiment 1>, unless otherwise specified.

Example 2-1 (Carbon Nanotube Whose Surface was Treated with a Maleic Anhydride)

The carbon nanotube obtained in Example 1-1 was used.

Example 2-2 (Carbon Nanotube Whose Surface was Treated with a Maleic Anhydride)

The carbon nanotube obtained in Example 1-2 was used.

Example 2-3 (Carbon Nanotube Whose Surface was Treated with a Maleic Anhydride)

The carbon nanotube obtained in Example 1-3 was used.

Example 2-4 (Carbon Nanotube Whose Surface was Treated with a Maleic Anhydride)

The carbon nanotube obtained in Example 1-4 was used.

Example 2-5 (Carbon Nanotube Whose Surface was Treated with a Maleic Anhydride)

The carbon nanotube obtained in Example 1-5 was used.

Example 2-6 (Carbon Nanotube Whose Surface was Treated with a Maleic Anhydride)

The carbon nanotube obtained in Example 1-6 was used.

Example 2-7 (Carbon Nanotube Whose Surface was Treated with a Maleic Anhydride)

The carbon nanotube obtained in Example 1-7 was used.

Example 2-8 (Carbon Nanotube Whose Surface was Treated with a Maleic Anhydride)

The carbon nanotube obtained in Example 1-8 was used.

Example 2-9 (Carbon Nanotube Whose Surface was Treated with a Maleic Anhydride)

The carbon nanotube obtained in Example 1-9 was used.

Example 2-10 (Carbon Nanotube Whose Surface was Treated with a Maleic Anhydride)

The carbon nanotube obtained in Example 1-10 was used.

Example 2-11 (Carbon Nanotube Whose Surface was Treated with a Maleic Anhydride)

The carbon nanotube obtained in Example 1-11 was used.

Example 2-12 (Carbon Nanotube Whose Surface was Treated with a Maleic Anhydride)

The carbon nanotube obtained in Example 1-12 was used.

Example 2-13 (Surface-Activated Carbon Nanotube)

The carbon nanotube obtained in Example 1-16 was used.

Example 2-14 (Carbon Nanotube Whose Surface was Treated with an Ethylene-Maleic Anhydride Copolymer)

The carbon nanotube obtained in Example 1-17 was used.

Example 2-15 (Carbon Nanotube Whose Surface was Treated with a Poly(Acrylic Acid))

The carbon nanotube obtained in Example 1-18 was used.

Example 2-16 (Carbon Nanotube Whose Surface was Treated with Poly(Acrylic Acid-Co-Maleic Acid))

The carbon nanotube obtained in Example 1-19 was used.

Reference Example 2-1 (Carbon Nanotube Whose Surface was not Treated)

A raw-material carbon nanotube A was used as it was.

Reference Example 2-2 (Carbon Nanotube Whose Surface was Treated with Hydrogen Peroxide Solution)

The carbon nanotube obtained in Example 1-13 was used.

Reference Example 2-3 (Carbon Nanotube Whose Surface was Treated with Citric Acid)

The carbon nanotube obtained in Example 1-14 was used.

Reference Example 2-4 (Carbon Nanotube Whose Surface was Treated with Citric Acid)

The carbon nanotube obtained in Example 1-15 was used.

Comparative Example 2-1 (Carbon Nanotube Whose Surface was Treated with a Mixed Acid of Sulfuric Acid and Nitric Acid)

The carbon nanotube obtained in Comparative Example 1-1 was used.

Comparative Example 2-2 (Carbon Nanotube Whose Surface was Treated with a Mixed Acid of Sulfuric Acid and Nitric Acid)

The carbon nanotube obtained in Comparative Example 1-2 was used.

Comparative Example 2-3 (Carbon Nanotube Whose Surface was Treated with Sulfuric Acid)

The carbon nanotube obtained in Comparative Example 1-3 was used.

Comparative Example 2-4 (Carbon Nanotube Whose Surface was Treated with Nitric Acid)

The carbon nanotube obtained in Comparative Example 1-4 was used.

Comparative Example 2-5 (Carbon Nanotube e Whose Surface was Treated with Hydrogen Peroxide and Sulfuric Acid)

The carbon nanotube obtained in Comparative Example 1-5 was used.

Comparative Example 2-6 (Carbon Nanotube Oxidatively Treated in a Gaseous Phase)

The carbon nanotube obtained in Reference Example 1-6 was used.

Example 2-17 (Resin Composition Containing an Additive)

To the surface-treated carbon nanotube obtained in Example 2-3, carbodilite was blended as an additive in the conditions shown in the following table to prepare a resin composition. Subsequently, the physical properties of the resin composition were evaluated in the same manner as in Example 2-3.

Example 2-18 (Resin Composition Containing an Additive)

To the surface-treated carbon nanotube obtained in Example 2-3, a maleic anhydride was blended as an additive in the conditions shown in the following table to prepare a resin composition. Subsequently, the physical properties of the resin composition were evaluated in the same manner as in Example 2-3.

Reference Example 2-5

A resin composition was prepared in which the blending ratio of the resin composition and carbon nanotube A was shown in the following table. Subsequently, the physical properties of the resin composition were evaluated in the same manner as in Example 2-1.

Reference Example 2-6

The physical properties of the polyamide resin were evaluated in the same manner as in Example 1.

The physical properties and evaluation results of Examples and Comparative Examples are shown in Table 10 to Table 13.

TABLE 10

| | | | Example 2-1 | Example 2-2 | Example 2-3 | Example 2-4 | Example 2-5 | Example 2-6 | Example 2-7 |
|---|---|---|---|---|---|---|---|---|---|
| CNT | Surface treatment reaction condition | Raw-material CNT | A | A | A | A | A | B | B |
| | | Treatment agent | Maleic anhydride | Maleic anhydride | Maleic anhydride | Maleic anhydride | Maleic anhydride | Maleic anhydride | Maleic anhydride |
| | | Solvent | None | None | None | None | None | None | None |
| | | Reaction (°C.) | 180 | 180 | 180 | 180 | 200 | 180 | 180 |
| | | Time (hr) | 3 | 6 | 12 | 24 | 24 | 6 | 12 |
| | | Washing solvent | Toluene | Toluene | Toluene | Toluene | Toluene | Toluene | Toluene |
| | Surface element analysis XPS | Oxygen (%) | 9.6 | 18.0 | 22.7 | 28.6 | 30.4 | 18.9 | 21.6 |
| | | Sulfur (%) | Less than detection limit | Less than detection limit | Less than detection limit | Less than detection limit | Less than detection limit | Less than detection limit | Less than detection limit |
| | Thermal reduction amount TGA | Weight loss (%) | 2.5 | 11.2 | 19.1 | 9.6 | 15.1 | 10.6 | 10.6 |
| | Id/Ig Raman scattering spectroscopy | Id/Ig before reaction | 0.1 | 0.1 | 0.1 | 0.1 | 0.1 | 1.4 | 1.4 |
| | | Id/Ig after reaction | 0.2 | 0.1 | 0.1 | 0.1 | 0.1 | 2 | 1.9 |
| | | Absolute value of ΔId/Ig | 0.1 | 0 | 0 | 0 | 0.1 | 0.6 | 0.5 |
| | Bound substance (surface treatment) Py-GC/MS | Detection of components (1) to (4) | Detected | Detected | Detected | Detected | Detected | Detected | Detected |
| | Deposit (surface treatment) 13C-NMR, GPC | Detection of components (5) and (6) | 6300/900 | 6500/900 | 7000/900 | 7200/900 | 7500/900 | 6800/900 | 7000/900 |
| Composition | Formulation | PA66 | 90 | 90 | 90 | 90 | 90 | 90 | 90 |
| | | Concentration of CNT (wt %) | 10 | 10 | 10 | 10 | 10 | 10 | 10 |
| | Extrudability | Visual observation | ○ | ○ | ○ | ○ | ○ | ○ | ○ |
| | Viscosity of PA composition solution | Viscosity of formic acid solution | 52 | 56 | 57 | 57 | 56 | — | — |
| | Amount of remaining organic substance TGA | Organic substance (mass %) | 5.0 | 5.3 | 5.4 | 5.7 | 5.3 | 3.8 | 4.4 |
| | | Peak temperature of cooling crystallization temperature (°C.) | 239 | 239 | 231 | 232 | 229 | 232 | 230 |
| | Physical properties at 120° C. | Tensile strength (MPa) | 53 | 56 | 55 | 58 | 52 | 44 | 48 |
| | | Specific strength (MPa) | 45 | 47 | 46 | 48 | 44 | 37 | 41 |
| | | Tensile elongation (%) | 105 | 91 | 47 | 96 | 77 | 50 | 55 |
| | Creep property | Time (sec) until deformation reaches 15% by application of stress of 30 MPa | $4.1 \times 10^4$ | $5.0 \times 10^4$ | $5.3 \times 10^4$ | $6.6 \times 10^{40}$ | $4.5 \times 10^4$ | $3.0 \times 10^4$ | $3.1 \times 10^4$ |

TABLE 11

| | | | Example 2-8 | Example 2-9 | Example 2-10 | Example 2-11 | Example 2-12 | Example 2-13 |
|---|---|---|---|---|---|---|---|---|
| CNT | Surface treatment reaction condition | Raw-material CNT | C | A | B | A | A | B |
| | | Treatment agent | Maleic anhydride | Maleic anhydride | Maleic anhydride | Maleic anhydride | Maleic anhydride | Surface activation |
| | | Solvent | None | None | Toluene | Toluene | Toluene | |
| | | Reaction (° C.) | 180 | 180 | 180 | 180 | 180 | |
| | | Time (hr) | 12 | 3 | 24 | 24 | 24 | |
| | | Washing solvent | Toluene | Methanol | Toluene | Toluene | Toluene | |
| | Surface element analysis XPS | Oxygen (%) | 22.1 | 1.9 | 4.8 | 3.4 | 3.4 | 0.9 |
| | | Sulfur (%) | Less than detection limit | Less than detection limit | Less than detection limit | Less than detection limit | Less than detection limit | Less than detection limit |
| | Thermal reduction amount TGA | Weight loss (%) | 13.2 | 0.6 | 1.4 | 0.5 | 0.5 | 0.2 |
| | Id/Ig Raman scattering spectroscopy | Id/Ig before reaction | 1.2 | 0.1 | 1.4 | 0.1 | 0.1 | 1.4 |
| | | Id/Ig after reaction | 1.6 | 0.1 | 1.4 | 0.1 | 0.1 | 1.1 |
| | | Absolute value of ΔId/Ig | 0.4 | 0 | 0 | 0 | 0 | 0.3 |
| | Bound substance (surface treatment) Py-GC/MS | Detection of components (1) to (4) | Detected | Detected | Detected | Detected | Detected | Detected |
| | Deposit (surface treatment) 13C-NMR, GPC | Detection of components (5) and (6) | 7200/900 | Not detected | Not detected | Not detected | Not detected | Not detected |
| Composition | Formulation | PA66 | 95 | 90 | 90 | 90 | 85 | 90 |
| | | Concentration of CNT (wt %) | 5 | 10 | 10 | 10 | 15 | 10 |
| | Extrudability | Visual observation | ○ | ○ | ○ | ○ | ○ | ○ |
| | Viscosity of PA composition solution | Viscosity of formic acid solution | — | 50 | 51 | 52 | 52 | — |
| | Amount of remaining organic substance TGA | Organic substance (mass %) | 5 | 2.7 | 2.7 | 2.9 | 2.9 | 1.2 |
| | Peak temperature of cooling crystallization temperature (° C.) | | 230 | | | | 240 | 241 |
| | Physical properties at 120° C. | Tensile strength (MPa) | 51 | 44 | 45 | 44 | 47 | 43 |
| | | Specific strength (MPa) | 44 | 37 | 38 | 37 | 39 | 36 |
| | | Tensile elongation (%) | 68 | 130 | 143 | 133 | 141 | 154 |
| | Creep property | Time (sec) until deformation reaches 15% by application of stress of 30 MPa | $3.4 \times 10^4$ | $1.3 \times 10^4$ | $1.0 \times 10^4$ | $1.2 \times 10^4$ | $1.2 \times 10^4$ | $4.9 \times 10^4$ |

TABLE 12

| | | | Reference Example 2-1 | Reference Example 2-2 | Reference Example 2-3 | Reference Example 2-4 | Reference Example 2-5 | Reference Example 2-6 |
|---|---|---|---|---|---|---|---|---|
| CNT | Surface treatment reaction condition | Raw-material CNT | A | B | A | B | A | |
| | | Treatment agent | Not treated | Hydrogen peroxide | Citric acid | Citric acid | Not treated | |
| | | Solvent | | None | None | None | | |
| | | Reaction (° C.) | | 90 | 200 | 200 | | |
| | | Time (hr) | | 12 | 5 | 5 | | |
| | | Washing solvent | | Ion exchange water | Warm water | Warm water | | |
| | Surface element analysis XPS | Oxygen (%) | 0.2 | 3.5 | 7.5 | 13.3 | 0.2 | |
| | | Sulfur (%) | Less than detection limit | Less than detection limit | Less than detection limit | Less than detection limit | Less than detection limit | |
| | Thermal reduction amount TGA | Weight loss (%) | 0.1 | 0.2 | 1.6 | 1.9 | 0.1 | |
| | Id/Ig Raman scattering spectroscopy | Id/Ig before reaction | 0.1 | 1.4 | 0.1 | 1.4 | 0.1 | |
| | | Id/Ig after reaction | | 1.2 | 0.1 | 1.2 | | |
| | | Absolute value of ΔId/Ig | — | 0.2 | 0 | 0.2 | — | |
| | Bound substance (surface treatment) Py-GC/MS | Detection of components (1) to (4) | Not detected | Not detected | Not detected | Not detected | Not detected | |
| | Deposit (surface treatment) 13C-NMR, GPC | Detection of components (5) and (6) | Not detected | Not detected | Not detected | Not detected | Not detected | |

TABLE 12-continued

|  |  |  | Reference Example 2-1 | Reference Example 2-2 | Reference Example 2-3 | Reference Example 2-4 | Reference Example 2-5 | Reference Example 2-6 |
| --- | --- | --- | --- | --- | --- | --- | --- | --- |
| Composition | Formulation | PA66 | 90 | 90 | 90 | 90 | 85 | 100 |
|  |  | Concentration of CNT (wt %) | 10 | 10 | 10 | 10 | 15 | 0 |
|  | Extrudability | Visual observation | ○ | ○ | ○ | ○ | ○ | ○ |
|  | Viscosity of PA composition solution | Viscosity of formic acid solution | 51 | 51 | 48 | 49 | 51 | 48 |
|  | Amount of remaining organic substance TGA | Organic substance (mass %) | 0.2 | 2.3 | 2.4 | 2.5 | 0.3 | 0 |
|  | Peak temperature of cooling crystallization temperature (° C.) |  | 241 |  |  |  | 241 | 221 |
|  | Physical properties at 120° C. | Tensile strength (MPa) | 40 | 47 | 44 | 44 | 41 | 35 |
|  |  | Specific strength (MPa) | 33 | 40 | 37 | 37 | 33 | 31 |
|  |  | Tensile elongation (%) | 201 | 112 | 163 | 148 | 173 | 371 |
|  | Creep property | Time (sec) until deformation reaches 15% by application of stress of 30 MPa | $1.8 \times 10^3$ | $2.0 \times 10^4$ | $1.2 \times 10^4$ | $1.1 \times 10^4$ | $1.7 \times 10^3$ | — |

TABLE 13

|  |  |  | Comparative Example 2-1 | Comparative Example 2-2 | Comparative Example 2-3 | Comparative Example 2-4 | Comparative Example 2-5 | Comparative Example 2-6 |
| --- | --- | --- | --- | --- | --- | --- | --- | --- |
| CNT | Surface treatment reaction condition | Raw-material CNT | A | A | A | A | A | A |
|  |  | Treatment agent | Sulfuric acid + nitric acid | Sulfuric acid + nitric acid | Sulfuric acid | Nitric acid | Hydrogen peroxide + sulfuric acid | Gas-phase oxidation |
|  |  | Solvent | — | — | — | — | — |  |
|  |  | Reaction (° C.) | 70 | 70 | 180 | 70 | 80 |  |
|  |  | Time (hr) | 24 | 24 | 24 | 24 | 24 |  |
|  |  | Washing solvent | Water | Ion exchange water | Ion exchange water | Ion exchange water | Ion exchange water |  |
|  | Surface element analysis XPS | Oxygen (%) | 14.2 | 13.3 | 0.7 | 0.3 | 3.5 | 0.3 |
|  |  | Sulfur (%) | 0.3 | 0.1 | 0.1 | Less than detection limit | 0.1 | Less than detection limit |
|  | Thermal reduction amount TGA | Weight loss (%) | 18.1 | 16.7 | 0.4 | 0.3 | 0.4 | 0.2 |
|  | Id/Ig Raman scattering spectroscopy | Id/Ig before reaction | 0.1 | 0.1 | 0.1 | 0.1 | 1.4 | 0.1 |
|  |  | Id/Ig after reaction | 1.7 | 1.4 | 0.1 | 0.1 | 1.1 | 0.2 |
|  |  | Absolute value of ΔId/Ig | 1.6 | 1.3 | 0 | 0 | 0.3 | 0.1 |
|  | Bound substance (surface treatment) Py-GC/MS | Detection of components (1) to (4) | Not detected | Not detected | Not detected | Not detected | Not detected | Not detected |
|  | Deposit (surface treatment) 13C-NMR, GPC | Detection of components (5) and (6) | Not detected | Not detected | Not detected | Not detected | Not detected | Not detected |
| Composition | Formulation | PA66 | 90 | 85 | 90 | 90 | 90 | 85 |
|  |  | Concentration of CNT (wt %) | 10 | 15 | 10 | 10 | 10 | 15 |
|  | Extrudability | Visual observation | x | x | x | x | x | ○ |
|  | Viscosity of PA composition solution | Viscosity of formic acid solution | 20 | 24 | 40 | 42 | 42 | — |
|  | Amount of remaining organic substance TGA | Organic substance (mass %) | 1.3 | 1.4 | 0.2 | 0.2 | 1.4 | 0.8 |
|  | Peak temperature of cooling crystallization temperature (° C.) |  |  |  | 241 | 241 |  | 241 |
|  | Physical properties at 120° C. | Tensile strength (MPa) | 35 | 35 | 38 | 39 | 40 | 41 |
|  |  | Specific strength (MPa) | 29 | 29 | 32 | 33 | 34 | 34 |
|  |  | Tensile elongation (%) | 13 | 10 | 223 | 225 | 72 | 188 |
|  | Creep property | Time (sec) until deformation reaches 15% by application of stress of 30 MPa | $1.5 \times 10^3$ | $1.6 \times 10^3$ | $1.6 \times 10^3$ | $1.7 \times 10^3$ | $2.5 \times 10^3$ | $3.8 \times 10^3$ |

As is apparent from the tables, it was confirmed that resin compositions of the surface-treated carbon nanotubes of Examples are excellent in tensile strength, specific strength and tensile elongation.

Note that with respect to carbon nanotubes of Reference Example 2-1, Example 2-9, Comparative Example 2-2 and Reference Example 2-2, the surface elements of the surface-treated carbon nanotubes a having deposit of an organic substance deposit after HFIP elution were analyzed. The results are shown in Table 14.

TABLE 14

|  |  |  | Reference Example 2-1 | Example 2-9 | Comparative Example 2-2 | Reference Example 2-2 |
|---|---|---|---|---|---|---|
| Composition | Surface element analysis of residue after HFIP elution XPS | Carbon | 98.2 | 93.4 | 97.1 | 86.7 |
|  |  | Oxygen | 1.4 | 3.4 | 2.2 | 6.8 |
|  |  | Nitrogen | 0.4 | 3.2 | 0.6 | 6.5 |
|  |  | Sulfur | Less than detection limit | Less than detection limit | 0.1 | Less than detection limit |

Experiment 3

(Measurement Method)

Unless otherwise specified, individual measurements were performed in accordance with the methods described in <Experiment 1>. Note that resin compositions were prepared in accordance with the method described in <Experiment 1>, unless otherwise specified.

(Raw Material)

Unless otherwise specified, the raw material described in <Experiment 1> was used.

Example 3-1 (Resin Composition)

A polyamide resin was prepared using the carbon nanotube obtained in Example 1-1 in the conditions shown in the following table. Polyamide 66 (trade name: "Leona 1300S," manufactured by Asahi Kasei Chemicals Corporation) and the carbon nanotube were supplied in accordance with the formulation shown in the following table to a kneader ("XPlore" (a kneader equipped with a small kneader and a molding machine) manufactured by Royal DSM), and kneaded at a screw rotation number of 100 rpm and a kneading temperature of 300° C. for 2 minutes, and injected at a mold temperature of 80° C. and an injection pressure of 11 bar (30 seconds) to prepare dumbbell test pieces of ISO36 Type3 (size of equilibrium portion of a dumbbell: length 16 mm×width 4 mm×thickness 2 mm).

Example 3-2 (Resin Composition)

Dumbbell test pieces were prepared in the same manner as in Example 3-1 except that the carbon nanotube obtained in Example 1-2 was used and the component composition described in the following table was used.

Example 3-3 (Resin Composition)

Dumbbell test pieces were prepared in the same manner as in Example 3-1 except that the carbon nanotube obtained in Example 1-3 was used and the component composition described in the following table was used.

Example 3-4 (Resin Composition)

Dumbbell test pieces were prepared in the same manner as in Example 3-1 except that the carbon nanotube obtained in Example 1-4 was used and the component composition described in the following table was used.

Example 3-5 (Resin Composition)

Dumbbell test pieces were prepared in the same manner as in Example 3-1 except that the carbon nanotube obtained in Example 1-5 was used and the component composition described in the following table was used.

Example 3-6 (Resin Composition)

Dumbbell test pieces were prepared in the same manner as in Example 3-1 except that the carbon nanotube obtained in Example 1-6 was used and the component composition described in the following table was used.

Example 3-7 (Resin Composition)

Dumbbell test pieces were prepared in the same manner as in Example 3-1 except that the carbon nanotube obtained in Example 1-7 was used and the component composition described in the following table was used.

Example 3-8 (Resin Composition)

Dumbbell test pieces were prepared in the same manner as in Example 3-1 except that the carbon nanotube obtained in Example 1-8 was used and the component composition described in the following table was used.

Example 3-9 (Resin Composition)

Dumbbell test pieces were prepared in the same manner as in Example 3-1 except that the carbon nanotube obtained in Example 1-9 was used and the component composition described in the following table was used.

Example 3-10 (Resin Composition)

Dumbbell test pieces were prepared in the same manner as in Example 3-1 except that the carbon nanotube obtained in Example 1-10 was used and the component composition described in the following table was used.

Example 3-11 (Resin Composition)

Dumbbell test pieces were prepared in the same manner as in Example 3-1 except that the carbon nanotube obtained in Example 1-11 was used and the component composition described in the following table was used.

Example 3-12 (Resin Composition)

Dumbbell test pieces were prepared in the same manner as in Example 3-1 except that the carbon nanotube obtained in Example 1-12 was used and the component composition described in the following table was used.

Example 3-13 (Resin Composition)

Dumbbell test pieces were prepared in the same manner as in Example 3-1 except that the carbon nanotube obtained in Example 1-13 was used and the component composition described in the following table was used.

Example 3-14 (Resin Composition)

Dumbbell test pieces were prepared in the same manner as in Example 3-1 except that the carbon nanotube obtained in Example 1-14 was used and the component composition described in the following table was used.

Example 3-15 (Resin Composition)

Dumbbell test pieces were prepared in the same manner as in Example 3-1 except that the carbon nanotube obtained in Example 1-15 was used and the component composition described in the following table was used.

Example 3-16 (Resin Composition)

The resin composition of Example 1-20 was used. The resin composition contains a carbodilite as an additive in accordance with the conditions shown in the following table.

Example 3-17 (Resin Composition)

The resin composition of Example 1-21 was used. The resin composition contains a maleic anhydride as an additive in accordance with the conditions shown in the following table.

Example 3-18 (Resin Composition)

Dumbbell test pieces were prepared in the same manner as in Example 3-1 except that the carbon nanotube obtained in Example 1-16 was used and the component composition described in the following table was used.

Example 3-19 (Resin Composition)

Dumbbell test pieces were prepared in the same manner as in Example 3-1 except that the carbon nanotube obtained in Example 1-17 was used and the component composition described in the following table was used.

Example 3-20 (Resin Composition)

Dumbbell test pieces were prepared in the same manner as in Example 3-1 except that the carbon nanotube obtained in Example 1-18 was used and the component composition described in the following table was used.

Example 3-21 (Resin Composition)

Dumbbell test pieces were prepared in the same manner as in Example 3-1 except that the carbon nanotube obtained in Example 1-19 was used and the component composition described in the following table was used.

Example 3-22 (Resin Composition)

Dumbbell test pieces were prepared in the same manner as in Example 3-1 except that the carbon nanotube obtained in Example 1-16 was used and the component composition described in the following table was used.

Reference Example 3-1 (Resin Composition)

Using a polyamide resin, dumbbell test pieces were prepared in the same manner as in Example 3-1.

Reference Example 3-2 (Resin Composition)

Dumbbell test pieces were prepared in the same manner as in Example 3-1 except that raw-material carbon nanotube A was used as it was and the component composition shown in the following table was used.

Reference Example 3-3 (Resin Composition)

Dumbbell test pieces were prepared in the same manner as in Example 3-1 except that raw-material carbon nanotube A was blended in accordance with the conditions shown in the following table and the component composition shown in the following table was used.

Comparative Example 3-1 (Resin Composition)

Dumbbell test pieces were prepared in the same manner as in Example 3-1 except that the carbon nanotube obtained in Comparative Example 1-3 was used and the component composition described in the following table was used.

Comparative Example 3-2 (Resin Composition)

Dumbbell test pieces were prepared in the same manner as in Example 3-1 except that the carbon nanotube obtained in Comparative Example 1-4 was used and the component composition described in the following table was used.

Comparative Example 3-3 (Resin Composition)

Dumbbell test pieces were prepared in the same manner as in Example 3-1 except that the carbon nanotube obtained in Comparative Example 1-5 was used and the component composition described in the following table was used.

Comparative Example 3-4 (Resin Composition)

Dumbbell test pieces were prepared in the same manner as in Example 3-1 except that the carbon nanotube obtained in Comparative Example 1-6 was used and the component composition described in the following table was used.

Comparative Example 3-5 (Resin Composition)

Dumbbell test pieces were prepared in the same manner as in Example 3-1 except that the carbon nanotube obtained in Comparative Example 1-7 was used and the component composition described in the following table was used.

Comparative Example 3-6 (Resin Composition)

Dumbbell test pieces were prepared in the same manner as in Example 3-1 except that the carbon nanotube obtained in Comparative Example 1-8 was used and the component composition described in the following table was used.

TABLE 15

|  |  |  | Example 3-1 | Example 3-2 | Example 3-3 | Example 3-4 | Example 3-5 | Example 3-6 | Example 3-7 | Example 3-8 |
|---|---|---|---|---|---|---|---|---|---|---|
| CNT | Surface treatment reaction condition | Raw-material CNT | A | A | A | A | A | B | B | C |
|  |  | Treatment agent | Maleic anhydride | Maleic anhydride | Maleic anhydride | Maleic anhydride | Maleic anhydride | Maleic anhydride | Maleic anhydride | Maleic anhydride |
|  |  | Solvent | None | None | None | None | None | None | None | None |
|  |  | Reaction (° C.) | 180 | 180 | 180 | 180 | 200 | 180 | 180 | 180 |
|  |  | Time (hr) | 3 | 6 | 12 | 24 | 24 | 6 | 12 | 12 |
|  |  | Washing solvent | Toluene | Toluene | Toluene | Toluene | Toluene | Toluene | Toluene | Toluene |
|  | Surface element analysis XPS | Oxygen (%) | 9.6 | 18.0 | 22.7 | 28.6 | 30.4 | 18.9 | 21.6 | 22.1 |
|  |  | Sulfur (%) | Less than detection limit | Less than detection limit | Less than detection limit | Less than detection limit | Less than detection limit | Less than detection limit | Less than detection limit | Less than detection limit |
|  | Thermal reduction amount TGA | Weight loss (%) | 2.5 | 11.2 | 19.1 | 9.6 | 15.1 | 10.6 | 10.6 | 13.2 |
|  | Id/Ig Raman scattering spectroscopy | Id/Ig before reaction | 0.1 | 0.1 | 0.1 | 0.1 | 0.1 | 1.4 | 1.4 | 1.2 |
|  |  | Id/Ig after reaction | 0.2 | 0.1 | 0.1 | 0.1 | 0.1 | 2 | 1.9 | 1.6 |
|  |  | Absolute value of ΔId/Ig | 0.1 | 0 | 0 | 0 | 0.1 | 0.6 | 0.5 | 0.4 |
|  | Bound substance (surface treatment) Py-GC/MS | Detection of components (1) to (4) | Detected | Detected | Detected | Detected | Detected | Detected | Detected | Detected |
|  | Deposit (surface treatment) 13C-NMR, GPC | Detection of components (5) and (6) | 6300/900 | 6500/900 | 7000/900 | 7200/900 | 7500/900 | 6800/900 | 7000/900 | 7200/900 |
| Composition | Formulation | PA66 | 90 | 90 | 90 | 90 | 90 | 90 | 90 | 95 |
|  |  | Concentration of CNT (wt %) | 10 | 10 | 10 | 10 | 10 | 10 | 10 | 5 |
|  | Extrudability | Visual observation | ○ | ○ | ○ | ○ | ○ | ○ | ○ | ○ |
|  | Viscosity of PA composition solution | Viscosity of formic acid solution | 52 | 56 | 57 | 57 | 56 | — | — | — |
|  | Amount of remaining organic substance TGA | Organic substance/ CNT (mass %) | 5.0 | 5.3 | 5.4 | 5.7 | 5.3 | 3.8 | 4.4 | 5 |
|  | Peak temperature of cooling crystallization temperature (° C.) |  | 239 | 239 | 231 | 232 | 229 | 232 | 230 | 230 |
|  | Physical properties at 120° C. | Tensile strength (MPa) | 53 | 56 | 55 | 58 | 52 | 44 | 48 | 51 |
|  |  | Specific strength (MPa) | 45 | 47 | 46 | 48 | 44 | 37 | 41 | 44 |
|  |  | Tensile elongation (%) | 105 | 91 | 47 | 96 | 77 | 50 | 55 | 68 |
|  | Creep property | Time (sec) until deformation reaches 15% by application of stress of 30 MPa | $4.1 \times 10^4$ | $5.0 \times 10^4$ | $5.3 \times 10^4$ | $6.6 \times 10^4$ | $4.5 \times 10^4$ | $3.0 \times 10^4$ | $3.4 \times 10^4$ | $3.1 \times 10^4$ |

TABLE 16

|  |  |  | Example 3-9 | Example 3-10 | Example 3-11 | Example 3-12 | Example 3-13 | Example 3-14 | Example 3-15 |
|---|---|---|---|---|---|---|---|---|---|
| CNT | Surface treatment reaction condition | Raw-material CNT | A | B | A | A | B | A | B |
|  |  | Treatment agent | Maleic anhydride | Maleic anhydride | Maleic anhydride | Maleic anhydride | Hydrogen peroxide | Citric acid | Citric acid |
|  |  | Solvent | None | Toluene | Toluene | Toluene | None | None | None |
|  |  | Reaction (° C.) | 180 | 180 | 180 | 180 | 90 | 200 | 200 |
|  |  | Time (hr) | 3 | 24 | 24 | 24 | 12 | 5 | 5 |
|  |  | Washing solvent | Methanol | Toluene | Toluene | Toluene | Ion exchange water | Warm water | Warm water |
|  | Surface element analysis XPS | Oxygen (%) | 1.9 | 4.8 | 3.4 | 3.4 | 3.5 | 7.5 | 13.3 |
|  |  | Sulfur (%) | Less than detection limit | Less than detection limit | Less than detection limit | Less than detection limit | Less than detection limit | Less than detection limit | Less than detection limit |
|  | Thermal reduction amount TGA | Weight loss (%) | 0.6 | 1.4 | 0.5 | 0.5 | 0.2 | 1.6 | 1.9 |
|  | Id/Ig Raman scattering spectroscopy | Id/Ig before reaction | 0.1 | 1.4 | 0.1 | 0.1 | 1.4 | 0.1 | 1.4 |
|  |  | Id/Ig after reaction | 0.1 | 1.4 | 0.1 | 0.1 | 1.2 | 0.1 | 1.2 |
|  |  | Absolute value of ΔId/Ig | 0 | 0 | 0 | 0 | 0.2 | 0 | 0.2 |
|  | Bound substance (surface treatment) Py-GC/MS | Detection of components (1) to (4) | Detected | Detected | Detected | Detected | Not detected | Not detected | Not detected |

TABLE 16-continued

|  |  |  | Example 3-9 | Example 3-10 | Example 3-11 | Example 3-12 | Example 3-13 | Example 3-14 | Example 3-15 |
|---|---|---|---|---|---|---|---|---|---|
| Composition | Deposit (surface treatment) 13C-NMR, GPC | Detection of components (5) and (6) | Not detected | Not detected | Not detected | Not detected | Not detected | Not detected | Not detected |
|  | Formulation | PA66 | 90 | 90 | 90 | 85 | 90 | 90 | 90 |
|  |  | Concentration of CNT (wt %) | 10 | 10 | 10 | 15 | 10 | 10 | 10 |
|  | Extrudability | Visual observation | ○ | ○ | ○ | ○ | ○ | ○ | ○ |
|  | Viscosity of PA composition solution | Viscosity of formic acid solution | 50 | 51 | 52 | 52 | 51 | 48 | 49 |
|  | Amount of remaining organic substance TGA | Organic substance (mass %) | 2.7 | 2.7 | 2.9 | 2.9 | 2.3 | 2.4 | 2.5 |
|  | Peak temperature of cooling crystallization temperature (° C.) |  |  |  |  |  | 240 |  |  |
|  | Physical properties at 120° C. | Tensile strength (MPa) | 44 | 45 | 44 | 47 | 47 | 44 | 44 |
|  |  | Specific strength (MPa) | 37 | 38 | 37 | 39 | 40 | 37 | 37 |
|  |  | Tensile elongation (%) | 130 | 143 | 133 | 141 | 112 | 163 | 148 |
|  | Creep property | Time (sec) until deformation reaches 15% by application of stress of 30 MPa | $1.3 \times 10^4$ | $1.0 \times 10^4$ | $1.2 \times 10^4$ | $1.2 \times 10^4$ | $2.0 \times 10^4$ | $1.2 \times 10^4$ | $1.1 \times 10^4$ |

TABLE 17

|  |  |  | Example 3-16 | Example 3-17 | Example 3-18 | Example 3-19 | Example 3-20 | Example 3-21 | Example 3-22 |
|---|---|---|---|---|---|---|---|---|---|
| CNT | Surface treatment reaction condition | Raw-material CNT | A | A | A | A | A | A | B |
|  |  | Treatment agent | Maleic anhydride | Maleic anhydride | Maleic anhydride | Ethylene-maleic anhydride copolymer | Poly (acrylic acid) | Poly (acrylic acid)-maleic acid | Surface activator |
|  |  | Solvent | None | None | None | 1-Methyl-2-pyrrolidone | 1-Methyl-2-pyrrolidone | 1-Methyl-2-pyrrolidone |  |
|  |  | Initiator | None | None | AIBN | None | None | None |  |
|  |  | Reaction (° C.) | 180 | 180 | 120 | 180 | 180 | 180 |  |
|  |  | Time (hr) | 12 | 12 | 6 | 6 | 6 | 6 |  |
|  |  | Washing solvent | Toluene | Toluene | Toluene | Acetone | Acetone | Acetone |  |
|  | Surface element analysis XPS | Oxygen (%) | 22.7 | 22.7 | 12.3 | 7.3 | 5.1 | 5.9 | 0.9 |
|  |  | Sulfur (%) | Less than detection limit | Less than detection limit | Less than detection limit | Less than detection limit | Less than detection limit | Less than detection limit | Less than detection limit |
|  | Thermal reduction amount TGA | Weight loss (%) | 19.1 | 19.1 | 18.6 | 3.7 | 0.9 | 3.7 | 0.2 |
|  | Id/Ig Raman scattering spectroscopy | Id/Ig before reaction | 0.1 | 0.1 | 0.1 | 0.1 | 0.1 | 0.1 | 1.4 |
|  |  | Id/Ig after reaction | 0.1 | 0.1 | 0.2 | 0.1 | 0.1 | 0.1 | 1.1 |
|  |  | Absolute value of ΔId/Ig | 0 | 0 | 0.1 | 0 | 0 | 0 | 0.3 |
|  | Bound substance (surface treatment) Py-GC/MS | Detection of (1) to (4) in interface | Detected | Detected | Detected | — | — | — | Detected |
|  | Deposit (surface treatment) 13C-NMR, GPC | Detection of (5) and (6) in interface | 7000/900 | 7000/900 | 1000 | — | — | — | Not detected |
| Composition | Formulation | PA66 | 89 | 87 | 90 | 90 | 90 | 90 | 90 |
|  |  | Concentration of CNT (wt %) | 10 | 10 | 10 | 10 | 10 | 10 | 10 |
|  |  | Other additives | Carbodilite | Maleic anhydride | None | None | None | None | None |
|  |  | Concentration of others (%) | 1 | 3 | 0 | 0 | 0 | 0 | 0 |
|  | Extrudability | Visual observation | ○ | ○ | ○ | ○ | ○ | ○ | ○ |
|  | Viscosity of PA composition solution | Viscosity of formic acid solution | — | — | — | 53 | 55 | 55 | — |
|  | Amount of remaining organic substance TGA | Organic substance (mass %) | — | — | — | — | — | — | 1.2 |
|  | Peak temperature of cooling crystallization temperature (° C.) |  | 233 | 230 |  |  |  |  | 241 |
|  | Physical properties at 120° C. | Tensile strength (MPa) | 55 | 47 | 44 | 44 | 46 | 44 | 43 |
|  |  | Specific strength (MPa) | 47 | 39 | 37 | 37 | 39 | 37 | 36 |
|  |  | Tensile elongation (%) | 119 | 35 | 92 | 137 | 120 | 113 | 154 |

TABLE 17-continued

|  |  | Example 3-16 | Example 3-17 | Example 3-18 | Example 3-19 | Example 3-20 | Example 3-21 | Example 3-22 |
|---|---|---|---|---|---|---|---|---|
| Creep property | Time (sec) until deformation reaches 15% by application of stress of 30 MPa | $1.0 \times 10^4$ | — | — | — | — | — | $4.9 \times 10^3$ |

TABLE 18

|  |  |  | Comparative Example 3-1 | Comparative Example 3-2 | Comparative Example 3-3 | Comparative Example 3-4 | Comparative Example 3-5 | Comparative Example 3-6 | Reference Example 3-1 | Reference Example 3-2 | Reference Example 3-3 |
|---|---|---|---|---|---|---|---|---|---|---|---|
| CNT | Surface treatment reaction condition | Raw-material CNT | A | A | A | A | A | A | A | A | A |
|  |  | Treatment agent | Sulfuric acid + nitic acid | Sulfuric acid + nitic acid | Sulfuric acid | Nitic acid | Hydrogen peroxide + sulfuric acid | Gas-phase oxidation |  | Not treated | Not treated |
|  |  | Solvent | — | — | — | — | — |  |  |  |  |
|  |  | Reaction (° C.) | 70 | 70 | 180 | 70 | 80 |  |  |  |  |
|  |  | Time (hr) | 24 | 24 | 24 | 24 | 24 |  |  |  |  |
|  |  | Washing solvent | Water | Ion exchange water | Ion exchange water | Ion exchange water | Ion exchange water |  |  |  |  |
|  | Surface element analysis XPS | Oxygen (%) | 14.2 | 13.3 | 0.7 | 0.3 | 3.5 | 0.3 | 0.2 | 0.2 |  |
|  |  | Sulfur (%) | 0.3 | 0.1 | 0.1 | Less than detection limit | 0.1 | Less than detection limit | Less than detection limit | Less than detection limit |  |
|  | Thermal reduction amount TGA | Weight loss (%) | 18.1 | 16.7 | 0.4 | 0.3 | 0.4 | 0.2 | 0.1 | 0.1 |  |
|  | Id/Ig Raman scattering spectroscopy | Id/Ig before reaction | 0.1 | 0.1 | 0.1 | 0.1 | 1.4 | 0.1 | 0.1 | 0.1 |  |
|  |  | Id/Ig after reaction | 1.7 | 1.4 | 0.1 | 0.1 | 0.1 | 0.2 | 0.1 | 0.1 |  |
|  |  | Absolute value of ΔId/Ig | 1.6 | 1.3 | 0 | 0 | 0.3 | 0.1 | — | — |  |
|  | Bound substance (surface treatment) Py-GC/MS | Detection of components (1) to (4) | Not detected | Not detected | Not detected | Not detected | Not detected | Not detected | Not detected | Not detected |  |
|  | Deposit (surface treatment) 13C-NMR, GPC | Detection of components (5) and (6) | Not detected | Not detected | Not detected | Not detected | Not detected | Not detected | Not detected | Not detected |  |
| Composition | Formulation | PA66 | 90 | 85 | 90 | 90 | 90 | 85 | 100 | 90 | 85 |
|  |  | Concentration of CNT (wt %) | 10 | 15 | 10 | 10 | 10 | 15 | 0 | 10 | 15 |
|  | Extrudability | Visual observation | x | x | x | x | x | ○ | ○ | ○ | ○ |
|  | Viscosity of PA composition solution | Viscosity of formic acid solution | 20 | 24 | 40 | 42 | 42 | — | 48 | 51 | 51 |
|  | Amount of remaining organic substance TGA | Organic substance/CNT (mass %) | 1.3 | 1.4 | 0.2 | 0.2 | 1.4 | 0.8 | 0 | 0.2 | 0.3 |
|  | Peak temperature of cooling crystallization temperature (° C.) |  |  | 241 | 241 |  | 241 | 221 | 241 | 241 |  |
|  | Physical properties at 120° C. | Tensile strength (MPa) | 35 | 35 | 38 | 39 | 40 | 41 | 35 | 40 | 41 |
|  |  | Specific strength (MPa) | 29 | 29 | 32 | 33 | 34 | 34 | 31 | 33 | 33 |
|  |  | Tensile elongation (%) | 13 | 10 | 223 | 225 | 72 | 188 | 371 | 201 | 173 |

TABLE 18-continued

|  |  | Comparative Example 3-1 | Comparative Example 3-2 | Comparative Example 3-3 | Comparative Example 3-4 | Comparative Example 3-5 | Comparative Example 3-6 | Reference Example 3-1 | Reference Example 3-2 | Reference Example 3-3 |
|---|---|---|---|---|---|---|---|---|---|---|
| Creep property | Time (sec) until deformation reaches 15% by application of stress of 30 MPa | $1.5 \times 10^3$ | $1.6 \times 10^3$ | $1.6 \times 10^3$ | $1.7 \times 10^3$ | $2.5 \times 10^3$ | $3.8 \times 10^3$ | — | $1.8 \times 10^3$ | $1.7 \times 10^3$ |

As is apparent from the tables, it was confirmed that the resin compositions of the surface-treated carbon nanotubes of Examples are excellent in tensile strength, specific strength and tensile elongation.

Note that with respect to carbon nanotubes of Comparative Example 3-2, Example 3-9, Comparative Example 3-5 and Example 3-13, the surface elements of the surface-treated carbon nanotubes having a deposit of organic substance after HFIP elution were analyzed. The results are shown in Table 12.

TABLE 19

|  |  |  | Comparative Example 3-2 | Example 3-9 | Comparative Example 3-5 | Example 3-13 |
|---|---|---|---|---|---|---|
| Composition | Surface element analysis of residue after HFIP elution XPS | Carbon | 98.2 | 93.4 | 97.1 | 86.7 |
|  |  | Oxygen | 1.4 | 3.4 | 2.2 | 6.8 |
|  |  | Nitrogen | 0.4 | 3.2 | 0.6 | 6.5 |
|  |  | Sulfur | Less than detection limit | Less than detection limit | 0.1 | Less than detection limit |

Experiment 4

(Measurement Method)

Unless otherwise specified, individual measurements were performed in accordance with the methods described in <Experiment 1>.

(Raw Material)

Unless otherwise specified, the raw material described in <Experiment 1> was used. Note that resin compositions were prepared in accordance with the method described in <Experiment 1>, unless otherwise specified The amounts of remaining organic substance (TGA) and the evaluation results of other physical properties of Examples 3-1 to 3-15, Reference Examples 3-1 to 3-3 and Comparative Examples 3-1 to 3-6 of <Experiment 3> are shown.

TABLE 20

|  |  |  | Example 3-1 | Example 3-2 | Example 3-3 | Example 3-4 | Example 3-5 | Example 3-6 | Example 3-7 | Example 3-8 |
|---|---|---|---|---|---|---|---|---|---|---|
| CNT | Surface treatment reaction condition | Raw-material CNT | A | A | A | A | A | B | B | C |
|  |  | Treatment agent | Maleic anhydride | Maleic anhydride | Maleic anhydride | Maleic anhydride | Maleic anhydride | Maleic anhydride | Maleic anhydride | Maleic anhydride |
|  |  | Solvent | None | None | None | None | None | None | None | None |
|  |  | Reaction (° C.) | 180 | 180 | 180 | 180 | 200 | 180 | 180 | 180 |
|  |  | Time (hr) | 3 | 6 | 12 | 24 | 24 | 6 | 12 | 12 |
|  |  | Washing solvent | Toluene | Toluene | Toluene | Toluene | Toluene | Toluene | Toluene | Toluene |
|  | Surface element analysis XPS | Oxygen (%) | 9.6 | 18.0 | 22.7 | 28.6 | 30.4 | 18.9 | 21.6 | 22.1 |
|  |  | Sulfur (%) | Less than detection limit | Less than detection limit | Less than detection limit | Less than detection limit | Less than detection limit | Less than detection limit | Less than detection limit | Less than detection limit |
|  | Thermal reduction amount TGA | Weight loss (%) | 2.5 | 11.2 | 19.1 | 9.6 | 15.1 | 10.6 | 10.6 | 13.2 |
|  | Id/Ig Raman scattering spectroscopy | Id/Ig before reaction | 0.1 | 0.1 | 0.1 | 0.1 | 0.1 | 1.4 | 1.4 | 1.2 |
|  |  | Id/Ig after reaction | 0.2 | 0.1 | 0.1 | 0.1 | 0.1 | 2 | 1.9 | 1.6 |
|  |  | Absolute value of ΔId/Ig | 0.1 | 0 | 0 | 0 | 0.1 | 0.6 | 0.5 | 0.4 |
|  | Bound substance (surface treatment) Py-GC/MS | Detection of components (1) to (4) | Detected | Detected | Detected | Detected | Detected | Detected | Detected | Detected |

TABLE 20-continued

|  |  |  | Example 3-1 | Example 3-2 | Example 3-3 | Example 3-4 | Example 3-5 | Example 3-6 | Example 3-7 | Example 3-8 |
|---|---|---|---|---|---|---|---|---|---|---|
| | Deposit (surface treatment) 13C-NMR, GPC | Detection of components (5) and (6) | 6300/900 | 6500/900 | 7000/900 | 7200/900 | 7500/900 | 6800/900 | 7000/900 | 7200/900 |
| Composition | Formulation | PA66 | 90 | 90 | 90 | 90 | 90 | 90 | 90 | 95 |
| | | Concentration of CNT (wt %) | 10 | 10 | 10 | 10 | 10 | 10 | 10 | 5 |
| | Extrudability | Visual observation | ○ | ○ | ○ | ○ | ○ | ○ | ○ | ○ |
| | Viscosity of PA composition solution | Viscosity of formic acid solution | 52 | 56 | 57 | 57 | 56 | — | — | — |
| | Amount of remaining organic substance TGA | Organic substance (mass %) | 5.0 | 5.3 | 5.4 | 5.7 | 5.3 | 3.8 | 4.4 | 5 |
| | Physical properties at 120° C. | Tensile strength (MPa) | 53 | 56 | 55 | 58 | 52 | 44 | 48 | 51 |
| | | Specific strength (MPa) | 45 | 47 | 46 | 48 | 44 | 37 | 41 | 44 |
| | | Tensile elongation (%) | 105 | 91 | 47 | 96 | 77 | 50 | 55 | 68 |
| | Creep property | Time (sec) until deformation reaches 15% by application of stress of 30 MPa | $4.1 \times 10^4$ | $5.0 \times 10^4$ | $5.3 \times 10^4$ | $6.6 \times 10^4$ | $4.5 \times 10^4$ | $3.0 \times 10^4$ | $3.4 \times 10^4$ | $3.4 \times 10^4$ |

TABLE 21

|  |  |  | Example 3-9 | Example 3-10 | Example 3-11 | Example 3-12 | Example 3-13 | Example 3-14 | Example 3-15 |
|---|---|---|---|---|---|---|---|---|---|
| CNT | Surface treatment reaction condition | Raw-material CNT | A | B | A | A | B | A | B |
| | | Treatment agent | Maleic anhydride | Maleic anhydride | Maleic anhydride | Maleic anhydride | Hydrogen peroxide | Citric acid | Citric acid |
| | | Solvent | None | Toluene | Toluene | Toluene | None | None | None |
| | | Reaction (° C.) | 180 | 180 | 180 | 180 | 90 | 200 | 200 |
| | | Time (hr) | 3 | 24 | 24 | 24 | 12 | 5 | 5 |
| | | Washing solvent | Methanol | Toluene | Toluene | Toluene | Ion exchange water | Warm water | Warm water |
| | Surface element analysis XPS | Oxygen (%) | 1.9 | 4.8 | 3.4 | 3.4 | 3.5 | 7.5 | 13.3 |
| | | Sulfur (%) | Less than detection limit | Less than detection limit | Less than detection limit | Less than detection limit | Less than detection limit | Less than detection limit | Less than detection limit |
| | Thermal reduction amount TGA | Weight loss (%) | 0.6 | 1.4 | 0.5 | 0.5 | 0.2 | 1.6 | 1.9 |
| | Id/Ig Raman scattering spectroscopy | Id/Ig before reaction | 0.1 | 1.4 | 0.1 | 0.1 | 1.4 | 0.1 | 1.4 |
| | | Id/Ig after reaction | 0.1 | 1.4 | 0.1 | 0.1 | 1.2 | 0.1 | 1.2 |
| | | Absolute value of ΔId/Ig | 0 | 0 | 0 | 0 | 0.2 | 0 | 0.2 |
| | Bound substance (surface treatment) Py-GC/MS | Detection of components (1) to (4) | Detected | Detected | Detected | Detected | Not detected | Not detected | Not detected |
| | Deposit (surface treatment) 13C-NMR, GPC | Detection of components (5) and (6) | Not detected | Not detected | Not detected | Not detected | Not detected | Not detected | Not detected |
| Composition | Formulation | PA66 | 90 | 90 | 90 | 85 | 90 | 90 | 90 |
| | | Concentration of CNT (wt %) | 10 | 10 | 10 | 15 | 10 | 10 | 10 |
| | Extrudability | Visual observation | ○ | ○ | ○ | ○ | ○ | ○ | ○ |
| | Viscosity of PA composition solution | Viscosity of formic acid solution | 50 | 51 | 52 | 52 | 51 | 48 | 49 |
| | Amount of remaining organic substance TGA | Organic substance (mass %) | 2.7 | 2.7 | 2.9 | 2.9 | 2.3 | 2.4 | 2.5 |
| | Physical properties at 120° C. | Tensile strength (MPa) | 44 | 45 | 44 | 47 | 47 | 44 | 44 |
| | | Specific strength (MPa) | 37 | 38 | 37 | 39 | 40 | 37 | 37 |
| | | Tensile elongation (%) | 130 | 143 | 133 | 141 | 112 | 163 | 148 |
| | Creep property | Time (sec) until deformation reaches 15% by application of stress of 30 MPa | $1.3 \times 10^4$ | $1.0 \times 10^4$ | $1.2 \times 10^4$ | $1.2 \times 10^4$ | $2.0 \times 10^4$ | $1.2 \times 10^4$ | $1.1 \times 10^4$ |

TABLE 22

| | | | Comparative Example 3-1 | Comparative Example 3-2 | Comparative Example 3-3 | Comparative Example 3-4 | Comparative Example 3-5 | Comparative Example 3-6 | Reference Example 3-1 | Reference Example 3-2 | Reference Example 3-3 |
|---|---|---|---|---|---|---|---|---|---|---|---|
| CNT | Surface treatment reaction condition | Raw-material CNT | A | A | A | A | A | A | A | A | A |
| | | Treatment agent | Sulfuric acid + nitric acid | Sulfuric acid + nitric acid | Sulfuric acid | Nitric acid | Hydrogen peroxide + sulfuric acid | Gas-phase oxidation | Not treated | Not treated | Not treated |
| | | Solvent | — | — | — | — | — | | | | |
| | | Reaction (°C.) | 70 | 70 | 180 | 70 | 80 | | | | |
| | | Time (hr) | 24 | 24 | 24 | 24 | 24 | | | | |
| | | Washing solvent | Water | Ion exchange water | Ion exchange water | Ion exchange water | Ion exchange water | | | | |
| | Surface element analysis XPS | Oxygen (%) | 14.2 | 13.3 | 0.7 | 0.3 | 3.5 | 0.3 | 0.2 | 0.2 | |
| | | Sulfur (%) | 0.3 | 0.1 | 0.1 | Less than detection limit | 0.1 | Less than detection limit | Less than detection limit | Less than detection limit | Less than detection limit |
| | Thermal reduction amount TGA | Weight loss (%) | 18.1 | 16.7 | 0.4 | 0.3 | 0.4 | 0.2 | | 0.1 | 0.1 |
| | Id/Ig Raman scattering spectroscopy | Id/Ig before reaction | 0.1 | 0.1 | 0.1 | 0.1 | 1.4 | 0.1 | | 0.1 | 0.1 |
| | | Id/Ig after reaction | 1.7 | 1.4 | 0.1 | 0.1 | 1.1 | 0.2 | | 0.1 | 0.1 |
| | | Absolute value of ΔId/Ig | 1.6 | 1.3 | 0 | 0 | 0.3 | 0.1 | | — | — |
| | Bound substance (surface treatment) Py-GC/MS | Detection of components (1) to (4) | Not detected | Not detected | Not detected | Not detected | Not detected | Not detected | | Not detected | Not detected |
| | Deposit (surface treatment) 13C-NMR, GPC | Detection of components (5) and (6) | Not detected | Not detected | Not detected | Not detected | Not detected | Not detected | | Not detected | Not detected |
| Composition | Formulation | PA66 | 90 | 85 | 90 | 90 | 90 | 85 | 100 | 90 | 85 |
| | | Concentration of CNT (wt %) | 10 | 15 | 10 | 10 | 10 | 15 | 0 | 10 | 15 |
| | Extrudability | Visual observation | x | x | x | x | x | ○ | ○ | ○ | ○ |
| | Viscosity of PA composition solution | Viscosity of formic acid solution | 20 | 24 | 40 | 42 | 42 | — | 48 | 51 | 51 |
| | Amount of remaining organic substance TGA | Organic substance (mass %) | 1.3 | 1.4 | 0.2 | 0.2 | 1.4 | 0.8 | 0 | 0.2 | 0.3 |
| | Physical properties at 120° C. | Tensile strength (MPa) | 35 | 35 | 38 | 39 | 40 | 41 | 35 | 40 | 41 |
| | | Specific strength (MPa) | 29 | 29 | 32 | 33 | 34 | 34 | 31 | 33 | 33 |
| | | Tensile elongation (%) | 13 | 10 | 223 | 225 | 72 | 188 | 371 | 201 | 173 |
| | Creep property | Time (sec) until deformation reaches 15% by application of stress of 30 MPa | $1.5 \times 10^3$ | $1.6 \times 10^3$ | $1.6 \times 10^3$ | $1.7 \times 10^3$ | $2.5 \times 10^3$ | $3.8 \times 10^3$ | — | $1.8 \times 10^3$ | $1.7 \times 10^3$ |

The present application is based on Japanese Patent Application No. 2012-048374 filed with the Japan Patent Office on Mar. 5, 2012; Japanese Patent Application No. 2012-048377 filed with the Japan Patent Office on Mar. 5, 2012; Japanese Patent Application No. 2012-048454 filed with the Japanese Patent Office on Mar. 5, 2012; and Japanese Patent Application No. 2012-048459 filed with the Japan Patent Office on Mar. 5, 2012, the contents of which are incorporated by reference.

INDUSTRIAL APPLICABILITY

The carbon nanotube whose surface is treated and resin composition according to the present invention can be used in a wide variety of materials for parts including automotive parts, electrical parts, electronic parts, portable device parts, machine/industrial parts, business machine parts and aviation/space parts.

What is claimed is:

1. A surface-treated carbon nanotube containing a compound represented by any one of formula (1) to formula (4):

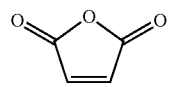   (1)

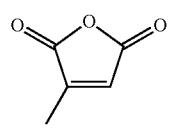   (2)

   (3)

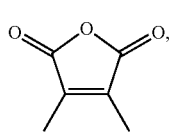   (4)

further containing a compound represented by formula (5) or formula (6):

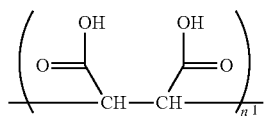   (5)

where $n^1$ is an integer of 2 to 400,

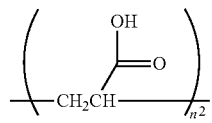   (6)

where $n^2$ is an integer of 2 to 650, and
wherein a total content of a compound represented by formula (5) or formula (6) in the surface-treated carbon nanotube is 2.0 to 40 mass %;
wherein
a thermal reduction amount at 600° C. in a nitrogen atmosphere is 0.2 to 40%;
a surface oxygen concentration measured by X-ray photoelectron spectroscopy (XPS) is 10 to 40 atm %; and
a surface sulfur concentration is less than 0.1 atm %.

2. The surface-treated carbon nanotube according to claim 1, wherein the thermal reduction amount at 600° C. in a nitrogen atmosphere is 0.5 to 40%.

3. The surface-treated carbon nanotube according to claim 1, wherein a surface treatment with at least one selected from the group consisting of an inorganic acid, an organic acid and a polymer having an organic acid as a polymerization unit is applied.

4. The surface-treated carbon nanotube according to claim 3, wherein the inorganic acid is hydrogen peroxide.

5. The surface-treated carbon nanotube according to claim 4, wherein a ratio (Id/Ig) of a peak area (Id) of a band having a range of 1335 to 1365 cm$^{-1}$ to a peak area (Ig) of a band having a range of 1565 to 1600 cm$^{-1}$ in a Raman scattering spectrum is 1.0 to 2.0.

6. The surface-treated carbon nanotube according to claim 3, wherein the organic acid is at least one selected from the group consisting of citric acid, oxalic acid, acrylic acid, diacrylic acid, methacrylic acid, maleic acid, fumaric acid, dimethylfumaric acid, itaconic acid, citraconic acid, fumaric anhydride, maleic anhydride, benzoic anhydride and acetic anhydride.

7. The surface-treated carbon nanotube according to claim 3, wherein the polymer having an organic acid as a polymerization unit is at least one selected from the group consisting of a poly(acrylic acid), a poly(acrylic acid-co-maleic acid), an ethylene-maleic anhydride and a styrene-maleic anhydride.

8. The surface-treated carbon nanotube according to claim 1, wherein a total content of a compound represented by any one of formula (1) to formula (4) in the surface-treated carbon nanotube is 0.5 to 40 mass %.

9. The surface-treated carbon nanotube according to claim 6, wherein a ratio (Id/Ig) of a peak area (Id) of a band having a range of 1335 to 1365 cm$^{-1}$ to a peak area (Ig) of a band having a range of 1565 to 1600 cm$^{-1}$ in a Raman scattering spectrum is 0.1 to 0.9.

10. The surface-treated carbon nanotube according to claim 6, wherein the surface treatment by using at least a maleic anhydride is applied.

11. The surface-treated carbon nanotube according to claim 1, wherein the surface treatment is performed in the absence of a solvent.

12. A resin composition comprising
a surface-treated carbon nanotube according to claim 1 and
a thermoplastic resin.

13. The resin composition according to claim 12, wherein the thermoplastic resin is at least a polyamide.

14. A molded article comprising a resin composition according to claim 12.

15. A resin composition comprising
a surface-treated carbon nanotube according to claim 1 and
a thermoplastic resin.

16. The resin composition according to claim 15, wherein the thermoplastic resin is at least a polyamide.

17. A molded article comprising a resin composition according to claim 15.

18. The surface-treated carbon nanotube according to claim 7, wherein a ratio (Id/Ig) of a peak area (Id) of a band having a range of 1335 to 1365 cm$^{-1}$ to a peak area (Ig) of a band having a range of 1565 to 1600 cm$^{-1}$ in a Raman scattering spectrum is 0.1 to 0.9.

19. The surface-treated carbon nanotube according to claim 7, wherein the surface treatment by using at least a maleic anhydride is applied.

20. The surface-treated carbon nanotube according to claim 1, wherein the surface treatment by using at least a maleic anhydride is applied.

21. The surface-treated carbon nanotube according to claim 10, wherein the surface oxygen concentration measured by X-ray photoelectron spectroscopy (XPS) is 18 to 40 atm %.

* * * * *